US007807173B2

(12) United States Patent
Ogrel

(10) Patent No.: US 7,807,173 B2
(45) Date of Patent: Oct. 5, 2010

(54) INFLUENZA VACCINE FORMULATION

(75) Inventor: Andrei Ogrel, Russell (CA)

(73) Assignee: Variation Biotechnologies Inc., Gatineau, Quebec (CA)

(*) Notice: Subject to any disclaimer, the term of this patent is extended or adjusted under 35 U.S.C. 154(b) by 0 days.

(21) Appl. No.: 11/948,505

(22) Filed: Nov. 30, 2007

(65) Prior Publication Data

US 2008/0193472 A1 Aug. 14, 2008

Related U.S. Application Data

(60) Provisional application No. 60/868,008, filed on Nov. 30, 2006.

(51) Int. Cl.
*A61K 39/00* (2006.01)
*A61K 39/145* (2006.01)
*A61K 38/00* (2006.01)
*C07K 14/11* (2006.01)

(52) U.S. Cl. ................. 424/186.1; 424/185.1; 530/300; 530/326

(58) Field of Classification Search ........................ None
See application file for complete search history.

(56) References Cited

U.S. PATENT DOCUMENTS

2002/0183484 A1 12/2002 Torres
2004/0223976 A1 11/2004 Bianchi et al.

FOREIGN PATENT DOCUMENTS

WO 03/066090 A1 8/2003
WO 2006/128294 A2 5/2007
WO 2007056266 A2 5/2007
WO WO 2007/051036 * 5/2007

OTHER PUBLICATIONS

Bowie et al., "Deciphering the message in protein sequences: tolerance to amino acid substitutions," Science, vol. 247 No. 4948, pp. 1306-1310 (Mar. 1990).*

Crowe et al.,"Identification of protective and non-protective T cell epitopes in influenza," Vaccine, vol. 24 No. 4, pp. 452-456 (Jan. 2006).*

GenPept ABJ51684, "hemagglutinin [Influenza A virus (A/chicken/Viet Nam/11/2005(H5N1))]," Oct. 2006.*

GenPept ABJ96856, "hemagglutinin [Influenza A virus, (A/goose/Shantou/2104/2006(H5N1))]," Oct. 2006.*

Hioe et al., "Overlapping cytotoxic T-lymphocyte and B-cell antigenic sites on the influenza virus H5 hemagglutinin," Journal of Virology, vol. 64 No. 12, pp. 6246-6251 (Dec. 1990).*

Mateu et al., "A single amino acid substitution affects multiple overlapping epitopes in the major antigenic site of foot-and-mouth disease virus of serotype C," Journal of General Virology, vol. 71 No. 3, pp. 629-637 (Mar. 1990).*

Riffkin et al., "A single amino-acid change between the antigenically different extracellular serine proteases V2 and B2 from Dichelobacter nodosus," Gene, vol. 167 Nos. 1-2, pp. 179-283 (Dec. 1995).*

Ha et al., "X-ray structure of H5 avian and H9 swine influenza virus hemagglutinins bound to avian and human receptor analogs", Proc. National Acad. Science USA, Sep. 25, 2001, vol. 98, No. 20, pp. 11181-11186.

Kaverin et al., "Structure of antigenic sites on the hemagglutinin molecule of H5 avian influenza virus and phenotypic variation of escape mutants", Journal Gen. Virology, Oct. 2002, vol. 83, Pt. 10, pp. 2497-2505.

Katz et al. "Pathogenesis of and immunity to avian influenza A H5 viruses", Biomedicine and Pharmacotherapy, Elsevier, Paris, Fr., vol. 54, No. 4, May 1, 2000, pp. 178-187 XP005888635.

European Patent Application No. 07855446.6: Extended European Search Report dated Jan. 26, 2010.

* cited by examiner

*Primary Examiner*—Zachariah Lucas
(74) *Attorney, Agent, or Firm*—David Nauman; Borden Ladner Gervais LLP

(57) ABSTRACT

Peptide-based anti-influenza formulations against influenza are disclosed. The peptides are derived from influenza-based epitopes. The formulations are based on peptide mixtures which may be formulated so that variability is present at particular residues. The formulations can be used to prepare vaccines for preventing influenza, particularly avian influenza.

11 Claims, 23 Drawing Sheets a) INFA-H5-1-V1:
Consensus sequence: NHEASSGVSSASPYQGKSSFF

| | | | | | | | | | | | | | | | | | | | | |
|---|---|---|---|---|---|---|---|---|---|---|---|---|---|---|---|---|---|---|---|---|
| N | H | E | A | S | S | G | V | S | S | A | S | P | Y | Q | G | K | S | S | F | F |
| | | D | | | L | | | | | | | | | N | | R | | | | |
| | | | | | | | | | | | | | | L | | | | | | |

b) INFA-H5-1-V2:
Consensus sequence: PNDAAEQTKLYQNPTTY

| | | | | | | | | | | | | | | | | |
|---|---|---|---|---|---|---|---|---|---|---|---|---|---|---|---|---|
| P | N | D | A | A | E | Q | T | K | L | Y | Q | N | P | T | T | Y |
| | | | | | | | I | R | | | | | S | N | | |

c) INFA-H5-1-V3:
Consensus sequence: SWSNHEASLIKKNSAYPT

| | | | | | | | | | | | | | | | | | |
|---|---|---|---|---|---|---|---|---|---|---|---|---|---|---|---|---|---|
| S | W | S | N | H | E | A | S | L | I | K | K | N | S | A | Y | P | T |
| | | | S | | D | | | | | | | | N | T | | | |
| | | | | | | | | | | | | | | V | | | |

d) INFA-H5-1-V4:
Consensus sequence: GKLSDLDGVKPLILLEYGNSNTK

| | | | | | | | | | | | | | | | | | | | | | | |
|---|---|---|---|---|---|---|---|---|---|---|---|---|---|---|---|---|---|---|---|---|---|---|
| G | K | L | S | D | L | D | G | V | K | P | L | I | L | L | E | Y | G | N | S | N | T | K |
| | | | | S | | K | | | | | | | | | | | | | | D | A | |
| | | | | | | N | | | | | | | | | | | | | | | | |

e) INFA-H5-1-V5:
Consensus sequence: TIKRSYNNTNQEDKPNDAINFESN

| | | | | | | | | | | | | | | | | | | | | | | | |
|---|---|---|---|---|---|---|---|---|---|---|---|---|---|---|---|---|---|---|---|---|---|---|---|
| T | I | K | R | S | Y | N | N | T | N | Q | E | D | K | P | N | D | A | I | N | F | E | S | N |
| | | | | T | | | | | | V | | | R | | | | S | | | | | | T |

FIG. 18 f) INFA-H5-1-V6:

Consensus sequence: ISVGTSTLNQRLVPKI

| | | | | | | | | | | | | | | | |
|---|---|---|---|---|---|---|---|---|---|---|---|---|---|---|---|
| I | S | V | G | T | S | T | L | N | Q | R | L | V | P | K | I |
| V | | | | | | | | | | | S | I | | E | |
| | | | | | | | | | | | | | | R | |

g) INFA-H5-1-V7:

Consensus sequence: KANPANDLGNPMSDEFINVPEW

| | | | | | | | | | | | | | | | | | | | | | |
|---|---|---|---|---|---|---|---|---|---|---|---|---|---|---|---|---|---|---|---|---|---|
| K | A | N | P | A | N | D | L | G | N | P | M | S | D | E | F | I | N | V | P | E | W |
| | D | S | | V | | G | | | | | | | | | | L | | | | | |

h) INFA-H5-1-V8:

Consensus sequence: PYQGKSSFFRNVVWLIKKNSAY

| | | | | | | | | | | | | | | | | | | | | | |
|---|---|---|---|---|---|---|---|---|---|---|---|---|---|---|---|---|---|---|---|---|---|
| P | Y | Q | G | K | S | S | F | F | R | N | V | V | W | L | I | K | K | N | S | A | Y |
| | | N | | R | | | | | | | | | | | | | | | N | T | |
| | | L | | | | | | | | | | | | | | | | | | V | |

i) INFA-H5-1-V 8L:

Consensus sequence: PYQGKSSFFRNVVWLIKKNSAY

| | | | | | | | | | | | | | | | | | | | | | | | | | |
|---|---|---|---|---|---|---|---|---|---|---|---|---|---|---|---|---|---|---|---|---|---|---|---|---|---|
| Palm$_2$ | K | S | S | P | Y | Q | G | K | S | S | F | F | R | N | V | V | W | L | I | K | K | N | S | A | Y |
| | | | | | | N | | R | | | | | | | | | | | | | | | N | T | |
| | | | | | | L | | | | | | | | | | | | | | | | | | V | |

FIG. 18 (continued)

INFLUENZA VACCINE FORMULATION

The present application claims priority from U.S. provisional application No. 60/868,008 filed Nov. 30, 2006, which is incorporated herein by reference.

FIELD OF THE INVENTION

The present invention relates generally to an anti-viral formulation, and in particular relates to a peptide-based influenza vaccine formulation, more particularly to an avian influenza peptide-based vaccine formulation.

BACKGROUND OF THE INVENTION

Avian influenza is an infectious disease of birds caused by type A strains of the influenza virus. The disease, which was first identified in Italy more than 100 years ago, occurs worldwide. Sixteen subtypes of influenza virus are known to infect birds, thus providing an extensive reservoir of influenza viruses potentially circulating in bird populations. To date, all known outbreaks of the highly pathogenic form have been caused by influenza A viruses of subtypes H5 and H7.

Of the 16 avian influenza virus subtypes, H5N1 is of particular concern for several reasons. H5N1 mutates rapidly and has a documented propensity to acquire genes from viruses, thereby facilitating infection of other animal species. Indeed, its ability to cause severe disease in humans has now been documented. Laboratory studies have demonstrated that isolates from this virus have a high pathogenicity and can cause mortality in humans.

Two other avian influenza viruses have recently been found to cause illness in humans: H7N7 and H9N2.

All type A influenza viruses are genetically labile and well adapted to elude host defenses. Influenza viruses lack mechanisms for the "proofreading" and repair of errors that occur during replication. As a result of these uncorrected errors, the genetic composition of the viruses changes as they replicate in humans and animals, and new antigenic variants emerge. These constant, permanent and usually small changes in the antigenic composition of influenza A viruses are known as antigenic "drift".

Influenza viruses are typed as A or B on the basis of relatively stable intracellular nucleoproteins and envelope associated matrix proteins. Virus subtypes are based on two proteins in the viral envelope, hemagglutinin (HA) and neuraminidase (NA), which undergo constant antigenic change. 16 distinct subtypes of HA and 9 subtypes of NA are recognized for influenza A viruses. The sudden appearance of a new subtype (antigenic shift) has caused three major pandemics in the past century: 1918 (Spanish Flu, H1N1), 1957 (Asian Flu, H2N2) and 1968 (Hong Kong Flu, H3N2).

Influenza viruses have a second characteristic of great public health concern: influenza A viruses can swap or "re-assort" genetic materials between subtypes of any species resulting in novel subtypes. This reassortment process, known as antigenic "shift," has resulted in worldwide pandemics in humans.

Influenza pandemics have occurred, on average, three to four times each century when new virus subtypes have emerged that are readily transmitted from person to person. In the 20th century, the great influenza pandemic of 1918-1919, which caused an estimated 40 to 50 million deaths worldwide, was followed by pandemics in 1957-1958 and 1968-1969. Experts surmise that another influenza pandemic is inevitable and possibly imminent. Given the unpredictable behaviour of influenza viruses, neither the timing nor the severity of the next pandemic can be predicted with any certainty.

Seven variable B-cell epitopes, and one variable T-cell epitope collectively represent the antigenic drift sites found on the hemagglutinin HA1 protein of Influenza A (subtype H5). Each of the B-cell variable epitopes represents a conformational epitope, and four of them are comprised of two discontinuous stretches of amino acids. There are two extended antigenic sites on the HA1 proteins, and each of them is represented by two distinct peptide sequences. The nonadjacent segments (stretches of amino acids) that are artificially joined together to represent the discontinuous epitopes are selected using the three-dimensional structure of A/duck/Singapore/3/97 hemagglutinin (PDB ID code: 1JSM). Use of crystallographic data aids in design of linear peptides that can mimic the native conformational epitopes of proteins. The T-cell eptiope is represented by a linear peptide sequence which may also be lipidated.

To date, no effective peptide-based vaccine against avian influenza is commercially available.

Current antiviral therapies may be clinically effective against influenza A virus strains in otherwise healthy adults and children; however, these therapies have limitations. Some of these drugs are expensive and supplies are limited. The vaccine composition must also change each year to account for changes in the virus circulating in the population due to antigenic drift. At least four months of development time is required to produce a new effective vaccine in significant quantities.

Processes for preparation of an immunogenic peptide mixture are described by Torres in U.S. Pat. No. 7,118,874, and in PCT application PCT/CA06/000891, herein incorporated by reference. According to one of these processes, the variability of immunogenic epitope sequences of a pathogen are evaluated. A peptide mixture is synthesized comprising a plurality of peptides representative of the frequency with which different amino acids are found at variable residues of selected epitopes.

Thus, there is a need to develop a vaccine formulation effective against multiple subtypes and multiple variants of avian influenza.

SUMMARY OF THE INVENTION

It is an object of the present invention to obviate or mitigate at least one disadvantage of previous influenza vaccine formulations.

In a first aspect, the present invention provides a peptide-based anti-influenza formulation comprising at least one peptide selected from the group consisting of SEQ ID NOs: 1 to 496 and analogues thereof. Particularly, the present invention provides a peptide-based anti-influenza formulation comprising at least one peptide selected from the group consisting of SEQ ID NOs: 1 to 248 and analogues thereof. In addition, the present invention provides a formulation comprising at least one peptide selected from the group consisting of SEQ ID NOs: 249 to 496 and analogues thereof. In exemplary embodiments, the present invention provides a formulation comprising at least one peptide selected from the group consisting of SEQ ID NOs: 1 to 212, a formulation comprising at least one peptide selected from the group consisting of SEQ ID NOs: 249 to 460, a formulation comprising peptides selected from the group consisting of: a) SEQ ID NOs: 1 to 212, and b) SEQ ID NOs: 249 to 460; a formulation comprising peptides selected from the group consisting of: a) SEQ ID NOs: 213 to 248, and b) SEQ ID NOs: 461 to 496; a formulation comprising peptides selected from the group consisting of: a) SEQ ID NOs: 1 to 248, and b) SEQ ID NOs: 249 to 496; or a formulation comprising peptides selected from the group consisting of: a) SEQ ID NOs: 1 to 40, and b) SEQ ID NOs: 249 to 288.

In another exemplary embodiment of the present invention, the formulation comprises at least one peptide sequence from at least one of the following groups: a) SEQ ID NOs: 1 to 24; b) SEQ ID NOs: 25 to 40; c) SEQ ID NOs: 41 to 64; d) SEQ ID NOs: 65 to 88; e) SEQ ID NOs: 89 to 120; f) SEQ ID NOs: 121 to 144; g) SEQ ID NOs: 145 to 176, h) SEQ ID NOs: 177 to 212; i) SEQ ID NOs: 249 to 272; j) SEQ ID NOs: 273 to 288; k) SEQ ID NOs: 289 to 312; l) SEQ ID NOs: 313 to 336; m) SEQ ID NOs: 337 to 368; n) SEQ ID NOs: 369 to 392; o) SEQ ID NOs: 393 to 424; or p) SEQ ID NOs: 425 to 460.

In yet another exemplary embodiment of the present invention, the formulation comprises $2^n$ peptide sequences from at least one of the following groups: a) SEQ ID NOs: 1 to 24; b) SEQ ID NOs: 25 to 40; c) SEQ ID NOs: 41 to 64; d) SEQ ID NOs: 65 to 88; e) SEQ ID NOs: 89 to 120; f) SEQ ID NOs: 121 to 144; g) SEQ ID NOs: 145 to 176, h) SEQ ID NOs: 177 to 212, i) SEQ ID NOs: 249 to 272; j) SEQ ID NOs: 273 to 288; k) SEQ ID NOs: 289 to 312; l) SEQ ID NOs: 313 to 336; m) SEQ ID NOs: 337 to 368; n) SEQ ID NOs: 369 to 392; o) SEQ ID NOs: 393 to 424; or p) SEQ ID NOs: 425 to 460, wherein n is 1 to 4.

The formulation can further comprise at least one peptide sequence from SEQ ID NOs: 213 to 248, or SEQ ID NOs: 461 to 496.

In a further aspect of the present invention there is provided a vaccine comprising the formulation comprising at least one peptide selected from the group consisting of SEQ ID NOs: 1 to 496 and analogues thereof, together with a pharmaceutically-acceptable diluent or carrier. The vaccine can further comprise an adjuvant. In one example, the adjuvant is alum.

The anti-viral formulation can be an anti-influenza formulation. More particularly, the anti-influenza formulation can be an avian anti-influenza formulation.

In a further aspect of the present invention, there is provided a use of the formulation comprising at least one peptide selected from the group consisting of SEQ ID NOs: 1 to 496 and analogues thereof, for the preparation of a vaccine. The vaccine can be used for preventing or treating influenza in an animal in need thereof. In one exemplary embodiment, the influenza is avian influenza. The present invention further relates to a method for inducing an immune response in humans or animals and conferring protection against avian influenza, or novel subtypes of influenza derived from avian influenza, which comprises administering to humans or other animals a peptide-based vaccine as described herein.

In a further aspect of the present invention, there is provided a method for preparing an anti-viral formulation, such as the anti-viral formulation as described herein. According to one embodiment, there is provided a method for preparing a peptide from SEQ ID NOs: 1 to 212 comprising the steps of determining a linear sequence representative of primary sequences of discontinuous epitopes of an avian influenza viral protein, wherein the epitopes are in proximity to each other when the protein is in a folded conformation; and synthesizing a peptide representative of the linear sequence. In another embodiment, there is provided method for preparing a peptide mixture comprising any two peptide sequences from SEQ ID NOs: 1 to 212 comprising the steps of: determining a linear sequence representative of primary sequences of discontinuous epitopes of an avian influenza viral protein, the epitopes being in proximity to each other when the protein is in a folded conformation; said discontinuous epitopes comprising variable residues, and synthesizing a peptide mixture including at least two different amino acids at a variable residue.

In yet another aspect, the present invention relates generally to an anti-influenza vaccine comprising a mixture of peptides containing at least one hemagglutinin (HA) antigen of influenza virus. Hemagglutinin (HA) is a potent immunogen, and viral neutralizing antibodies are directed against the variable regions of HA. The isolated peptide mixture represents variants of multiple variable regions of hemagglutinin. Thus, in accordance with one aspect of the present invention, there is provided an anti-viral formulation comprising a mixture of isolated peptides, said mixture being formulated on the basis of the variable region of the avian influenza virus HA protein and said isolated peptide mixture representing variants of a variable region of the HA or HA1 protein, wherein each of said variable regions comprising a plurality of variable amino acid residues, at least one of which is represented by two or more amino acids.

In one embodiment, the plurality of variable amino acid residues in the anti-viral formulation comprises three or more residues. One or more of said Avian influenza proteins can be an HA or HA1.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

Embodiments of the present invention will now be described, by way of example only, with reference to the attached Figures, wherein:

FIG. 18(*a*)-(*h*) shows the different variosite peptide sequences of the present invention, with variable residues beneath the consensus sequence. FIG. 18(*a*) is INFA-H5-1-V1; FIG. 18(*b*) is INFA-H5-1-V2; FIG. 18(*c*) is INFA-H5-1-V3; FIG. 18(*d*) is INFA-H5-1-V4; FIG. 18(*e*) is INFA-H5-1-V5; FIG. 18(*f*) is INFA-H5-1-V6; FIG. 18(*g*) is INFA-H5-1-V7; FIG. 18(*h*) is INFA-H5-1-V8.

FIG. 18(*i*) shows different lipidated variosite peptide sequences based on the consensus sequence in FIG. 18(*h*).

DETAILED DESCRIPTION

Figure 1:
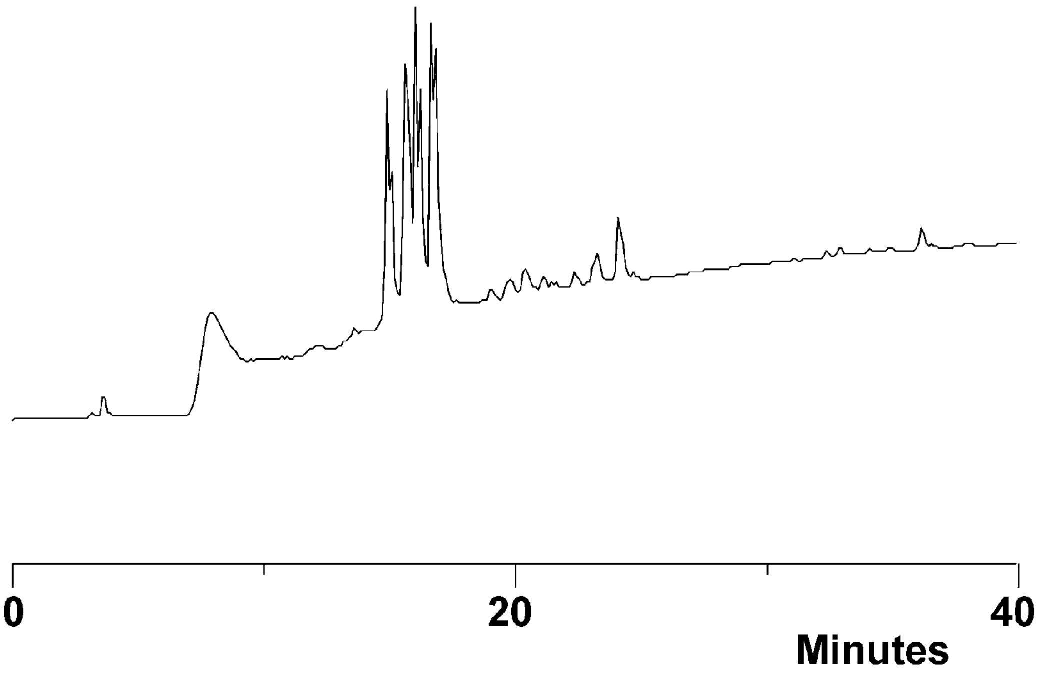
FIG. 1 shows an analytical HPLC chromatogram of crude INFA-H5-1-V1 peptide sequences (corresponding to SEQ ID NOs: 249 to 272).

Generally, the present invention provides an anti-influenza formulation, and, more specifically, a vaccine for Influenza A, including avian subtypes.

In a first aspect, the present invention provides a peptide-based anti-influenza formulation comprising at least one peptide selected from the group consisting of SEQ ID NOs: 1 to 496 and analogues thereof. Particularly, the present invention provides a peptide-based anti-influenza formulation comprising at least one peptide selected from the group consisting of SEQ ID NOs: 1 to 248 and analogues thereof. In addition, the present invention provides a formulation comprising at least one peptide selected from the group consisting of SEQ ID NOs: 249 to 496 and analogues thereof. In exemplary embodiments, the present invention provides a formulation comprising at least one peptide selected from the group consisting of SEQ ID NOs: 1 to 212, a formulation comprising at least one peptide selected from the group consisting of SEQ ID NOs: 249 to 460, a formulation comprising peptides selected from the group consisting of: a) SEQ ID NOs: 1 to 212, and b) SEQ ID NOs: 249 to 460; a formulation comprising peptides selected from the group consisting of: a) SEQ ID NOs: 213 to 248, and b) SEQ ID NOs: 461 to 496; a formulation comprising peptides selected from the group consisting of: a) SEQ ID NOs: 1 to 248, and b) SEQ ID NOs: 249 to 496; or a formulation comprising peptides selected from the group consisting of: a) SEQ ID NOs: 1 to 40, and b) SEQ ID NOs: 249 to 288.

In another exemplary embodiment of the present invention, the formulation comprises at least one peptide sequence from at least one of the following groups: a) SEQ ID NOs: 1 to 24; b) SEQ ID NOs: 25 to 40; c) SEQ ID NOs: 41 to 64; d) SEQ ID NOs: 65 to 88; e) SEQ ID NOs: 89 to 120; f) SEQ ID NOs: 121 to 144; g) SEQ ID NOs: 145 to 176, h) SEQ ID NOs: 177 to 212; i) SEQ ID NOs: 249 to 272; j) SEQ ID NOs: 273 to 288; k) SEQ ID NOs: 289 to 312; l) SEQ ID NOs: 313 to 336; m) SEQ ID NOs: 337 to 368; n) SEQ ID NOs: 369 to 392; o) SEQ ID NOs: 393 to 424; or p) SEQ ID NOs: 425 to 460.

In yet another exemplary embodiment of the present invention, the formulation comprises $2^n$ peptide sequences from at least one of the following groups: a) SEQ ID NOs: 1 to 24; b) SEQ ID NOs: 25 to 40; c) SEQ ID NOs: 41 to 64; d) SEQ ID NOs: 65 to 88; e) SEQ ID NOs: 89 to 120; f) SEQ ID NOs: 121 to 144; g) SEQ ID NOs: 145 to 176, h) SEQ ID NOs: 177 to 212, i) SEQ ID NOs: 249 to 272; j) SEQ ID NOs: 273 to 288; k) SEQ ID NOs: 289 to 312; l) SEQ ID NOs: 313 to 336; m) SEQ ID NOs: 337 to 368; n) SEQ ID NOs: 369 to 392; o) SEQ ID NOs: 393 to 424; or p) SEQ ID NOs: 425 to 460, wherein n is 1 to 4.

The formulation can further comprise at least one peptide sequence from SEQ ID NOs: 213 to 248 or SEQ ID NOs: 461 to 496.

In a further aspect of the present invention there is provided a vaccine comprising the formulation comprising at least one peptide selected from the group consisting of SEQ ID NOs: 1 to 496 and analogues thereof, together with a pharmaceutically-acceptable diluent or carrier. The vaccine can further comprise an adjuvant. In one example, the adjuvant is alum.

The anti-viral formulation can be an anti-influenza formulation. More particularly, the anti-influenza formulation can be an avian anti-influenza formulation.

In a further aspect of the present invention, there is provided a use of the formulation comprising at least one peptide selected from the group consisting of SEQ ID NOs: 1 to 496 and analogues thereof, for the preparation of a vaccine. The vaccine can be used for preventing or treating influenza in an animal in need thereof. In one exemplary embodiment, the influenza is avian influenza. The present invention further relates to a method for inducing an immune response in humans or animals and conferring protection against avian influenza, or novel subtypes of influenza derived from avian influenza, which comprises administering to humans or other animals a peptide-based vaccine as described herein.

In a further aspect of the present invention, there is provided a method for preparing an anti-viral formulation, such as the anti-viral formulation as described herein. According to one embodiment, there is provided a method for preparing a peptide from SEQ ID NOs: 1 to 212 comprising the steps of determining a linear sequence representative of primary sequences of discontinuous epitopes of an avian influenza viral protein, wherein the epitopes are in proximity to each other when the protein is in a folded conformation; and synthesizing a peptide representative of the linear sequence. In another embodiment, there is provided method for preparing a peptide mixture comprising any two peptide sequences from SEQ ID NOs: 1 to 212 comprising the steps of: determining a linear sequence representative of primary sequences of discontinuous epitopes of an avian influenza viral protein, the epitopes being in proximity to each other when the protein is in a folded conformation; said discontinuous epitopes comprising variable residues, and synthesizing a peptide mixture including at least two different amino acids at a variable residue.

In yet another aspect, the present invention relates generally to an anti-influenza vaccine comprising a mixture of peptides containing at least one hemagglutinin (HA) antigen of influenza virus. Hemagglutinin (HA) is a potent immunogen, and viral neutralizing antibodies are directed against the variable regions of HA. The isolated peptide mixture represents variants of multiple variable regions of hemagglutinin. Thus, in accordance with one aspect of the present invention, there is provided an anti-viral formulation comprising a mixture of isolated peptides, said mixture being formulated on the basis of the variable region of the avian influenza virus HA protein and said isolated peptide mixture representing variants of a variable region of the HA or HA1 protein, wherein each of said variable regions comprising a plurality of variable amino acid residues, at least one of which is represented by two or more amino acids.

In one embodiment, the plurality of variable amino acid residues in the anti-viral formulation comprises three or more residues. One or more of said Avian influenza proteins can be an HA or HA1.

The vaccine may be formulated with or without representing variation at specific residues for each peptide. When variation is not represented, the peptide formed may be referred to herein as a DISCOTOPE linear peptide sequence synthetic construct that approximates the position of primary sequence sections that compose discontinuous epitopes. The individual sections are constructed in sequence to elicit immune responses that recognize the discontinuous epitopes found in the original intact protein.

Discontinuous epitopes are composed of two or more segments of the primary sequence of a protein that when properly folded come together and are bound by specific antibodies. They are not recognized by antibodies when the secondary structure is lost and therefore have not been represented by a continuous linear peptide.

When variation is present at particular residues that are known to have different amino acids represented according to different sequences for that particular pathogen, the formulation comprises a number of peptides, which may be collectively referred to herein as a DISCOSITE variable residue peptide construct.

Design of Eptiopes

Hemagglutinin is the major surface glycoprotein of influenza virus and a potent immunogen against which viral neutralizing antibodies are directed. We have designed eight peptides that mimic discontinuous B- and T-cell epitopes on antigenic sites of HA. The sequences of these peptides are determined based on analysis of the crystal structure of influenza hemagglutinin (HA) protein to determine peptide epitopes. Hemagglutinin is the major surface glycoprotein of influenza virus and a potent immunogen against which viral neutralizing antibodies are directed. The linear peptide epitopes in the cocktail mimic discontinuous epitopes on the HA protein surface. Using bioinformatics software that analyzes the antigenic variation of HA proteins from thousands of human influenza isolates, degenerative peptide cocktails based on these epitopes can be prepared which represent the antigenic variation of HA within these epitopes. Thus, the influenza vaccine formulations of the present invention comprise a cocktail of peptides that represent major epitopes of the HA protein.

HA is the major envelope glycoprotein of influenza virus, and mediates the penetration of virus into host cells. The native HA is formed by the association of three HA monomers which, as a precondition of virus infectivity, are cleaved enzymatically into the amino-terminal HA1 and carboxy-terminal HA2. Based on the three dimensional structure of HA1, antigenic sites have been mapped by determining the amino acid changes of antigenic variants. The antigenic variations were mostly seen surrounding the receptor binding region of HA. including residues around the antibody inaccessible receptor binding pockets. Monoclonal antibodies to these antigenic sites neutralize influenza virus infectivity when the exact sequences are present. Both T and B cell epitopes are found on these sites.

All amino acids changes documented in virus escape mutants, selected by MAB or other methods, were analyzed. The proteins were aligned, and position of those amino acids was mapped onto 3-D structure of hemagglutinin H5. The location of the epitope was roughly predicted in hemagglutinin H5 protein as the area surrounds amino acids that undergo the immune pressure. Antigenic sites were then redefined using the three-dimensional structure of A/duck/Singapore/3/97 hemagglutinin (PDB ID code: 1JSM) in a sense that antigenic determinants must be freely accessible for B-cell antibodies, and that different segments of same epitope must be in close proximity to each other (for example, within 20 A).

The occurrence of amino acids at variable sites within constructed epitopes was assessed by analyzing hemagglutinin HA1 strains of Influenza A (subtype H5) virus, available in the Los Alamos Data Base as of Jun. 28, 2005. Either 460 from all hosts or only 38 human hemagglutinin HA1 strains were used for analysis. A variable residue was defined as a position in which the occurrence of the most frequent amino acid at that position is less than 85% among all viral sequences examined.

A plurality of variable amino acid residues may comprise three or more residues, with two or more different amino acids at each variable position.

Part or all of the peptides comprising an influenza vaccine may be lipidated.

Discontinuous epitopes are composed of two or more segments of the primary sequence of a protein that exist in close proximity when in a native, three-dimensional conformation. They are not recognized by antibodies when the secondary or tertiary structure is lost; thus, linear peptides cannot traditionally be used to represent discontinuous epitopes. Crystallographic data from influenza hemagglutinin was used to design linear sequences that represent at least five conformational epitopes.

From each variable epitope, the peptide length is selected, and within the peptide, a plurality of variable residues is selected. Each variable residue has at least two optional amino acids, found naturally occurring in sequenced versions of the virus. In this way, a high degree of variability is represented. For example, three or four variable residues may be represented in the mixture of peptides, each having two or more different amino acids represented in the sequenced database records for influenza variants. If two variable residues occur in a variable region, then $2^2$ different peptides would be used in the mixture representing that particular region. If three or four variable residues are indicated in a hypervariable region, the number of peptides in the resulting mixture would be $2^3$ and $2^4$, respectively. Generally, if variable regions consist of A, B, C, and so on variable sites, with a, b, c, and so on different amino acids at respective site, the total number of peptides would be $A^a \times B^b \times C^c$ and so on.

Once the proteins, variable epitopes, peptide lengths, and variable residues are selected, the synthesis of the peptide mixtures occurs, according to any acceptable method of peptide synthesis.

Peptide mixtures are synthesized with each different peptide sequence represented in roughly equimolar quantities. However, there is no requirement to provide equimolar quantities of the individual peptides.

Lipidation of peptides may be conducted by any conventional or acceptable route, as would be known to those of skill in the art. Peptides need not be lipidated, but it may be advantageous for certain peptides to be lipidated with any acceptable lipid, such as palmitic acid, so as to allow a peptide to pass through a cell membrane. Peptides incorporating lipid may benefit from placement of a KSS motif at the C-terminal. The peptides incorporating lipid may contain 1 or more lipid moieties, for example, two lipid moieties per peptide. Immunization with lipidated peptides may result in an enhanced cytotoxic T lymphocyte (CTL) response.

Peptides in accordance with one aspect of the present invention (i.e., corresponding to SEQ ID NOs. 1-212 and SEQ ID NOs. 249-460) form 8 groups derived from H5 antigenic sites on hemagglutinin. These groups are identified as INFA-H5-1-V1, INFA-H5-1-V2, INFA-H5-1-V3, INFA-H5-1-V4, INFA-H5-1-V5, INFA-H5-1-V6, INFA-H5-1-V7 and INFA-H5-1-V8. The groups contain the following sequences:

Groups INFA-H5-1-V1 (SEQ ID NOs 1-24 and SEQ ID NOs. 249-272), INFA-H5-1-V3 (SEQ ID NOs 41-64 and SEQ ID NOs. 289-312), INFA-H5-1-V4 (SEQ ID NOs 65-88 and SEQ ID NOs. 313-336) and INFA-H5-1-V6 (SEQ ID NOs 121-144 and SEQ ID NOs. 369-392) consist of 24 peptide variants.

Groups INFA-H5-1-V5 (SEQ ID NOs 89-120 and SEQ ID NOs. 337-368) and INFA-H5-1-V7 (SEQ ID NOs 145-176 and SEQ ID NOs. 393-424) consist of 32 peptide variants.

Group INFA-H5-1-V2 (SEQ ID NOs 25-40 and SEQ ID NOs. 273-288) consists of 16 peptide variants.

Group INFA-H5-1-V8 (SEQ ID NOs 177-212 and SEQ ID NOs. 425-460) consists of 36 peptide variants.

During typical preparation of the peptide sequences, an additional residue (such as a glycine residue) may be added at an end of sequence. Sequences corresponding to peptides having an additional glycine residue are shown in SEQ ID NOs: 249 to 496. The additional glycine residue has no material effect on the function of the peptide, and the presence of the glycine residue is merely a product of peptide synthesis which would be well understood to the person of ordinary skill in the art. In addition, therefore, peptides normally synthesized in this manner would represent typical examples of "analogues" (as described below) of peptides used in the preparation of formulations in accordance with one aspect of the present invention.

Figure 9:
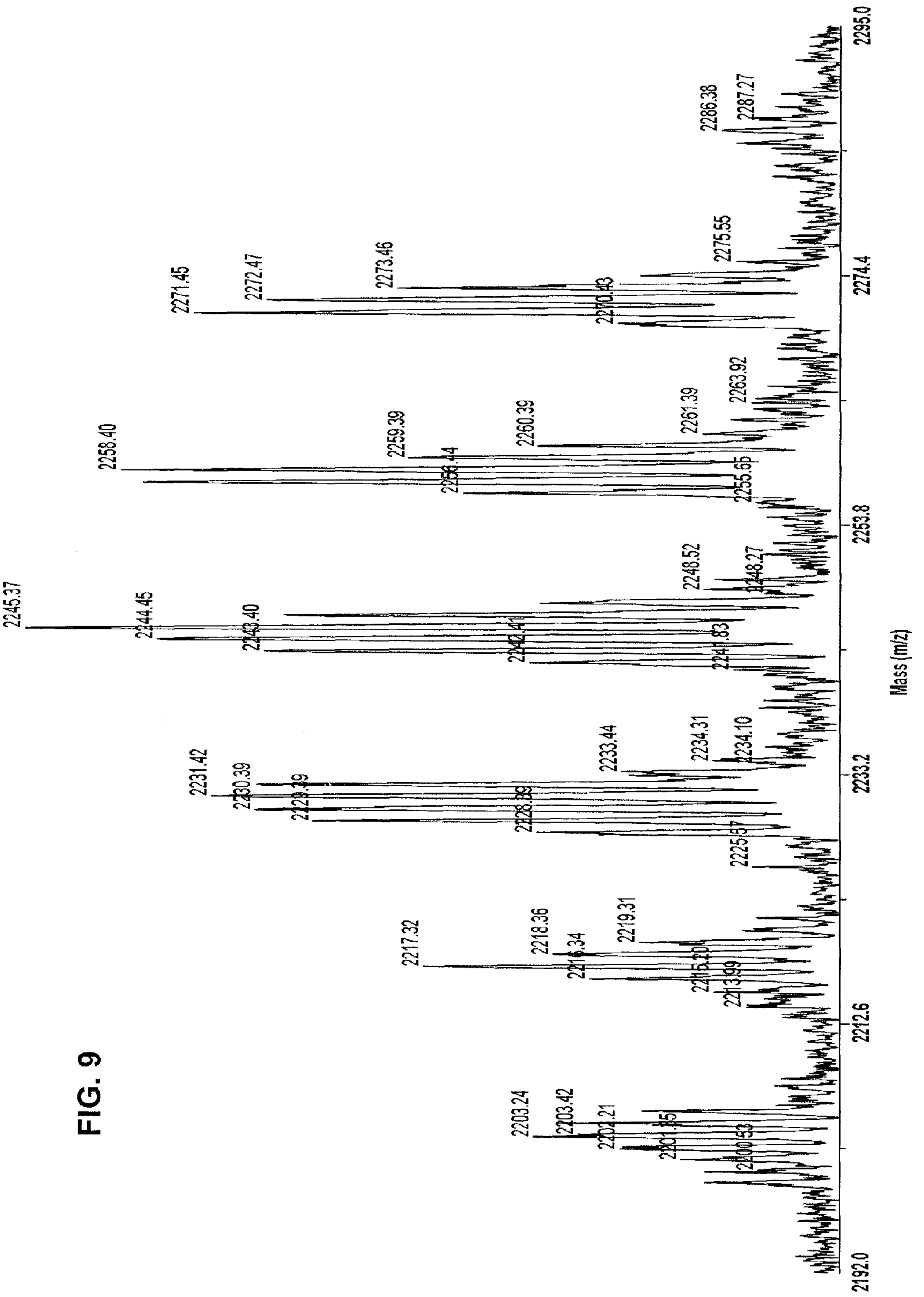
FIG. 9 shows a MALDI-TOF spectrum of crude INFA-H5-1-V1 peptide sequences (corresponding to SEQ ID NOs: 249 to 272).

FIGS. 1 and 9 are related to peptide group INFA-H5-1-V1. FIG. 1 shows an analytical HPLC chromatogram of crude INFA-H5-1-V1 peptides. FIG. 9 shows a MALDI-TOF spectrum of crude INFA-H5-1-V1 peptides.

Figure 2:
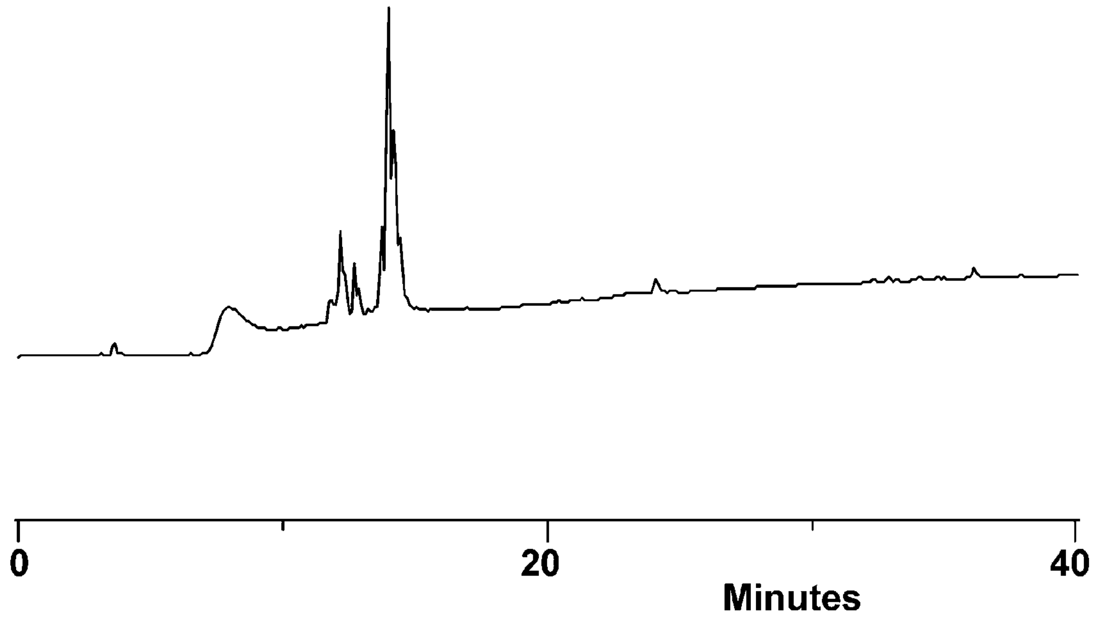
FIG. 2 shows an analytical HPLC chromatogram of crude INFA-H5-1-V2 peptide sequences (corresponding SEQ ID NOs: 273 to 288).
Figure 10:
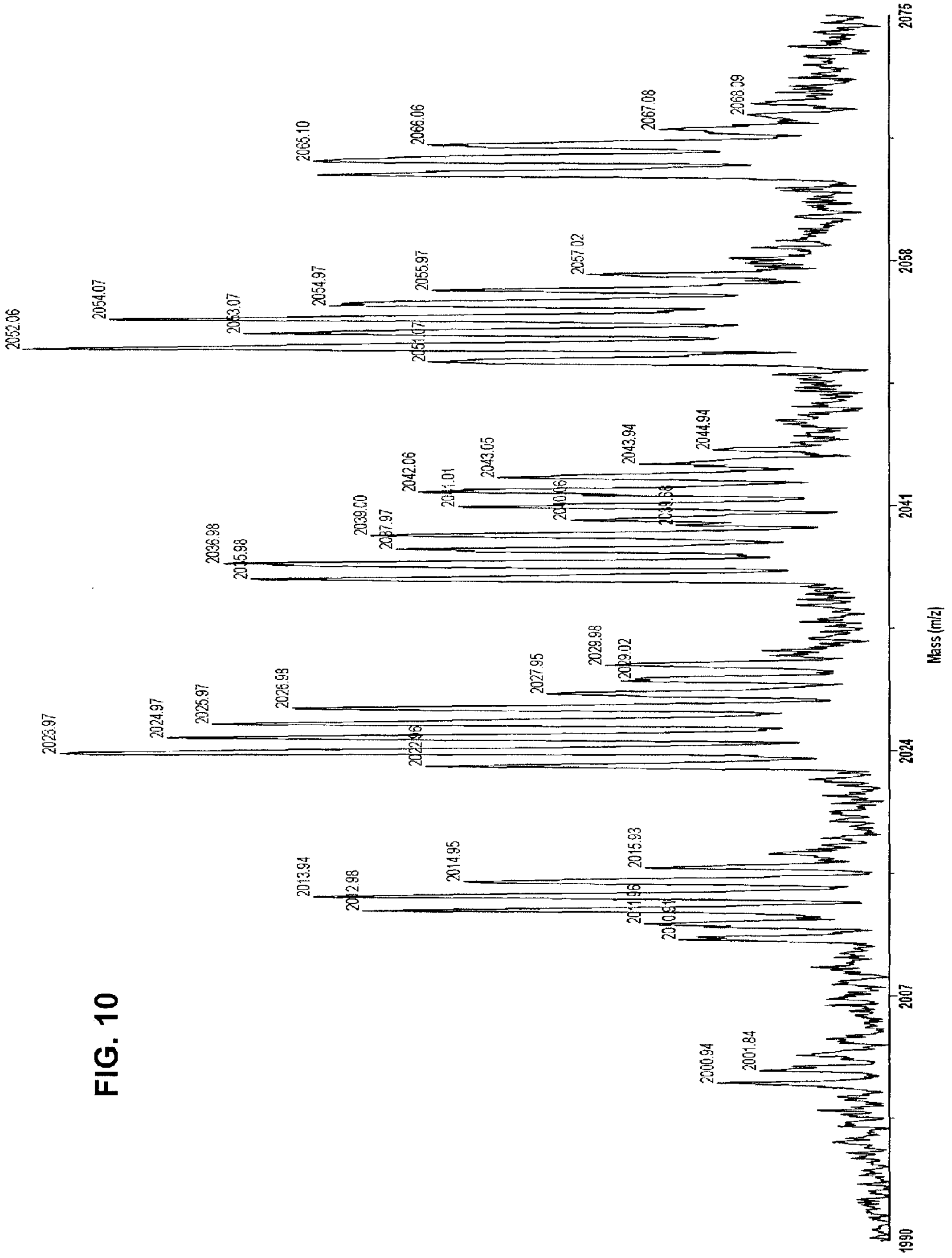
FIG. 10 shows a MALDI-TOF spectrum of crude INFA-H5-1-V2 peptide sequences (corresponding to SEQ ID NOs: 273 to 288).

FIGS. 2 and 10 are related to peptide group INFA-H5-1-V2. FIG. 2 shows an analytical HPLC chromatogram of crude INFA-H5-1-V2 peptides. FIG. 10 shows a MALDI-TOF spectrum of crude INFA-H5-1-V2 peptides.

Figure 3:
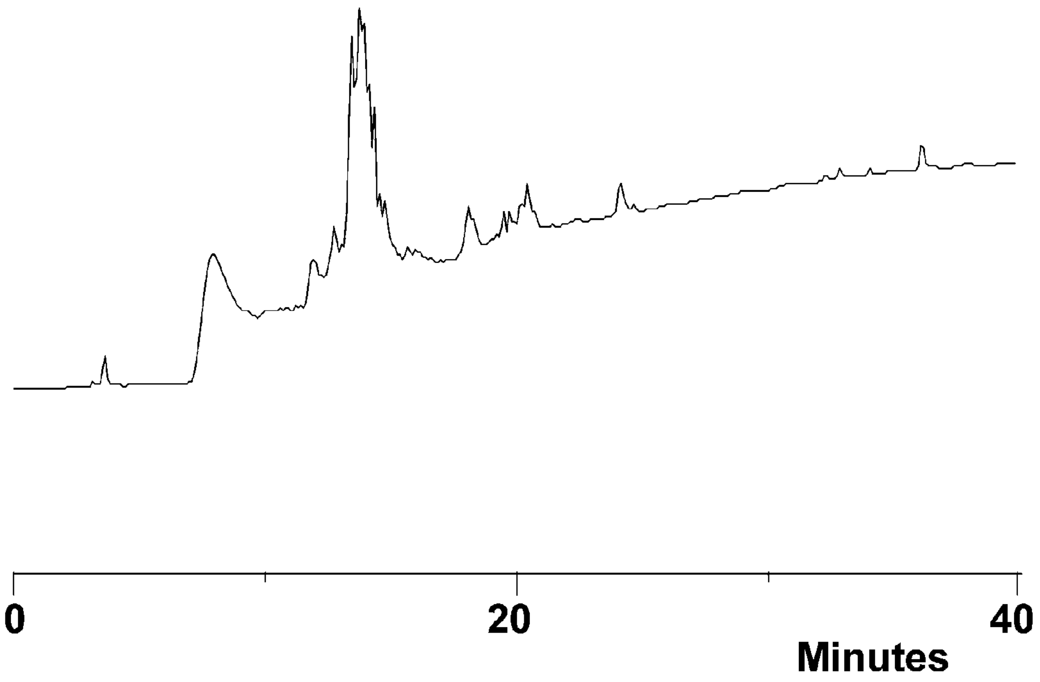
FIG. 3 shows an analytical HPLC chromatogram of crude INFA-H5-1-V3 peptide sequences (corresponding to SEQ ID NOs: 289 to 312).
Figure 11:
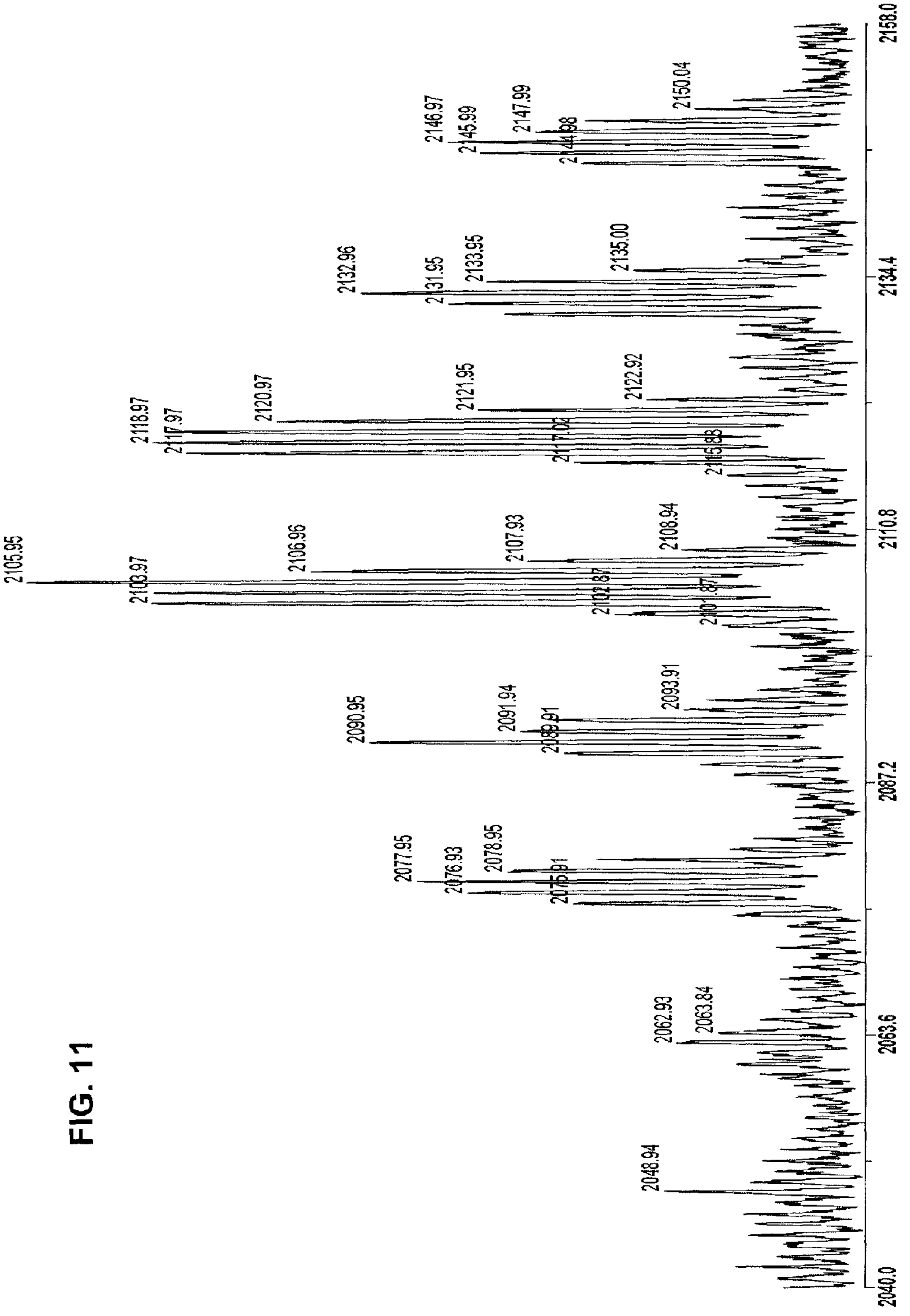
FIG. 11 shows a MALDI-TOF spectrum of crude INFA-H5-1-V3 peptide sequences (corresponding to SEQ ID NOs: 289 to 312).

FIGS. 3 and 11 are related to peptide group INFA-H5-1-V3. FIG. 3 shows an analytical HPLC chromatogram of crude INFA-H5-1-V3 peptides. FIG. 11 shows a MALDI-TOF spectrum of crude INFA-H5-1-V3 peptides.

Figure 4:
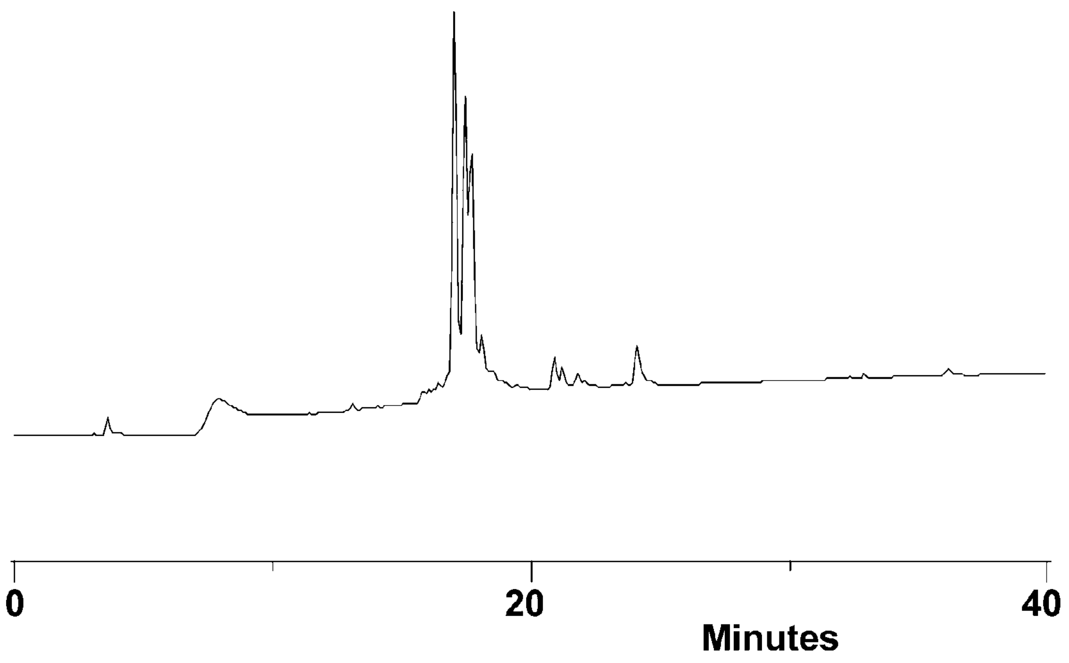
FIG. 4 shows an analytical HPLC chromatogram of crude INFA-H5-1-V4 peptide sequences (corresponding to SEQ ID NOs: 313 to 336).
Figure 12:
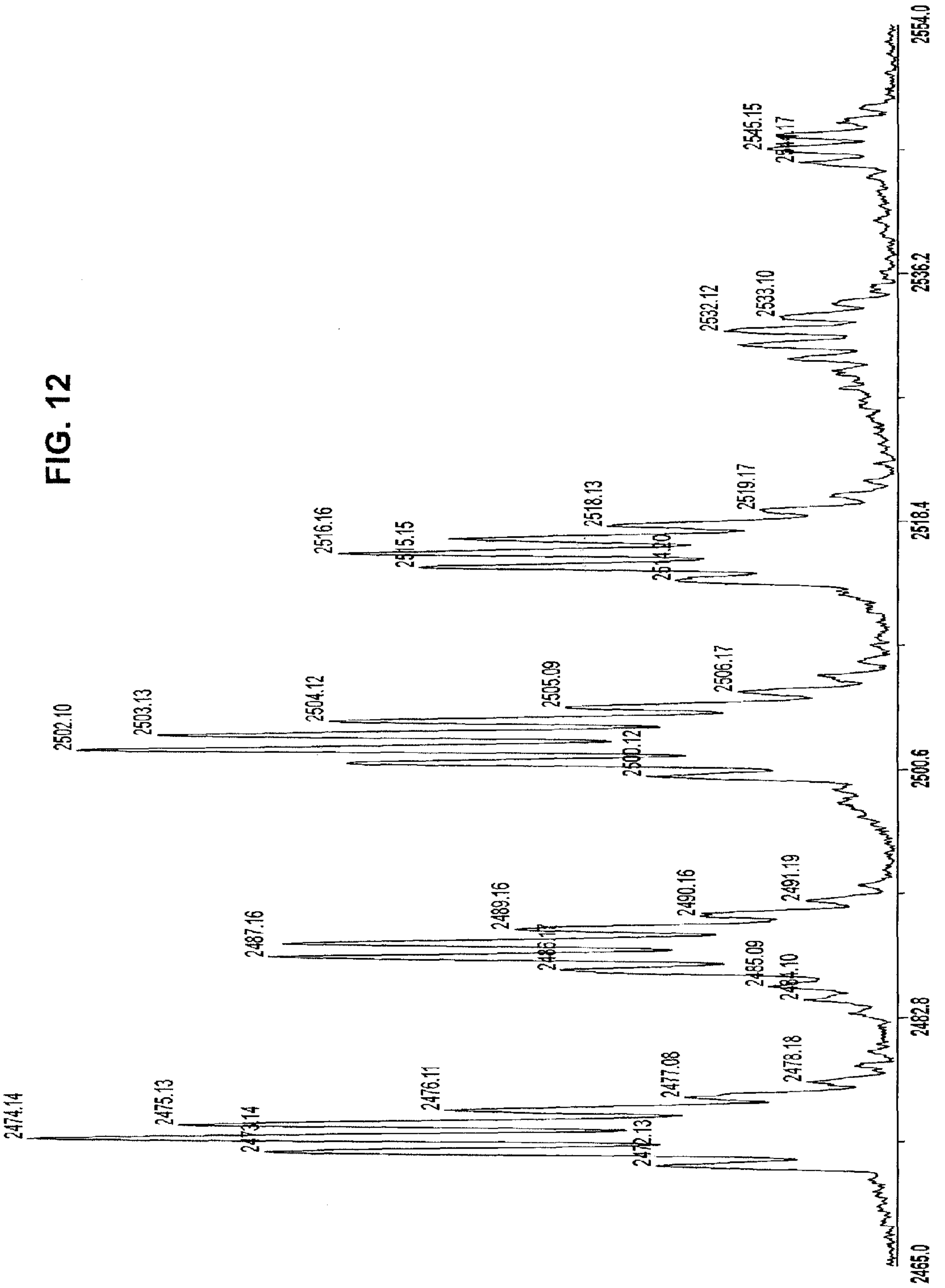
FIG. 12 shows a MALDI-TOF spectrum of crude INFA-H5-1-V4 peptide sequences (corresponding to SEQ ID NOs: 313 to 336).

FIGS. 4 and 12 are related to peptide group INFA-H5-1-V4. FIG. 4 shows an analytical HPLC chromatogram of crude INFA-H5-1-V4 peptides. FIG. 12 shows a MALDI-TOF spectrum of crude INFA-H5-1-V4 peptides.

Figure 5:
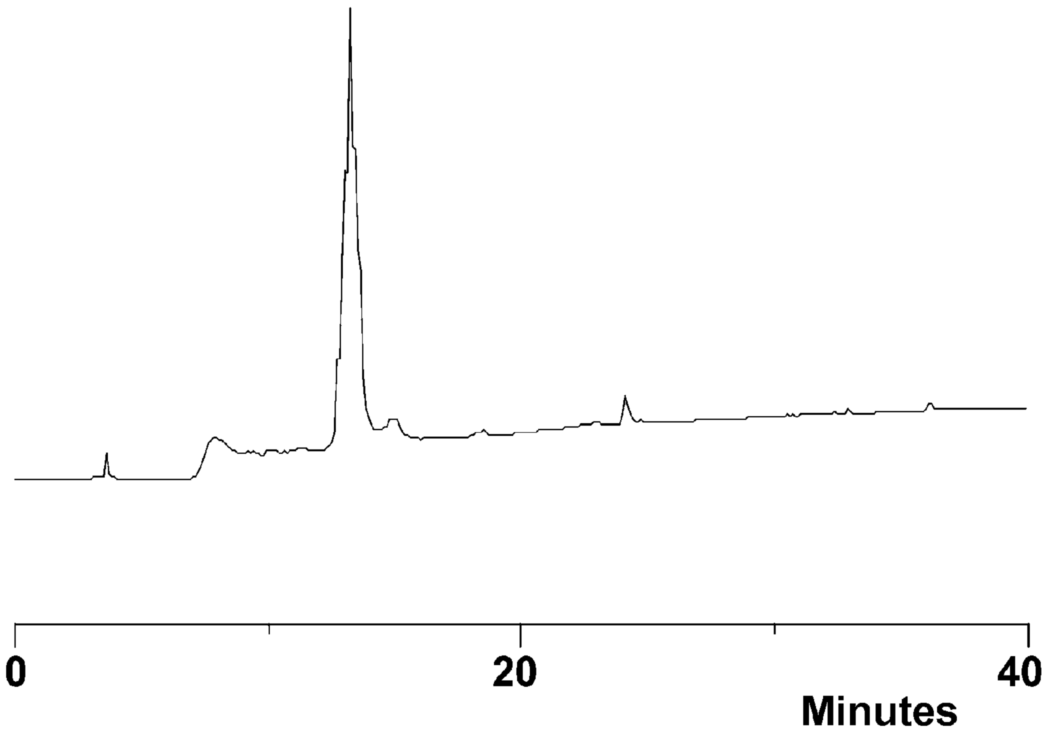
FIG. 5 shows an analytical HPLC chromatogram of crude INFA-H5-1-V5 peptide sequences (corresponding to SEQ ID NOs: 337 to 368).
Figure 13:
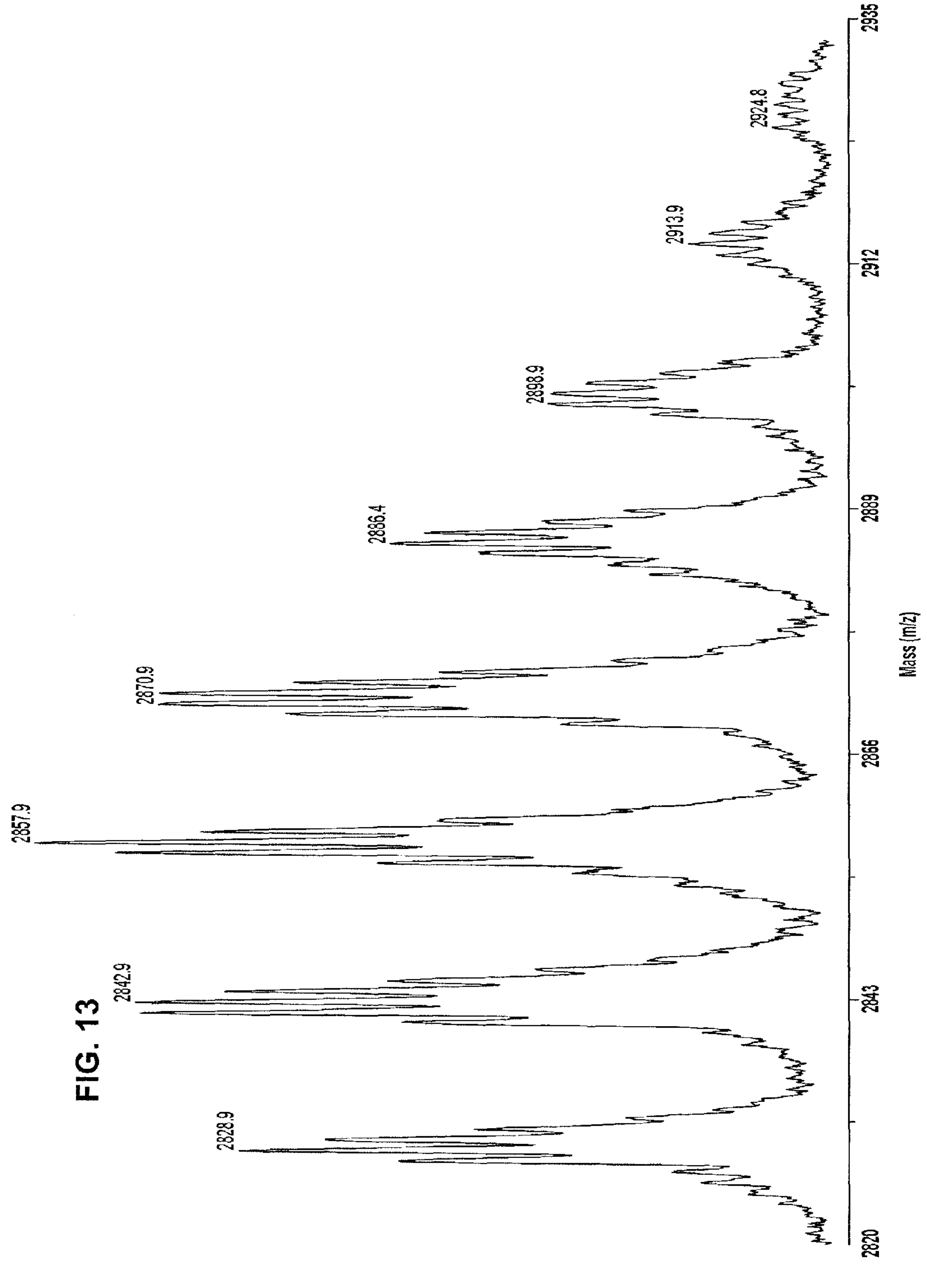
FIG. 13 shows a MALDI-TOF spectrum of crude INFA-H5-1-V5 peptide sequences (corresponding to SEQ ID NOs: 337 to 368).

FIGS. 5 and 13 are related to peptide group INFA-H5-1-V5. FIG. 5 shows an analytical HPLC chromatogram of crude INFA-H5-1-V5 peptide. FIG. 13 shows a MALDI-TOF spectrum of crude INFA-H5-1-V5 peptides.

Figure 6:
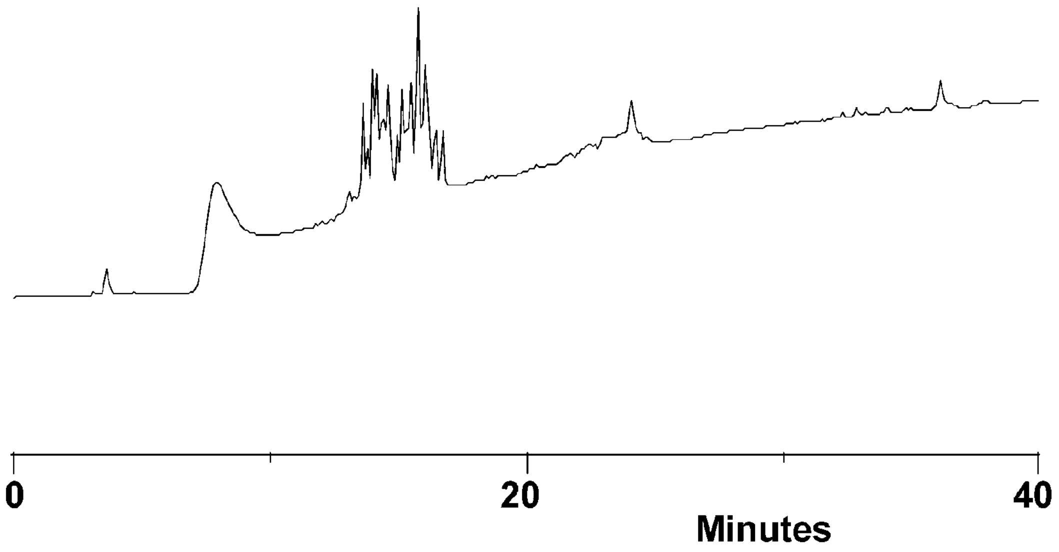
FIG. 6 shows an analytical HPLC chromatogram of crude INFA-H5-1-V6 peptide sequences (corresponding to SEQ ID NOs: 369 to 392).
Figure 14:
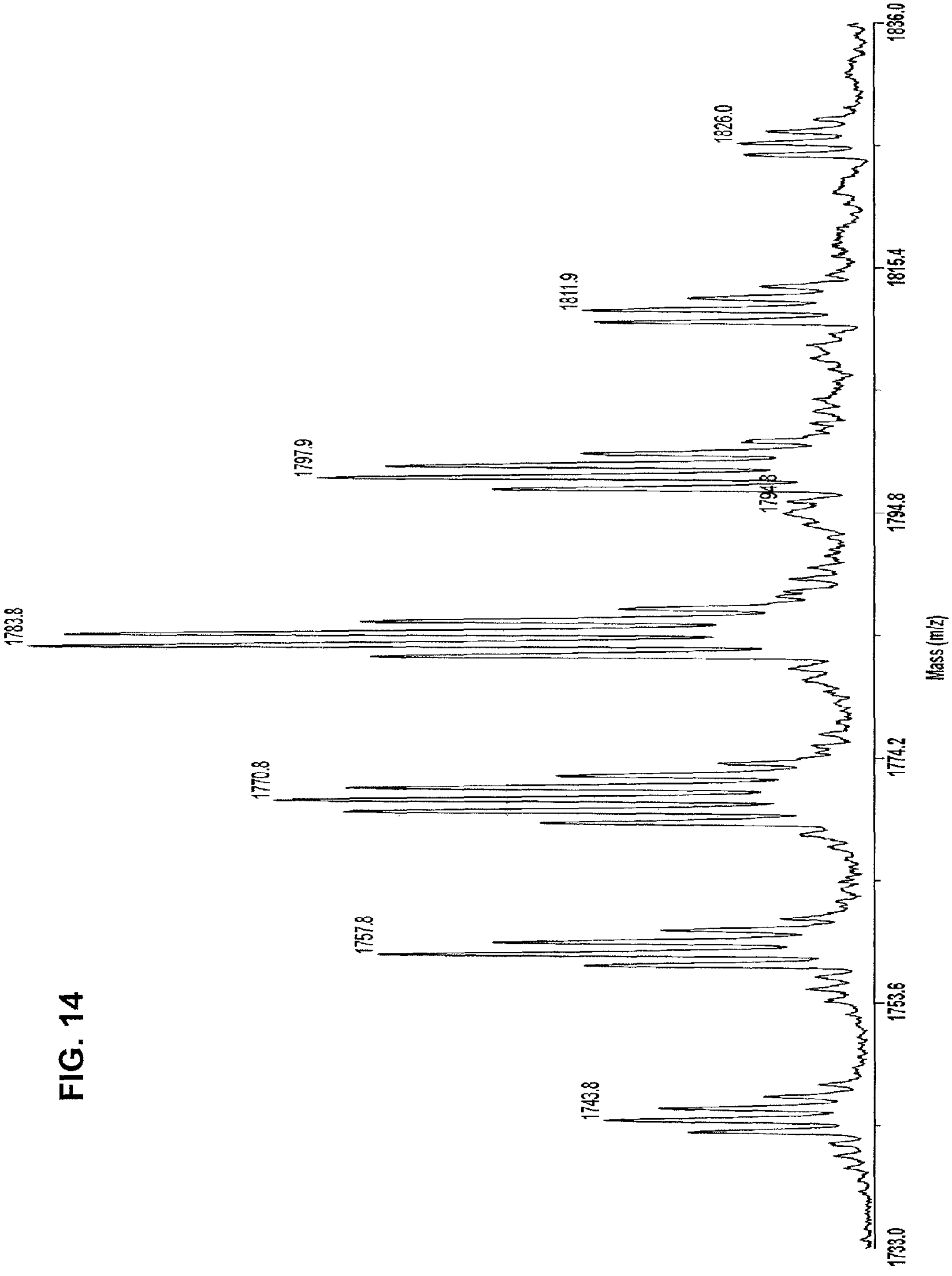
FIG. 14 shows a MALDI-TOF spectrum of crude INFA-H5-1-V6 peptide sequences (corresponding to SEQ ID NOs: 369 to 392).

FIGS. 6 and 14 are related to peptide group INFA-H5-1-V6. FIG. 6 shows an analytical HPLC chromatogram of crude INFA-H5-1-V6 peptides. FIG. 14 shows a MALDI-TOF spectrum of crude INFA-H5-1-V6 peptides.

Figure 7:
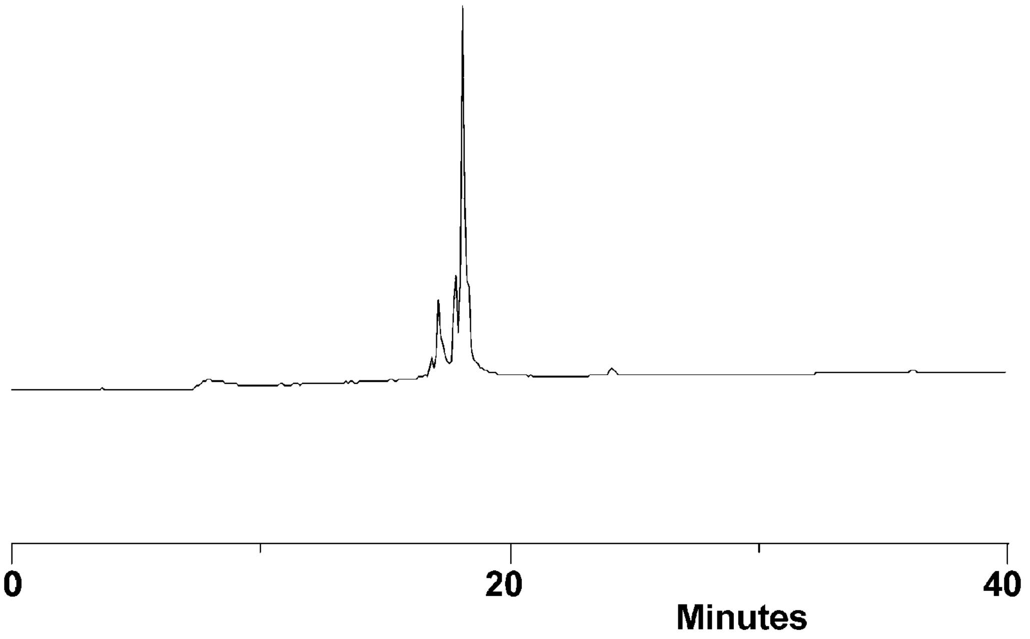
FIG. 7 shows an analytical HPLC chromatogram of crude INFA-H5-1-V7 peptide sequences (corresponding to SEQ ID NOs: 393 to 424).
Figure 15:
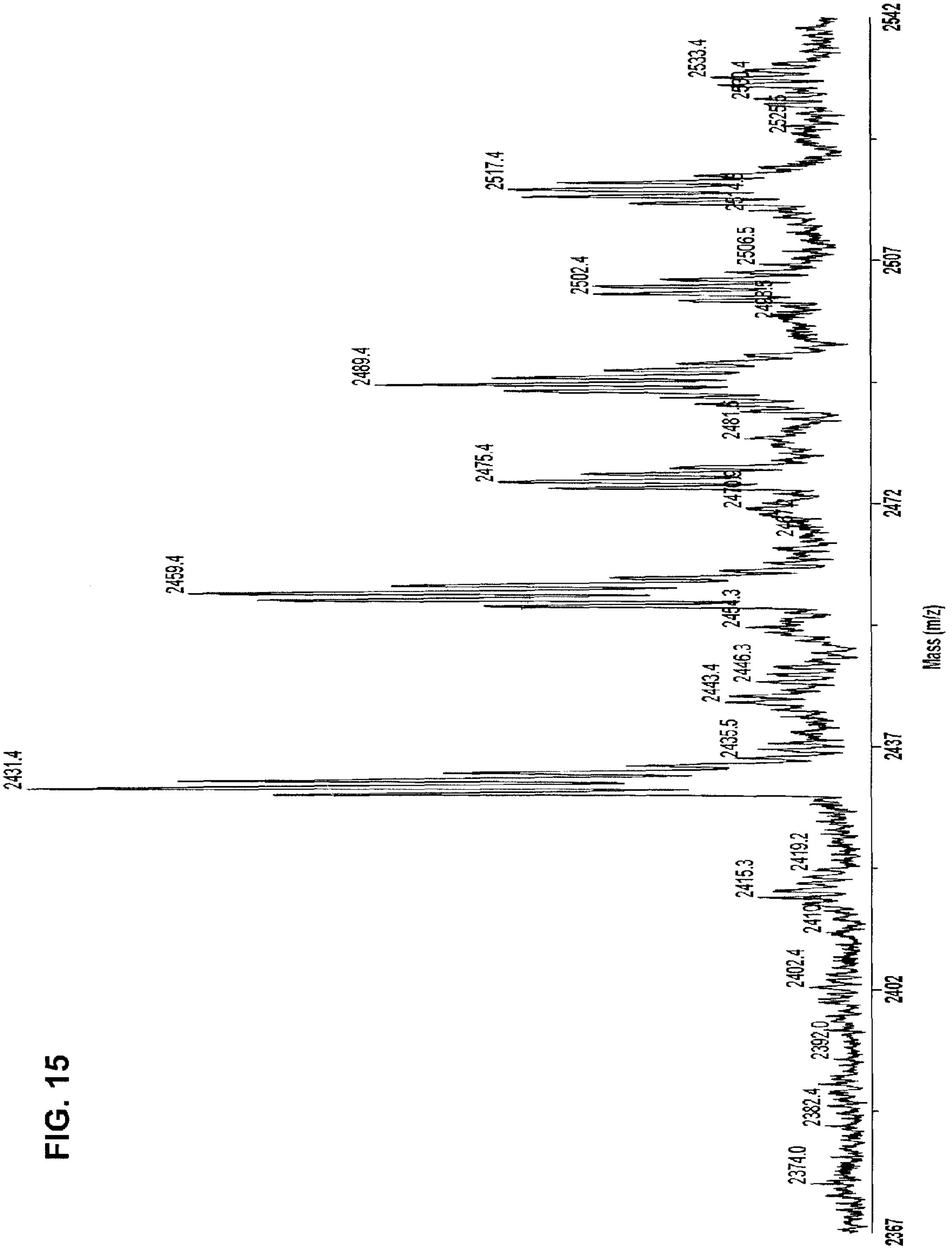
FIG. 15 shows a MALDI-TOF spectrum of crude INFA-H5-1-V7 peptide sequences (corresponding to SEQ ID NOs: 393 to 424).

FIGS. 7 and 15 are related to peptide group INFA-H5-1-V7. FIG. 7 shows an analytical HPLC chromatogram of crude INFA-H5-1-V7 peptides. FIG. 15 shows a MALDI-TOF spectrum of crude INFA-H5-1-V7 peptides.

Figure 8:
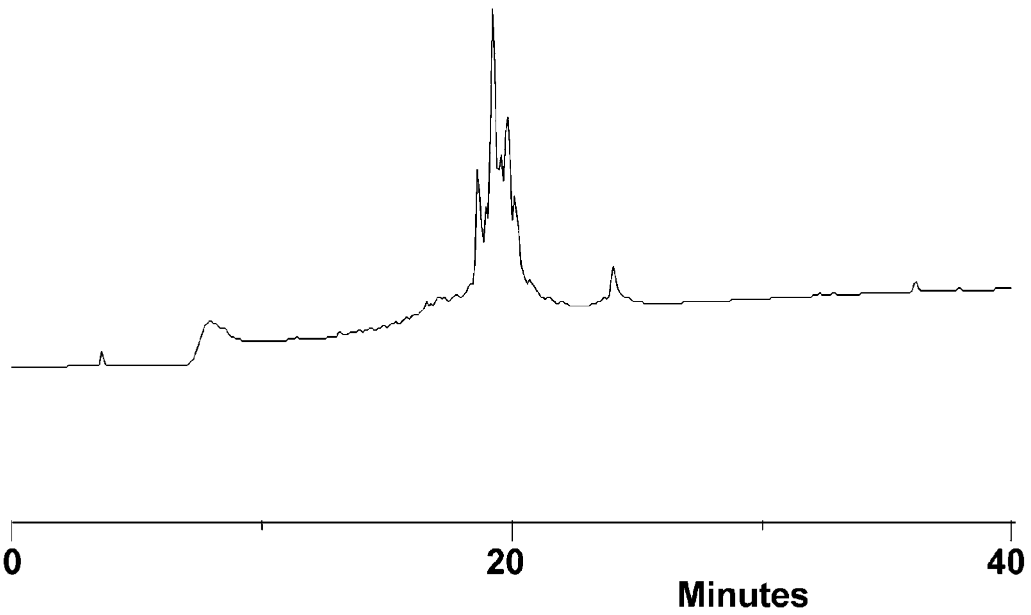
FIG. 8 shows an analytical HPLC chromatogram of crude INFA-H5-1-V8 peptide sequences (corresponding to SEQ ID NOs: 425 to 460).
Figure 16:
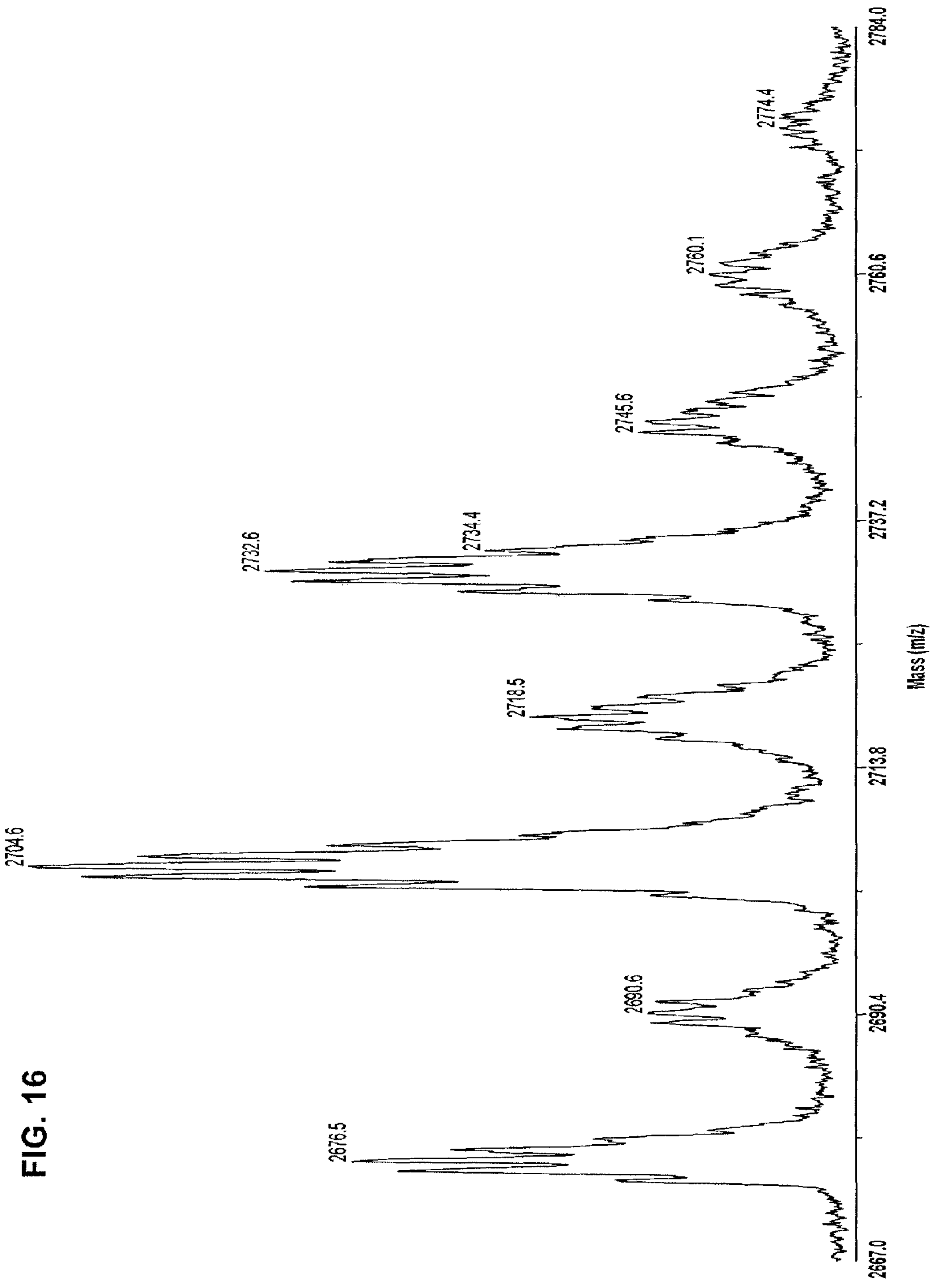
FIG. 16 shows a MALDI-TOF spectrum of crude INFA-H5-1-V8 peptide sequences (corresponding to SEQ ID NOs: 425 to 460).

FIGS. 8 and 16 are related to peptide group INFA-H5-1-V8. FIG. 8 shows an analytical HPLC chromatogram of crude INFA-H5-1-V8 peptide. FIG. 16 shows a MALDI-TOF spectrum of crude INFA-H5-1-V8 peptides.

Figure 17:
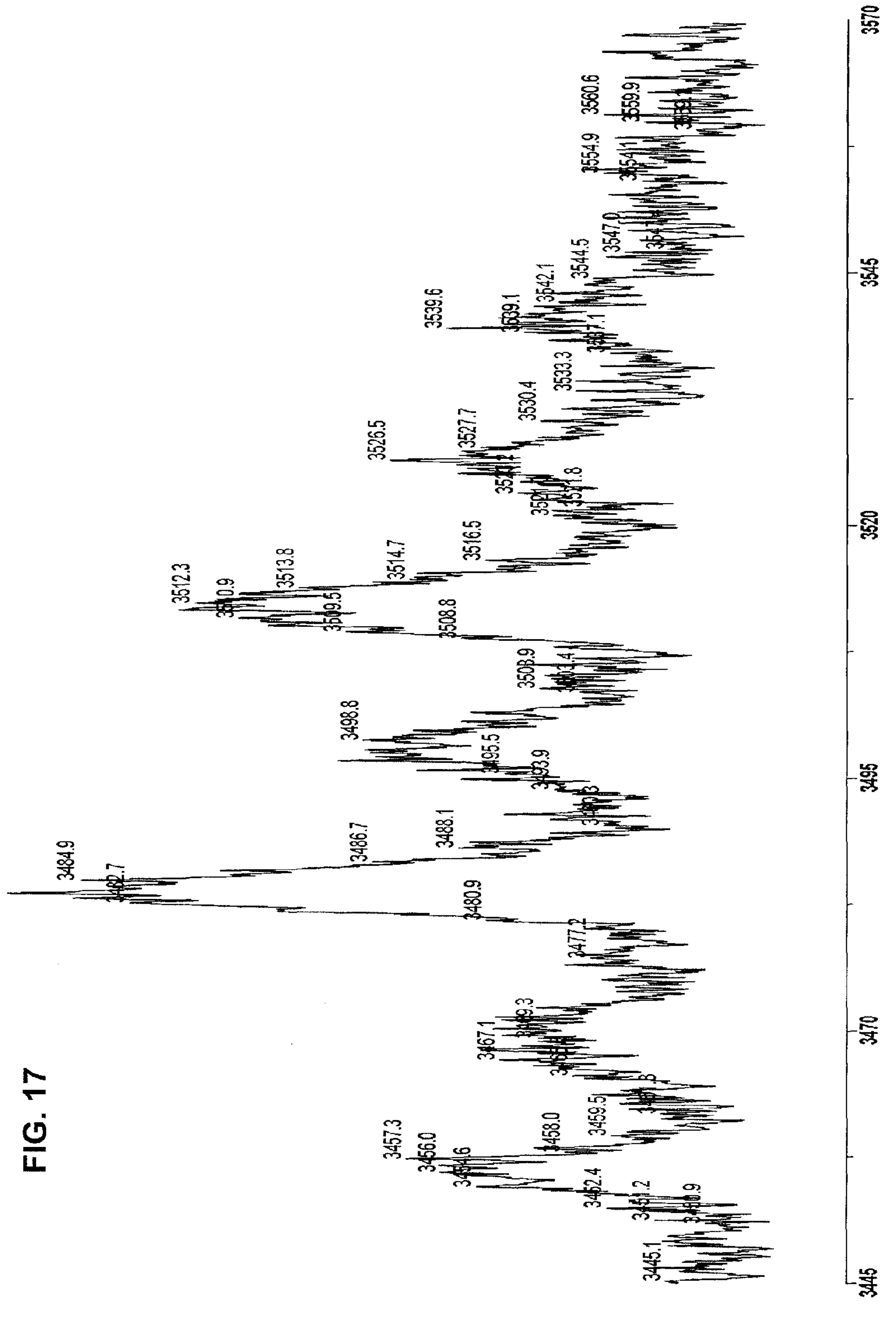
FIG. 17 shows a MALDI-TOF spectrum of crude lipidated INFA-H5-1-V8 peptide sequences (corresponding to SEQ ID NOs: 461 to 496).

FIG. 17 shows a MALDI-TOF spectrum of crude lipidated INFA-H5-1-V8 peptide sequences (corresponding to SEQ ID NOs: 213 to 248). SEQ ID NOs 213-248 are lipidated versions of SEQ ID NOs 177-212.

FIG. 18 shows the variosites of the present invention, including variable amino acid residues. FIG. 18 (*a*) shows the peptides of group INFA-H5-1-V1. FIG. 18 (*b*) shows the peptides of INFA-H5-1-V2. FIG. 18 (*c*) shows the peptides of INFA-H5-1-V3. FIG. 18 (*d*) shows the peptides of INFA-H5-1-V4. FIG. 18 (*e*) shows the peptides of INFA-H5-1-V5. FIG. 18 (*f*) shows the peptides of INFA-H5-1-V6. FIG. 18 (*g*) shows the peptides of INFA-H5-1-V7. FIG. 18 (*h*) shows the peptides of INFA-H5-1-V8.

Design of Vaccine Formulations

In the context of the present invention, a vaccine formulation is a cocktail of peptides that are used in the preparation of an influenza vaccine. The vaccine can comprise the cocktail of peptides and other substituents known in the art that would be found acceptable for inclusion. These substituents can include, but are not limited to, adjuvants, diluents and/or carriers.

As used in the present application, a peptide "analogue" can include a variant in which one or more residues are added, deleted, inserted or substituted, while having no material effect on the function of the peptide. That is, a peptide analogue in accordance with one aspect of the present invention should be capable of inducing an antibody or T-cell response to HA. A residue (or residues) may be added or deleted from either end of the peptide, deleted from within the peptide, inserted within the peptide, or substituted for one or more of the residues within the peptide. As would be understood by a person of ordinary skill in art, one or more peptide residues may be added, deleted, inserted or substituted while still maintaining the function of the peptide. For example, as many as five or more residues may be added to or removed from either end of a peptide, or inserted into a peptide, and be considered a peptide analogue within the context of the present invention. In a further example, a conservative substitution of one or more residues within a peptide may result in a peptide analogue. As would be well understood to the skilled artisan, a conservative substitution includes a substitution of one amino acid residue with another amino acid residue having one or more similar chemical properties, such as polarity, charge, hydrophobicity, or aromaticity, for example.

The vaccine formulations of the present invention are particularly suitable for preparing vaccines in the treatment of avian influenza. However, it will be appreciated that any combination of peptide sequences, or formulations comprising these peptide sequences, may be used in other influenza phenotypes.

A vaccine of the present invention may be formulated from a peptide mixture with or without variation at specific residues within each peptide. When variation is not present, the peptide formed is referred to herein as a consensus epitope. When variation is present at particular residues that are known to have different amino acids represented according to different sequences for that particular viral variant or subtype, the formulation comprises a number of peptides, collectively referred to as a variable epitope or "variosite".

Peptide vaccines can be prepared with a pool of one or more peptide sequences from SEQ ID NOs: 1 to 212 or SEQ ID NOs: 249 to 460 representing epitopes contained in the three-dimensional structure of HA. The vaccines may further comprise one or more lipidated peptides, including one or more peptides from SEQ ID NOs: 213 to 248 or SEQ ID NOs: 461 to 496. The vaccines may comprise one or more discotope constructs (peptides containing non-variable amino acid residues) or one or more discosite constructs (peptides containing variable amino acid residues). A discosite construct of the present invention is derived from one of these epitopes. Thus, a discosite construct formulation comprises one or more peptide sequences derived from the epitope containing the variable residues.

Each discosite construct of the present invention represents $2^x$ possible peptide sequences based on x varied residues. For example, a discosite construct having 3 or 4 variable residues represents $2^3=8$ or $2^4=16$ sequences, respectively. Therefore, in the context of the present invention, a discosite construct as referred to herein includes the epitope sequence containing the variable residues and the one or more possible sequences derived therefrom. It will be appreciated by the person of ordinary skill in the art that additional sequences may or may not be added as required.

The vaccine may be prepared by any methodology acceptable to one skilled in the art. For example, oligonucleotides encoding these peptides may be inserted in viral or non-viral vectors for delivery. Peptides may be synthesized individually in and mixed together to accomplish an acceptable formulation. Any variety of different modes by which these peptide antigens may be prepared is acceptable for use with the invention.

In order to formulate a vaccine that is subtype-specific, the proteins selected may contain variable regions with selected variable amino acids that are characteristic of the variability found within the subtype of interest. This allows the vaccine to be subtype specific, which may have the advantage of better representing the antigenic variation among variants within said subtype. To formulate a vaccine that has less subtype distinctiveness, the final peptide formulation may comprise the different subtype specific formulations. For example, a vaccine formulated against avian flu could target variable residues particular to subtype H5 sequences. A vaccine formulated against human flu could target variable residues characteristic of subtypes 1, 2 and/or 3 sequences.

In order to formulate a vaccine that is species-specific, the proteins selected may contain variable regions with selected variable amino acids that are characteristic of the variability found within the species of interest. This allows the vaccine to be species specific, which may have the advantage of better representing the antigenic variation among variants within said species. For example, a vaccine formulated against avian flu could target variable residues particular to avian H5 sequences. A vaccine formulated against human flu could target variable residues characteristic of both, human and avian H5 sequences.

As a specific example, the anti-INF vaccine may include the following isolated peptides: SEQ ID NOs: 1 to 40, SEQ ID NOs: 249 to 288, or peptide analogues thereof, in combination with a pharmaceutically acceptable carrier.

An exemplary anti-INF formulation may comprise one or more of, or all of SEQ ID NOs: 1 to 212, SEQ ID NOs. 249 to 460 or peptide analogues thereof; in combination with a pharmaceutically acceptable carrier. The formulation may also comprise one or more lipidated peptides of SEQ ID NOs: 1 to 212 or SEQ ID NOs: 249 to 460, such as, for example, one or more of SEQ ID NOs: 213 to 248 or SEQ ID NOs: 461 to 496.

Although all peptides of SEQ ID NOs: 1 to 212 or SEQ ID NOs: 249 to 460 may be used in combination as the vaccine formulation, sub-groups of these peptides could be used together according to the invention. For example, a formulation may comprise at least one peptide sequence from at least one of the following groups: a) SEQ ID NOs: 1 to 24; b) SEQ ID NOs: 25 to 40; c) SEQ ID NOs: 41 to 64; d) SEQ ID NOs: 65 to 88; e) SEQ ID NOs: 89 to 120; f) SEQ ID NOs: 121 to 144; g) SEQ ID NOs: 145 to 176, h) SEQ ID NOs: 177 to 212, i) SEQ ID NOs: 249 to 272; j) SEQ ID NOs: 273 to 288; k) SEQ ID NOs: 289 to 312; l) SEQ ID NOs: 313 to 336; m) SEQ ID NOs: 337 to 368; n) SEQ ID NOs: 369 to 392; o) SEQ ID NOs: 393 to 424; or p) SEQ ID NOs: 425 to 460. Further, a vaccine of the present invention may comprise a formulation comprising $2^n$ peptide sequences from at least one of the following groups: a) SEQ ID NOs: 1 to 24; b) SEQ ID NOs: 25 to 40; c) SEQ ID NOs: 41 to 64; d) SEQ ID NOs: 65 to 88; e) SEQ ID NOs: 89 to 120; f) SEQ ID NOs: 121 to 144; g) SEQ ID NOs: 145 to 176, h) SEQ ID NOs: 177 to 212, i) SEQ ID NOs: 249 to 272; j) SEQ ID NOs: 273 to 288; k) SEQ ID NOs: 289 to 312; l) SEQ ID NOs: 313 to 336; m) SEQ ID NOs: 337 to 368; n) SEQ ID NOs: 369 to 392; o) SEQ ID NOs: 393 to 424; or p) SEQ ID NOs: 425 to 460, wherein n is 1 to 4.

EXAMPLES

Peptide Synthesis

The peptides were synthesized by solid phase peptide synthesis (SPPS) using 9-fluoroenylmethoxycarbonyl (Fmoc) chemistry on Pioneer™ automated peptide synthesizer, utilizing pre-loaded Fmoc protected NovaSyn™ TGT resin (NovaBiochem) as described. Where variability at a given position is desired, mixture of two amino acids is placed at that position. This is repeated each time during the synthesis wherever the variability is desired. While 1M solution of 2-(1H-Benzotriazole-1-yl)-1, 1,3,3-tetramethyluronium tetrafluoroborate (TBTU) and N-Hydroxybenzotriazole (HOBt) in dimethylformamide (DMF), and 1 M solution of diisopropylethyl amine (DIPEA) in OMF was used for coupling amino acids, 20% piperidine in DMF was used for deblocking amino acids during the synthesis. Coupling was allowed to occur for one hour at room temperature. After the last amino acid was coupled, the resin was taken out from synthesizer and washed on a sintered glass funnel several times with OMF, with 2-propanol and with dichloromethylene (DCM), and dried under high vacuum. The peptide mixtures are cleaved and deprotected by the addition of a solution containing TFA/water/phenol/thioanisole/EDT/TIS [82:5:5:5:2:1]. The resin was incubated at room temperature for 4 hours. Cleavage mixture was then filtered under reduced pressure into a flask containing a 10-fold volume of cold ether. Resin was also rinsed twice with TFA into the same ether solution. Following incubation for 30 minutes in a freezer to further assist precipitation, the sample was centrifuged at 1,000×g for 5 minutes, and the ether removed. This extraction process was repeated three times. Following a final ether extraction, the residual organic solvent was evaporated under nitrogen gas, and the peptide mixture was redissolved in water and purified by using high performance liquid chromatography (HPLC). Excess of the solvent was removed by using a rotor evaporator, and finally lyophilized to dry powder. Mass spectrometry and amino acid analysis were performed on all the Discotopes to ensure that they have the appropriate peptide content.

Lipidation is performed as follows. Upon completion of the synthesis of a mixed peptide formulation on the synthesiser, the resin is removed from the column and placed into a vial. Dissolve 10 eq. of the Palmitic Acid, 10 eq. of TBTU and 10 eq. HOBT (all relative to the resin) in DMF (10 ml/0.1 mmol resin). Add the solution to the peptidyl resin in the vial. Add 20 eq. (relative to the resin) of the DIPEA. Adjust pH to 8-9 by adding DIPEA drop-wise. Seal the vial with a screw cap and shake the mixture overnight (at least 12 hours).

Vaccine Efficacy

Vaccine formulations comprising the peptide sequences of the present invention were tested in mice. The vaccines used are as follows:

INF-01P consists of two variosites INFA-H5-1-V1 and INFA-H5-1-V2 (SEQ ID NOs: 249-288), also referred as AviFlu-2(Montanide).

INF-02P consists of 8 variosites INFA-H5-1-V1 to INFA-H5-1-V8 (SEQ ID NOs: 249-460), also referred as AviFlu-8 (Montanide), AviFlu(Montanide), AviFlu(Alum).

INF-02L consist of 9 variosites INFA-H5-1-V1 to INFA-H5-1-V8L (SEQ ID NOs: 249-496), also referred as AviFlu (Lipidated), AviFlu(Lipidated/Alum).

Figure 19:
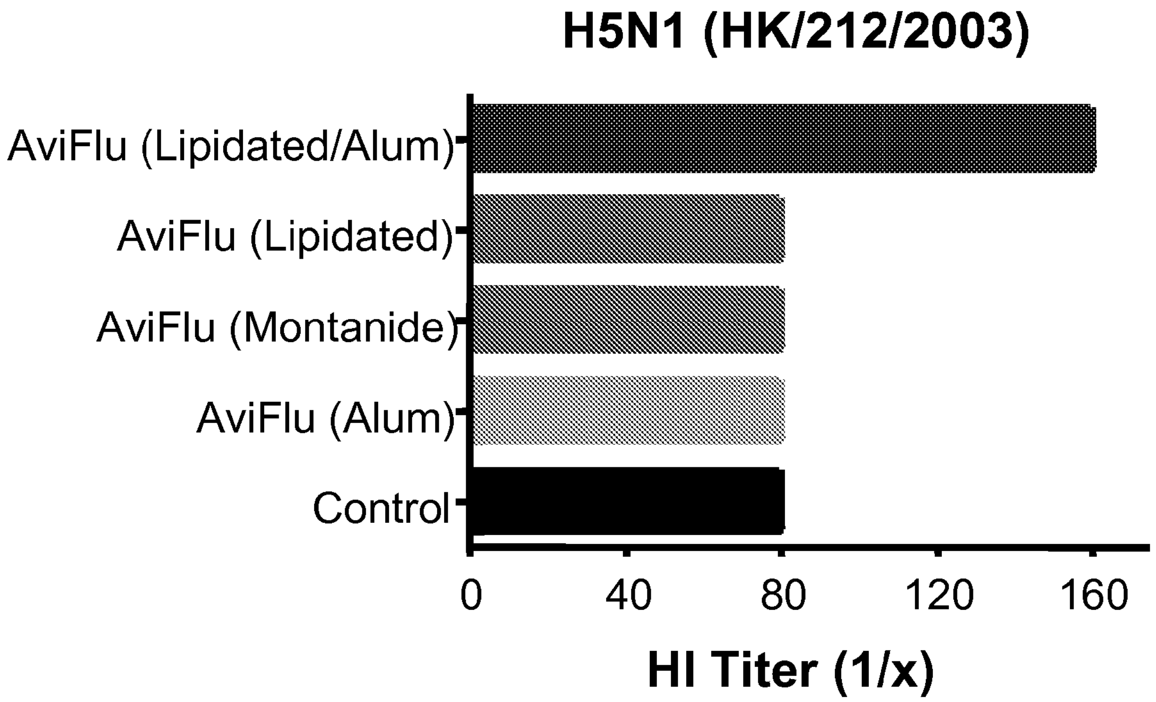
FIG. 19 illustrates induction of humoral immunity by a vaccine of the present invention after immunization. Blue bar (top bar)=AviFlu vaccine INFA-02L+alum; Red bar (2$^{nd}$ bar from top)=AviFlu vaccine INFA-02L without adjuvant; Purple bar (middle bar)=AviFlu vaccine INFA-02P+montanide; Green bar (2$^{nd}$ bar from bottom)=AviFlu vaccine INFA-02P+alum; Black bar (bottom bar)=control.

FIG. 19 illustrates induction of humoral immunity by a vaccine of the present invention after immunization.

Figure 20:
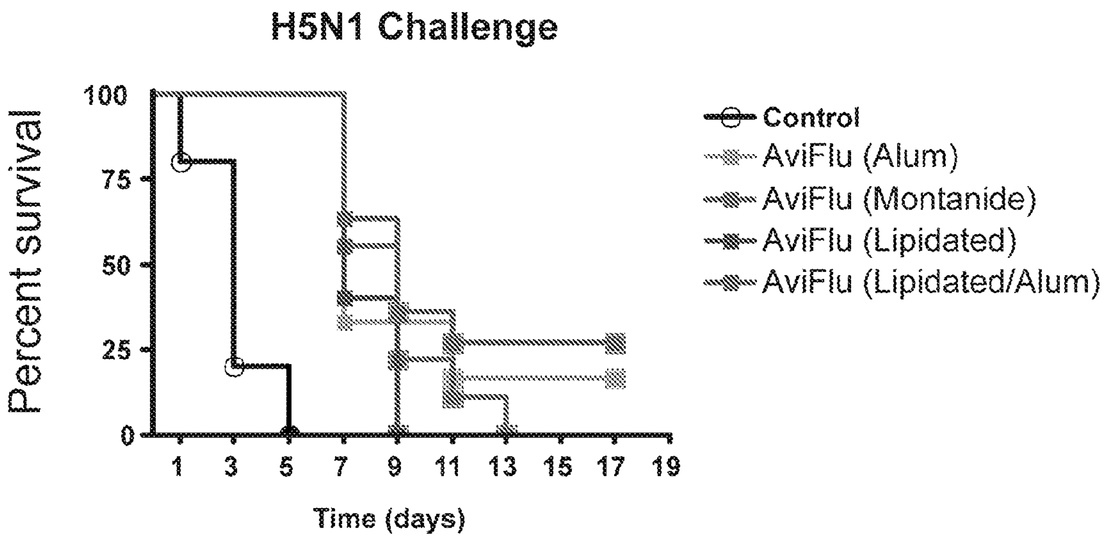
FIG. 20 illustrates a survival plot of vaccinated mice against challenge with H5N1. Legend from top: Black=control; Green=INFA-02P+alum; Purple=INFA-02P+montanide; Red=INFA-02L without adjuvant; Blue=INFA-02L+alum.

FIG. 20 illustrates a survival plot of mice vaccinated with a vaccine of the present invention against challenge with H5N1.

Figure 21:
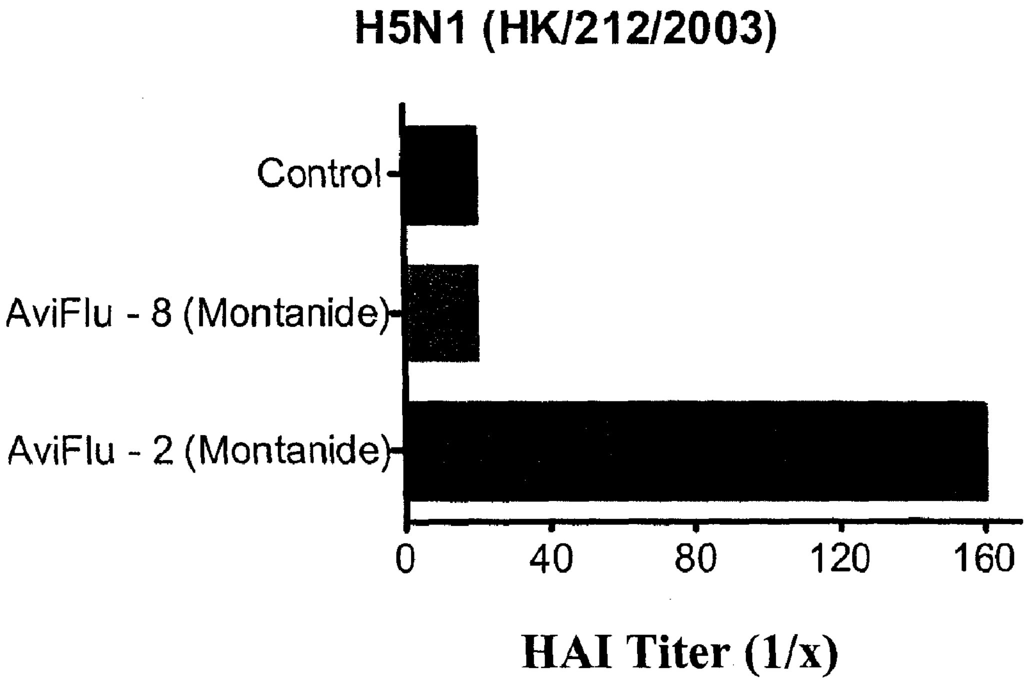
FIG. 21 shows induction of humoral immunity by INFA-01 P (INFA-HA-1-(V1-V2)) versus INFA-02P (INFA-HA-1-(V1-V8)) after vaccination in mice as measured by HA1 titres. Blue bar (bottom bar)=INFA-01 P+montanide; Purple bar (middle bar)=INFA-02P+montanide; Black bar (top bar)=control.

FIG. 21 shows induction of humoral immunity by INFA-01P (INFA-HA-1-(V1-V2)) versus INFA-02P (INFA-HA-1-(V1-V8)) after vaccination in mice as measured by HA1 titres.

Figure 22:
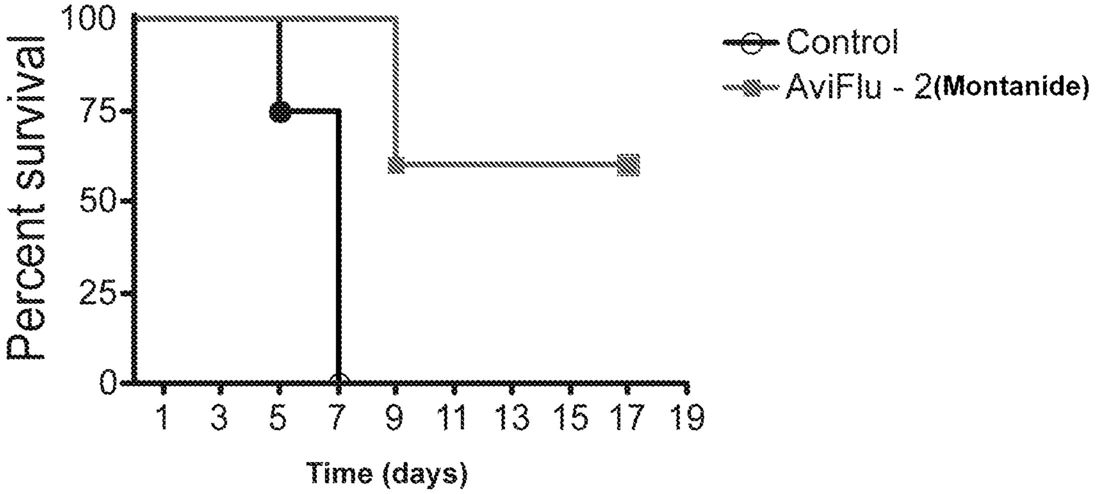
FIG. 22 shows a survival plot of mice, vaccinated by INFA-01 P (INFA-HA-1-(V1-V2)), against challenge with H5N1. Legend from top: Black=control; Blue—INFA-01P+montanide.

FIG. 22 shows a survival plot of mice, vaccinated by INFA-01P (INFA-HA-1-(V1-V2)), against challenge with H5N1.

The above-described embodiments of the present invention are intended to be examples only. Alterations, modifications and variations may be effected to the particular embodiments by those of skill in the art without departing from the scope of the invention, which is defined solely by the claims appended hereto.

REFERENCES

1. Philpott, M. et al., *Journal of virology* (1990), 64(6), 2941-2947.
2. Kaverin, N. et al., *Journal of General Virology* (2002), 83, 2497-2505.
3. Hioe, C. et al., *Journal of Virology* (1990), 64(12), 6246-6251.
4. Ha, Y. et al., *Proceedings of the National Academy of Sciences, USA* (2001), 98, 11181-11186.
5. Macken, C. et al., "The value of a database in surveillance and vaccine selection." in *Options for the Control of Influenza IV*. A. D. M. E. Osterhaus, N. Cox & A. W. Hampson (Eds.) Amsterdam: Elsevier Science, 2001, 103-106.

What is claimed is:

1. A peptide-based immunogenic composition comprising a peptide which is SEQ ID NO: 1.

2. The composition of claim 1 further comprising at least one peptide selected from the group consisting of SEQ ID NOs: 2 to 24.

3. The composition of claim 1 further comprising a pharmaceutically-acceptable diluent or carrier.

4. The composition of claim 3 further comprising an adjuvant.

5. The composition of claim 4 wherein the adjuvant is alum.

6. An immunogenic composition comprising a mixture of isolated peptides selected from the group consisting of SEQ ID NOs: 1 to 24, said peptides representing variants of at least one variable region of an avian influenza virus HA or HA1 protein, wherein each of said variable regions comprises one or more variable amino acid residues, at least one of said variable amino acid residues is represented by two or more amino acids.

7. The immunogenic composition of claim 6, wherein said one or more variable amino acid residues is represented by three or more amino acids.

8. The immunogenic composition of claim 6, further comprising a peptide selected from the group consisting of SEQ ID NOs: 25 to 40.

9. The composition of claim 1, further comprising a peptide selected from the group consisting of SEQ ID NOs: 25 to 40.

10. The composition of claim 1, comprising peptides of SEQ ID NOs: 1 to 24.

11. The composition of claim 1, comprising peptides of SEQ ID NOs: 1 to 40.

* * * * *

UNITED STATES PATENT AND TRADEMARK OFFICE

CERTIFICATE OF CORRECTION

PATENT NO. : 7,807,173 B2
APPLICATION NO. : 11/948505
DATED : October 5, 2010
INVENTOR(S) : Andrei Ogrel It is certified that error appears in the above-identified patent and that said Letters Patent is hereby corrected as shown below:

On the title page, item [56];

Foreign patent Documents, WO 2006/128294 delete “05/2007” and insert therefor -- 12/2006 --.

Signed and Sealed this
Eighteenth Day of January, 2011

David J. Kappos
*Director of the United States Patent and Trademark Office*

SEQUENCE LISTING

```
<160> NUMBER OF SEQ ID NOS: 496

<210> SEQ ID NO 1
<211> LENGTH: 21
<212> TYPE: PRT
<213> ORGANISM: Influenza A virus

<400> SEQUENCE: 1

Asn His Glu Ala Ser Ser Gly Val Ser Ser Ala Ser Pro Tyr Gln Gly
1               5                   10                  15

Lys Ser Ser Phe Phe
            20


<210> SEQ ID NO 2
<211> LENGTH: 21
<212> TYPE: PRT
<213> ORGANISM: Influenza A virus

<400> SEQUENCE: 2

Asn His Glu Ala Ser Ser Gly Val Ser Ser Ala Ser Pro Tyr Asn Gly
1               5                   10                  15

Lys Ser Ser Phe Phe
            20
```

-continued

<210> SEQ ID NO 3
<211> LENGTH: 21
<212> TYPE: PRT
<213> ORGANISM: Influenza A virus

<400> SEQUENCE: 3

```
Asn His Glu Ala Ser Ser Gly Val Ser Ser Ala Ser Pro Tyr Leu Gly
1               5                   10                  15

Lys Ser Ser Phe Phe
            20
```

<210> SEQ ID NO 4
<211> LENGTH: 21
<212> TYPE: PRT
<213> ORGANISM: Influenza A virus

<400> SEQUENCE: 4

```
Asn His Glu Ala Ser Ser Gly Val Ser Ser Ala Ser Pro Tyr Gln Gly
1               5                   10                  15

Arg Ser Ser Phe Phe
            20
```

<210> SEQ ID NO 5
<211> LENGTH: 21
<212> TYPE: PRT
<213> ORGANISM: Influenza A virus

<400> SEQUENCE: 5

```
Asn His Glu Ala Ser Ser Gly Val Ser Ser Ala Ser Pro Tyr Asn Gly
1               5                   10                  15

Arg Ser Ser Phe Phe
            20
```

<210> SEQ ID NO 6
<211> LENGTH: 21
<212> TYPE: PRT
<213> ORGANISM: Influenza A virus

<400> SEQUENCE: 6

```
Asn His Glu Ala Ser Ser Gly Val Ser Ser Ala Ser Pro Tyr Leu Gly
1               5                   10                  15

Arg Ser Ser Phe Phe
            20
```

<210> SEQ ID NO 7
<211> LENGTH: 21
<212> TYPE: PRT
<213> ORGANISM: Influenza A virus

<400> SEQUENCE: 7

```
Asn His Glu Ala Ser Leu Gly Val Ser Ser Ala Ser Pro Tyr Gln Gly
1               5                   10                  15

Lys Ser Ser Phe Phe
            20
```

<210> SEQ ID NO 8
<211> LENGTH: 21
<212> TYPE: PRT
<213> ORGANISM: Influenza A virus

<400> SEQUENCE: 8

```
Asn His Glu Ala Ser Leu Gly Val Ser Ser Ala Ser Pro Tyr Asn Gly
1               5                   10                  15
```

-continued

Lys Ser Ser Phe Phe
20

<210> SEQ ID NO 9
<211> LENGTH: 21
<212> TYPE: PRT
<213> ORGANISM: Influenza A virus

<400> SEQUENCE: 9

Asn His Glu Ala Ser Leu Gly Val Ser Ser Ala Ser Pro Tyr Leu Gly
1 5 10 15

Lys Ser Ser Phe Phe
20

<210> SEQ ID NO 10
<211> LENGTH: 21
<212> TYPE: PRT
<213> ORGANISM: Influenza A virus

<400> SEQUENCE: 10

Asn His Glu Ala Ser Leu Gly Val Ser Ser Ala Ser Pro Tyr Gln Gly
1 5 10 15

Arg Ser Ser Phe Phe
20

<210> SEQ ID NO 11
<211> LENGTH: 21
<212> TYPE: PRT
<213> ORGANISM: Influenza A virus

<400> SEQUENCE: 11

Asn His Glu Ala Ser Leu Gly Val Ser Ser Ala Ser Pro Tyr Asn Gly
1 5 10 15

Arg Ser Ser Phe Phe
20

<210> SEQ ID NO 12
<211> LENGTH: 21
<212> TYPE: PRT
<213> ORGANISM: Influenza A virus

<400> SEQUENCE: 12

Asn His Glu Ala Ser Leu Gly Val Ser Ser Ala Ser Pro Tyr Leu Gly
1 5 10 15

Arg Ser Ser Phe Phe
20

<210> SEQ ID NO 13
<211> LENGTH: 21
<212> TYPE: PRT
<213> ORGANISM: Influenza A virus

<400> SEQUENCE: 13

Asn His Asp Ala Ser Ser Gly Val Ser Ser Ala Ser Pro Tyr Gln Gly
1 5 10 15

Lys Ser Ser Phe Phe
20

<210> SEQ ID NO 14
<211> LENGTH: 21
<212> TYPE: PRT
<213> ORGANISM: Influenza A virus -continued

<400> SEQUENCE: 14

Asn His Asp Ala Ser Ser Gly Val Ser Ser Ala Ser Pro Tyr Asn Gly
1 5 10 15

Lys Ser Ser Phe Phe
20

<210> SEQ ID NO 15
<211> LENGTH: 21
<212> TYPE: PRT
<213> ORGANISM: Influenza A virus

<400> SEQUENCE: 15

Asn His Asp Ala Ser Ser Gly Val Ser Ser Ala Ser Pro Tyr Leu Gly
1 5 10 15

Lys Ser Ser Phe Phe
20

<210> SEQ ID NO 16
<211> LENGTH: 21
<212> TYPE: PRT
<213> ORGANISM: Influenza A virus

<400> SEQUENCE: 16

Asn His Asp Ala Ser Ser Gly Val Ser Ser Ala Ser Pro Tyr Gln Gly
1 5 10 15

Arg Ser Ser Phe Phe
20

<210> SEQ ID NO 17
<211> LENGTH: 21
<212> TYPE: PRT
<213> ORGANISM: Influenza A virus

<400> SEQUENCE: 17

Asn His Asp Ala Ser Ser Gly Val Ser Ser Ala Ser Pro Tyr Asn Gly
1 5 10 15

Arg Ser Ser Phe Phe
20

<210> SEQ ID NO 18
<211> LENGTH: 21
<212> TYPE: PRT
<213> ORGANISM: Influenza A virus

<400> SEQUENCE: 18

Asn His Asp Ala Ser Ser Gly Val Ser Ser Ala Ser Pro Tyr Leu Gly
1 5 10 15

Arg Ser Ser Phe Phe
20

<210> SEQ ID NO 19
<211> LENGTH: 21
<212> TYPE: PRT
<213> ORGANISM: Influenza A virus

<400> SEQUENCE: 19

Asn His Asp Ala Ser Leu Gly Val Ser Ser Ala Ser Pro Tyr Gln Gly
1 5 10 15

Lys Ser Ser Phe Phe
20

-continued

<210> SEQ ID NO 20
<211> LENGTH: 21
<212> TYPE: PRT
<213> ORGANISM: Influenza A virus

<400> SEQUENCE: 20

Asn His Asp Ala Ser Leu Gly Val Ser Ser Ala Ser Pro Tyr Asn Gly
1 5 10 15

Lys Ser Ser Phe Phe
20

<210> SEQ ID NO 21
<211> LENGTH: 21
<212> TYPE: PRT
<213> ORGANISM: Influenza A virus

<400> SEQUENCE: 21

Asn His Asp Ala Ser Leu Gly Val Ser Ser Ala Ser Pro Tyr Leu Gly
1 5 10 15

Lys Ser Ser Phe Phe
20

<210> SEQ ID NO 22
<211> LENGTH: 21
<212> TYPE: PRT
<213> ORGANISM: Influenza A virus

<400> SEQUENCE: 22

Asn His Asp Ala Ser Leu Gly Val Ser Ser Ala Ser Pro Tyr Gln Gly
1 5 10 15

Arg Ser Ser Phe Phe
20

<210> SEQ ID NO 23
<211> LENGTH: 21
<212> TYPE: PRT
<213> ORGANISM: Influenza A virus

<400> SEQUENCE: 23

Asn His Asp Ala Ser Leu Gly Val Ser Ser Ala Ser Pro Tyr Asn Gly
1 5 10 15

Arg Ser Ser Phe Phe
20

<210> SEQ ID NO 24
<211> LENGTH: 21
<212> TYPE: PRT
<213> ORGANISM: Influenza A virus

<400> SEQUENCE: 24

Asn His Asp Ala Ser Leu Gly Val Ser Ser Ala Ser Pro Tyr Leu Gly
1 5 10 15

Arg Ser Ser Phe Phe
20

<210> SEQ ID NO 25
<211> LENGTH: 17
<212> TYPE: PRT
<213> ORGANISM: Influenza A virus

<400> SEQUENCE: 25

Pro Asn Asp Ala Ala Glu Gln Thr Lys Leu Tyr Gln Asn Pro Thr Thr

-continued

```
1               5                   10                  15

Tyr


<210> SEQ ID NO 26
<211> LENGTH: 17
<212> TYPE: PRT
<213> ORGANISM: Influenza A virus

<400> SEQUENCE: 26

Pro Asn Asp Ala Ala Glu Gln Thr Lys Leu Tyr Gln Asn Pro Asn Thr
1               5                   10                  15

Tyr


<210> SEQ ID NO 27
<211> LENGTH: 17
<212> TYPE: PRT
<213> ORGANISM: Influenza A virus

<400> SEQUENCE: 27

Pro Asn Asp Ala Ala Glu Gln Thr Lys Leu Tyr Gln Asn Ser Thr Thr
1               5                   10                  15

Tyr


<210> SEQ ID NO 28
<211> LENGTH: 17
<212> TYPE: PRT
<213> ORGANISM: Influenza A virus

<400> SEQUENCE: 28

Pro Asn Asp Ala Ala Glu Gln Thr Lys Leu Tyr Gln Asn Ser Asn Thr
1               5                   10                  15

Tyr


<210> SEQ ID NO 29
<211> LENGTH: 17
<212> TYPE: PRT
<213> ORGANISM: Influenza A virus

<400> SEQUENCE: 29

Pro Asn Asp Ala Ala Glu Gln Thr Arg Leu Tyr Gln Asn Pro Thr Thr
1               5                   10                  15

Tyr


<210> SEQ ID NO 30
<211> LENGTH: 17
<212> TYPE: PRT
<213> ORGANISM: Influenza A virus

<400> SEQUENCE: 30

Pro Asn Asp Ala Ala Glu Gln Thr Arg Leu Tyr Gln Asn Pro Asn Thr
1               5                   10                  15

Tyr


<210> SEQ ID NO 31
<211> LENGTH: 17
<212> TYPE: PRT
<213> ORGANISM: Influenza A virus

<400> SEQUENCE: 31

Pro Asn Asp Ala Ala Glu Gln Thr Arg Leu Tyr Gln Asn Ser Thr Thr
1               5                   10                  15
```

-continued

Tyr

<210> SEQ ID NO 32
<211> LENGTH: 17
<212> TYPE: PRT
<213> ORGANISM: Influenza A virus

<400> SEQUENCE: 32

Pro Asn Asp Ala Ala Glu Gln Thr Arg Leu Tyr Gln Asn Ser Asn Thr
1 5 10 15

Tyr

<210> SEQ ID NO 33
<211> LENGTH: 17
<212> TYPE: PRT
<213> ORGANISM: Influenza A virus

<400> SEQUENCE: 33

Pro Asn Asp Ala Ala Glu Gln Ile Lys Leu Tyr Gln Asn Pro Thr Thr
1 5 10 15

Tyr

<210> SEQ ID NO 34
<211> LENGTH: 17
<212> TYPE: PRT
<213> ORGANISM: Influenza A virus

<400> SEQUENCE: 34

Pro Asn Asp Ala Ala Glu Gln Ile Lys Leu Tyr Gln Asn Pro Asn Thr
1 5 10 15

Tyr

<210> SEQ ID NO 35
<211> LENGTH: 17
<212> TYPE: PRT
<213> ORGANISM: Influenza A virus

<400> SEQUENCE: 35

Pro Asn Asp Ala Ala Glu Gln Ile Lys Leu Tyr Gln Asn Ser Thr Thr
1 5 10 15

Tyr

<210> SEQ ID NO 36
<211> LENGTH: 17
<212> TYPE: PRT
<213> ORGANISM: Influenza A virus

<400> SEQUENCE: 36

Pro Asn Asp Ala Ala Glu Gln Ile Lys Leu Tyr Gln Asn Ser Asn Thr
1 5 10 15

Tyr

<210> SEQ ID NO 37
<211> LENGTH: 17
<212> TYPE: PRT
<213> ORGANISM: Influenza A virus

<400> SEQUENCE: 37

Pro Asn Asp Ala Ala Glu Gln Ile Arg Leu Tyr Gln Asn Pro Thr Thr
1 5 10 15

-continued

Tyr

<210> SEQ ID NO 38
<211> LENGTH: 17
<212> TYPE: PRT
<213> ORGANISM: Influenza A virus

<400> SEQUENCE: 38

Pro Asn Asp Ala Ala Glu Gln Ile Arg Leu Tyr Gln Asn Pro Asn Thr
1               5                   10                  15

Tyr

<210> SEQ ID NO 39
<211> LENGTH: 17
<212> TYPE: PRT
<213> ORGANISM: Influenza A virus

<400> SEQUENCE: 39

Pro Asn Asp Ala Ala Glu Gln Ile Arg Leu Tyr Gln Asn Ser Thr Thr
1               5                   10                  15

Tyr

<210> SEQ ID NO 40
<211> LENGTH: 17
<212> TYPE: PRT
<213> ORGANISM: Influenza A virus

<400> SEQUENCE: 40

Pro Asn Asp Ala Ala Glu Gln Ile Arg Leu Tyr Gln Asn Ser Asn Thr
1               5                   10                  15

Tyr

<210> SEQ ID NO 41
<211> LENGTH: 18
<212> TYPE: PRT
<213> ORGANISM: Influenza A virus

<400> SEQUENCE: 41

Ser Trp Ser Asn His Glu Ala Ser Leu Ile Lys Lys Asn Ser Ala Tyr
1               5                   10                  15

Pro Thr

<210> SEQ ID NO 42
<211> LENGTH: 18
<212> TYPE: PRT
<213> ORGANISM: Influenza A virus

<400> SEQUENCE: 42

Ser Trp Ser Asn His Glu Ala Ser Leu Ile Lys Lys Asn Ser Thr Tyr
1               5                   10                  15

Pro Thr

<210> SEQ ID NO 43
<211> LENGTH: 18
<212> TYPE: PRT
<213> ORGANISM: Influenza A virus

<400> SEQUENCE: 43

Ser Trp Ser Asn His Glu Ala Ser Leu Ile Lys Lys Asn Ser Val Tyr
1               5                   10                  15

Pro Thr

-continued

<210> SEQ ID NO 44
<211> LENGTH: 18
<212> TYPE: PRT
<213> ORGANISM: Influenza A virus

<400> SEQUENCE: 44

Ser Trp Ser Asn His Glu Ala Ser Leu Ile Lys Lys Asn Asn Ala Tyr
1 5 10 15

Pro Thr

<210> SEQ ID NO 45
<211> LENGTH: 18
<212> TYPE: PRT
<213> ORGANISM: Influenza A virus

<400> SEQUENCE: 45

Ser Trp Ser Asn His Glu Ala Ser Leu Ile Lys Lys Asn Asn Thr Tyr
1 5 10 15

Pro Thr

<210> SEQ ID NO 46
<211> LENGTH: 18
<212> TYPE: PRT
<213> ORGANISM: Influenza A virus

<400> SEQUENCE: 46

Ser Trp Ser Asn His Glu Ala Ser Leu Ile Lys Lys Asn Asn Val Tyr
1 5 10 15

Pro Thr

<210> SEQ ID NO 47
<211> LENGTH: 18
<212> TYPE: PRT
<213> ORGANISM: Influenza A virus

<400> SEQUENCE: 47

Ser Trp Ser Asn His Asp Ala Ser Leu Ile Lys Lys Asn Ser Ala Tyr
1 5 10 15

Pro Thr

<210> SEQ ID NO 48
<211> LENGTH: 18
<212> TYPE: PRT
<213> ORGANISM: Influenza A virus

<400> SEQUENCE: 48

Ser Trp Ser Asn His Asp Ala Ser Leu Ile Lys Lys Asn Ser Thr Tyr
1 5 10 15

Pro Thr

<210> SEQ ID NO 49
<211> LENGTH: 18
<212> TYPE: PRT
<213> ORGANISM: Influenza A virus

<400> SEQUENCE: 49

Ser Trp Ser Asn His Asp Ala Ser Leu Ile Lys Lys Asn Ser Val Tyr
1 5 10 15

Pro Thr

-continued

<210> SEQ ID NO 50
<211> LENGTH: 18
<212> TYPE: PRT
<213> ORGANISM: Influenza A virus

<400> SEQUENCE: 50

Ser Trp Ser Asn His Asp Ala Ser Leu Ile Lys Lys Asn Asn Ala Tyr
1 5 10 15

Pro Thr

<210> SEQ ID NO 51
<211> LENGTH: 18
<212> TYPE: PRT
<213> ORGANISM: Influenza A virus

<400> SEQUENCE: 51

Ser Trp Ser Asn His Asp Ala Ser Leu Ile Lys Lys Asn Asn Thr Tyr
1 5 10 15

Pro Thr

<210> SEQ ID NO 52
<211> LENGTH: 18
<212> TYPE: PRT
<213> ORGANISM: Influenza A virus

<400> SEQUENCE: 52

Ser Trp Ser Asn His Asp Ala Ser Leu Ile Lys Lys Asn Asn Val Tyr
1 5 10 15

Pro Thr

<210> SEQ ID NO 53
<211> LENGTH: 18
<212> TYPE: PRT
<213> ORGANISM: Influenza A virus

<400> SEQUENCE: 53

Ser Trp Ser Ser His Glu Ala Ser Leu Ile Lys Lys Asn Ser Ala Tyr
1 5 10 15

Pro Thr

<210> SEQ ID NO 54
<211> LENGTH: 18
<212> TYPE: PRT
<213> ORGANISM: Influenza A virus

<400> SEQUENCE: 54

Ser Trp Ser Ser His Glu Ala Ser Leu Ile Lys Lys Asn Ser Thr Tyr
1 5 10 15

Pro Thr

<210> SEQ ID NO 55
<211> LENGTH: 18
<212> TYPE: PRT
<213> ORGANISM: Influenza A virus

<400> SEQUENCE: 55

Ser Trp Ser Ser His Glu Ala Ser Leu Ile Lys Lys Asn Ser Val Tyr
1 5 10 15

Pro Thr

-continued

<210> SEQ ID NO 56
<211> LENGTH: 18
<212> TYPE: PRT
<213> ORGANISM: Influenza A virus

<400> SEQUENCE: 56

```
Ser Trp Ser Ser His Glu Ala Ser Leu Ile Lys Lys Asn Asn Ala Tyr
1               5                   10                  15

Pro Thr
```

<210> SEQ ID NO 57
<211> LENGTH: 18
<212> TYPE: PRT
<213> ORGANISM: Influenza A virus

<400> SEQUENCE: 57

```
Ser Trp Ser Ser His Glu Ala Ser Leu Ile Lys Lys Asn Asn Thr Tyr
1               5                   10                  15

Pro Thr
```

<210> SEQ ID NO 58
<211> LENGTH: 18
<212> TYPE: PRT
<213> ORGANISM: Influenza A virus

<400> SEQUENCE: 58

```
Ser Trp Ser Ser His Glu Ala Ser Leu Ile Lys Lys Asn Asn Val Tyr
1               5                   10                  15

Pro Thr
```

<210> SEQ ID NO 59
<211> LENGTH: 18
<212> TYPE: PRT
<213> ORGANISM: Influenza A virus

<400> SEQUENCE: 59

```
Ser Trp Ser Ser His Asp Ala Ser Leu Ile Lys Lys Asn Ser Ala Tyr
1               5                   10                  15

Pro Thr
```

<210> SEQ ID NO 60
<211> LENGTH: 18
<212> TYPE: PRT
<213> ORGANISM: Influenza A virus

<400> SEQUENCE: 60

```
Ser Trp Ser Ser His Asp Ala Ser Leu Ile Lys Lys Asn Ser Thr Tyr
1               5                   10                  15

Pro Thr
```

<210> SEQ ID NO 61
<211> LENGTH: 18
<212> TYPE: PRT
<213> ORGANISM: Influenza A virus

<400> SEQUENCE: 61

```
Ser Trp Ser Ser His Asp Ala Ser Leu Ile Lys Lys Asn Ser Val Tyr
1               5                   10                  15

Pro Thr
```

<210> SEQ ID NO 62

-continued

<211> LENGTH: 18
<212> TYPE: PRT
<213> ORGANISM: Influenza A virus

<400> SEQUENCE: 62

Ser Trp Ser Ser His Asp Ala Ser Leu Ile Lys Lys Asn Asn Ala Tyr
1 5 10 15

Pro Thr

<210> SEQ ID NO 63
<211> LENGTH: 18
<212> TYPE: PRT
<213> ORGANISM: Influenza A virus

<400> SEQUENCE: 63

Ser Trp Ser Ser His Asp Ala Ser Leu Ile Lys Lys Asn Asn Thr Tyr
1 5 10 15

Pro Thr

<210> SEQ ID NO 64
<211> LENGTH: 18
<212> TYPE: PRT
<213> ORGANISM: Influenza A virus

<400> SEQUENCE: 64

Ser Trp Ser Ser His Asp Ala Ser Leu Ile Lys Lys Asn Asn Val Tyr
1 5 10 15

Pro Thr

<210> SEQ ID NO 65
<211> LENGTH: 23
<212> TYPE: PRT
<213> ORGANISM: Influenza A virus

<400> SEQUENCE: 65

Gly Lys Leu Ser Asp Leu Asp Gly Val Lys Pro Leu Ile Leu Leu Glu
1 5 10 15

Tyr Gly Asn Ser Asn Thr Lys
20

<210> SEQ ID NO 66
<211> LENGTH: 23
<212> TYPE: PRT
<213> ORGANISM: Influenza A virus

<400> SEQUENCE: 66

Gly Lys Leu Ser Asp Leu Lys Gly Val Lys Pro Leu Ile Leu Leu Glu
1 5 10 15

Tyr Gly Asn Ser Asn Thr Lys
20

<210> SEQ ID NO 67
<211> LENGTH: 23
<212> TYPE: PRT
<213> ORGANISM: Influenza A virus

<400> SEQUENCE: 67

Gly Lys Leu Ser Asp Leu Asn Gly Val Lys Pro Leu Ile Leu Leu Glu
1 5 10 15

Tyr Gly Asn Ser Asn Thr Lys
20

-continued

<210> SEQ ID NO 68
<211> LENGTH: 23
<212> TYPE: PRT
<213> ORGANISM: Influenza A virus

<400> SEQUENCE: 68

Gly Lys Leu Ser Asp Leu Asp Gly Val Lys Pro Leu Ile Leu Leu Glu
1 5 10 15

Tyr Gly Asn Ser Asn Ala Lys
20

<210> SEQ ID NO 69
<211> LENGTH: 23
<212> TYPE: PRT
<213> ORGANISM: Influenza A virus

<400> SEQUENCE: 69

Gly Lys Leu Ser Asp Leu Lys Gly Val Lys Pro Leu Ile Leu Leu Glu
1 5 10 15

Tyr Gly Asn Ser Asn Ala Lys
20

<210> SEQ ID NO 70
<211> LENGTH: 23
<212> TYPE: PRT
<213> ORGANISM: Influenza A virus

<400> SEQUENCE: 70

Gly Lys Leu Ser Asp Leu Asn Gly Val Lys Pro Leu Ile Leu Leu Glu
1 5 10 15

Tyr Gly Asn Ser Asn Ala Lys
20

<210> SEQ ID NO 71
<211> LENGTH: 23
<212> TYPE: PRT
<213> ORGANISM: Influenza A virus

<400> SEQUENCE: 71

Gly Lys Leu Ser Asp Leu Asp Gly Val Lys Pro Leu Ile Leu Leu Glu
1 5 10 15

Tyr Gly Asn Ser Asp Thr Lys
20

<210> SEQ ID NO 72
<211> LENGTH: 23
<212> TYPE: PRT
<213> ORGANISM: Influenza A virus

<400> SEQUENCE: 72

Gly Lys Leu Ser Asp Leu Lys Gly Val Lys Pro Leu Ile Leu Leu Glu
1 5 10 15

Tyr Gly Asn Ser Asp Thr Lys
20

<210> SEQ ID NO 73
<211> LENGTH: 23
<212> TYPE: PRT
<213> ORGANISM: Influenza A virus

<400> SEQUENCE: 73

Gly Lys Leu Ser Asp Leu Asn Gly Val Lys Pro Leu Ile Leu Leu Glu

-continued

```
1               5                   10                  15

Tyr Gly Asn Ser Asp Thr Lys
            20


<210> SEQ ID NO 74
<211> LENGTH: 23
<212> TYPE: PRT
<213> ORGANISM: Influenza A virus

<400> SEQUENCE: 74

Gly Lys Leu Ser Asp Leu Asp Gly Val Lys Pro Leu Ile Leu Leu Glu
1               5                   10                  15

Tyr Gly Asn Ser Asp Ala Lys
            20


<210> SEQ ID NO 75
<211> LENGTH: 23
<212> TYPE: PRT
<213> ORGANISM: Influenza A virus

<400> SEQUENCE: 75

Gly Lys Leu Ser Asp Leu Lys Gly Val Lys Pro Leu Ile Leu Leu Glu
1               5                   10                  15

Tyr Gly Asn Ser Asp Ala Lys
            20


<210> SEQ ID NO 76
<211> LENGTH: 23
<212> TYPE: PRT
<213> ORGANISM: Influenza A virus

<400> SEQUENCE: 76

Gly Lys Leu Ser Asp Leu Asn Gly Val Lys Pro Leu Ile Leu Leu Glu
1               5                   10                  15

Tyr Gly Asn Ser Asp Ala Lys
            20


<210> SEQ ID NO 77
<211> LENGTH: 23
<212> TYPE: PRT
<213> ORGANISM: Influenza A virus

<400> SEQUENCE: 77

Gly Lys Leu Ser Ser Leu Asp Gly Val Lys Pro Leu Ile Leu Leu Glu
1               5                   10                  15

Tyr Gly Asn Ser Asn Thr Lys
            20


<210> SEQ ID NO 78
<211> LENGTH: 23
<212> TYPE: PRT
<213> ORGANISM: Influenza A virus

<400> SEQUENCE: 78

Gly Lys Leu Ser Ser Leu Lys Gly Val Lys Pro Leu Ile Leu Leu Glu
1               5                   10                  15

Tyr Gly Asn Ser Asn Thr Lys
            20


<210> SEQ ID NO 79
<211> LENGTH: 23
<212> TYPE: PRT
```

-continued

<213> ORGANISM: Influenza A virus

<400> SEQUENCE: 79

Gly Lys Leu Ser Ser Leu Asn Gly Val Lys Pro Leu Ile Leu Leu Glu
1               5                   10                  15

Tyr Gly Asn Ser Asn Thr Lys
            20

<210> SEQ ID NO 80
<211> LENGTH: 23
<212> TYPE: PRT
<213> ORGANISM: Influenza A virus

<400> SEQUENCE: 80

Gly Lys Leu Ser Ser Leu Asp Gly Val Lys Pro Leu Ile Leu Leu Glu
1               5                   10                  15

Tyr Gly Asn Ser Asn Ala Lys
            20

<210> SEQ ID NO 81
<211> LENGTH: 23
<212> TYPE: PRT
<213> ORGANISM: Influenza A virus

<400> SEQUENCE: 81

Gly Lys Leu Ser Ser Leu Lys Gly Val Lys Pro Leu Ile Leu Leu Glu
1               5                   10                  15

Tyr Gly Asn Ser Asn Ala Lys
            20

<210> SEQ ID NO 82
<211> LENGTH: 23
<212> TYPE: PRT
<213> ORGANISM: Influenza A virus

<400> SEQUENCE: 82

Gly Lys Leu Ser Ser Leu Asn Gly Val Lys Pro Leu Ile Leu Leu Glu
1               5                   10                  15

Tyr Gly Asn Ser Asn Ala Lys
            20

<210> SEQ ID NO 83
<211> LENGTH: 23
<212> TYPE: PRT
<213> ORGANISM: Influenza A virus

<400> SEQUENCE: 83

Gly Lys Leu Ser Ser Leu Asp Gly Val Lys Pro Leu Ile Leu Leu Glu
1               5                   10                  15

Tyr Gly Asn Ser Asp Thr Lys
            20

<210> SEQ ID NO 84
<211> LENGTH: 23
<212> TYPE: PRT
<213> ORGANISM: Influenza A virus

<400> SEQUENCE: 84

Gly Lys Leu Ser Ser Leu Lys Gly Val Lys Pro Leu Ile Leu Leu Glu
1               5                   10                  15

Tyr Gly Asn Ser Asp Thr Lys
            20

-continued

<210> SEQ ID NO 85
<211> LENGTH: 23
<212> TYPE: PRT
<213> ORGANISM: Influenza A virus

<400> SEQUENCE: 85

Gly Lys Leu Ser Ser Leu Asn Gly Val Lys Pro Leu Ile Leu Leu Glu
1 5 10 15

Tyr Gly Asn Ser Asp Thr Lys
20

<210> SEQ ID NO 86
<211> LENGTH: 23
<212> TYPE: PRT
<213> ORGANISM: Influenza A virus

<400> SEQUENCE: 86

Gly Lys Leu Ser Ser Leu Asp Gly Val Lys Pro Leu Ile Leu Leu Glu
1 5 10 15

Tyr Gly Asn Ser Asp Ala Lys
20

<210> SEQ ID NO 87
<211> LENGTH: 23
<212> TYPE: PRT
<213> ORGANISM: Influenza A virus

<400> SEQUENCE: 87

Gly Lys Leu Ser Ser Leu Lys Gly Val Lys Pro Leu Ile Leu Leu Glu
1 5 10 15

Tyr Gly Asn Ser Asp Ala Lys
20

<210> SEQ ID NO 88
<211> LENGTH: 23
<212> TYPE: PRT
<213> ORGANISM: Influenza A virus

<400> SEQUENCE: 88

Gly Lys Leu Ser Ser Leu Asn Gly Val Lys Pro Leu Ile Leu Leu Glu
1 5 10 15

Tyr Gly Asn Ser Asp Ala Lys
20

<210> SEQ ID NO 89
<211> LENGTH: 24
<212> TYPE: PRT
<213> ORGANISM: Influenza A virus

<400> SEQUENCE: 89

Thr Ile Lys Arg Ser Tyr Asn Asn Thr Asn Gln Glu Asp Lys Pro Asn
1 5 10 15

Asp Ala Ile Asn Phe Glu Ser Asn
20

<210> SEQ ID NO 90
<211> LENGTH: 24
<212> TYPE: PRT
<213> ORGANISM: Influenza A virus

<400> SEQUENCE: 90

-continued

Thr Ile Lys Arg Ser Tyr Asn Asn Thr Asn Gln Glu Asp Lys Pro Asn
1 5 10 15

Asp Ala Ile Asn Phe Glu Ser Thr
20

<210> SEQ ID NO 91
<211> LENGTH: 24
<212> TYPE: PRT
<213> ORGANISM: Influenza A virus

<400> SEQUENCE: 91

Thr Ile Lys Arg Ser Tyr Asn Asn Thr Asn Gln Glu Asp Lys Pro Asn
1 5 10 15

Asp Ser Ile Asn Phe Glu Ser Asn
20

<210> SEQ ID NO 92
<211> LENGTH: 24
<212> TYPE: PRT
<213> ORGANISM: Influenza A virus

<400> SEQUENCE: 92

Thr Ile Lys Arg Ser Tyr Asn Asn Thr Asn Gln Glu Asp Lys Pro Asn
1 5 10 15

Asp Ser Ile Asn Phe Glu Ser Thr
20

<210> SEQ ID NO 93
<211> LENGTH: 24
<212> TYPE: PRT
<213> ORGANISM: Influenza A virus

<400> SEQUENCE: 93

Thr Ile Lys Arg Ser Tyr Asn Asn Thr Asn Gln Glu Asp Arg Pro Asn
1 5 10 15

Asp Ala Ile Asn Phe Glu Ser Asn
20

<210> SEQ ID NO 94
<211> LENGTH: 24
<212> TYPE: PRT
<213> ORGANISM: Influenza A virus

<400> SEQUENCE: 94

Thr Ile Lys Arg Ser Tyr Asn Asn Thr Asn Gln Glu Asp Arg Pro Asn
1 5 10 15

Asp Ala Ile Asn Phe Glu Ser Thr
20

<210> SEQ ID NO 95
<211> LENGTH: 24
<212> TYPE: PRT
<213> ORGANISM: Influenza A virus

<400> SEQUENCE: 95

Thr Ile Lys Arg Ser Tyr Asn Asn Thr Asn Gln Glu Asp Arg Pro Asn
1 5 10 15

Asp Ser Ile Asn Phe Glu Ser Asn
20

<210> SEQ ID NO 96
<211> LENGTH: 24

-continued

<212> TYPE: PRT
<213> ORGANISM: Influenza A virus

<400> SEQUENCE: 96

Thr Ile Lys Arg Ser Tyr Asn Asn Thr Asn Gln Glu Asp Arg Pro Asn
1 5 10 15

Asp Ser Ile Asn Phe Glu Ser Thr
20

<210> SEQ ID NO 97
<211> LENGTH: 24
<212> TYPE: PRT
<213> ORGANISM: Influenza A virus

<400> SEQUENCE: 97

Thr Ile Lys Arg Ser Tyr Asn Asn Thr Asn Val Glu Asp Lys Pro Asn
1 5 10 15

Asp Ala Ile Asn Phe Glu Ser Asn
20

<210> SEQ ID NO 98
<211> LENGTH: 24
<212> TYPE: PRT
<213> ORGANISM: Influenza A virus

<400> SEQUENCE: 98

Thr Ile Lys Arg Ser Tyr Asn Asn Thr Asn Val Glu Asp Lys Pro Asn
1 5 10 15

Asp Ala Ile Asn Phe Glu Ser Thr
20

<210> SEQ ID NO 99
<211> LENGTH: 24
<212> TYPE: PRT
<213> ORGANISM: Influenza A virus

<400> SEQUENCE: 99

Thr Ile Lys Arg Ser Tyr Asn Asn Thr Asn Val Glu Asp Lys Pro Asn
1 5 10 15

Asp Ser Ile Asn Phe Glu Ser Asn
20

<210> SEQ ID NO 100
<211> LENGTH: 24
<212> TYPE: PRT
<213> ORGANISM: Influenza A virus

<400> SEQUENCE: 100

Thr Ile Lys Arg Ser Tyr Asn Asn Thr Asn Val Glu Asp Lys Pro Asn
1 5 10 15

Asp Ser Ile Asn Phe Glu Ser Thr
20

<210> SEQ ID NO 101
<211> LENGTH: 24
<212> TYPE: PRT
<213> ORGANISM: Influenza A virus

<400> SEQUENCE: 101

Thr Ile Lys Arg Ser Tyr Asn Asn Thr Asn Val Glu Asp Arg Pro Asn
1 5 10 15

Asp Ala Ile Asn Phe Glu Ser Asn

20

<210> SEQ ID NO 102
<211> LENGTH: 24
<212> TYPE: PRT
<213> ORGANISM: Influenza A virus

<400> SEQUENCE: 102

Thr Ile Lys Arg Ser Tyr Asn Asn Thr Asn Val Glu Asp Arg Pro Asn
1 5 10 15

Asp Ala Ile Asn Phe Glu Ser Thr
20

<210> SEQ ID NO 103
<211> LENGTH: 24
<212> TYPE: PRT
<213> ORGANISM: Influenza A virus

<400> SEQUENCE: 103

Thr Ile Lys Arg Ser Tyr Asn Asn Thr Asn Val Glu Asp Arg Pro Asn
1 5 10 15

Asp Ser Ile Asn Phe Glu Ser Asn
20

<210> SEQ ID NO 104
<211> LENGTH: 24
<212> TYPE: PRT
<213> ORGANISM: Influenza A virus

<400> SEQUENCE: 104

Thr Ile Lys Arg Ser Tyr Asn Asn Thr Asn Val Glu Asp Arg Pro Asn
1 5 10 15

Asp Ser Ile Asn Phe Glu Ser Thr
20

<210> SEQ ID NO 105
<211> LENGTH: 24
<212> TYPE: PRT
<213> ORGANISM: Influenza A virus

<400> SEQUENCE: 105

Thr Ile Lys Arg Thr Tyr Asn Asn Thr Asn Gln Glu Asp Lys Pro Asn
1 5 10 15

Asp Ala Ile Asn Phe Glu Ser Asn
20

<210> SEQ ID NO 106
<211> LENGTH: 24
<212> TYPE: PRT
<213> ORGANISM: Influenza A virus

<400> SEQUENCE: 106

Thr Ile Lys Arg Thr Tyr Asn Asn Thr Asn Gln Glu Asp Lys Pro Asn
1 5 10 15

Asp Ala Ile Asn Phe Glu Ser Thr
20

<210> SEQ ID NO 107
<211> LENGTH: 24
<212> TYPE: PRT
<213> ORGANISM: Influenza A virus

<400> SEQUENCE: 107

-continued

```
Thr Ile Lys Arg Thr Tyr Asn Asn Thr Asn Gln Glu Asp Lys Pro Asn
1               5                   10                  15

Asp Ser Ile Asn Phe Glu Ser Asn
            20


<210> SEQ ID NO 108
<211> LENGTH: 24
<212> TYPE: PRT
<213> ORGANISM: Influenza A virus

<400> SEQUENCE: 108

Thr Ile Lys Arg Thr Tyr Asn Asn Thr Asn Gln Glu Asp Lys Pro Asn
1               5                   10                  15

Asp Ser Ile Asn Phe Glu Ser Thr
            20


<210> SEQ ID NO 109
<211> LENGTH: 24
<212> TYPE: PRT
<213> ORGANISM: Influenza A virus

<400> SEQUENCE: 109

Thr Ile Lys Arg Thr Tyr Asn Asn Thr Asn Gln Glu Asp Arg Pro Asn
1               5                   10                  15

Asp Ala Ile Asn Phe Glu Ser Asn
            20


<210> SEQ ID NO 110
<211> LENGTH: 24
<212> TYPE: PRT
<213> ORGANISM: Influenza A virus

<400> SEQUENCE: 110

Thr Ile Lys Arg Thr Tyr Asn Asn Thr Asn Gln Glu Asp Arg Pro Asn
1               5                   10                  15

Asp Ala Ile Asn Phe Glu Ser Thr
            20


<210> SEQ ID NO 111
<211> LENGTH: 24
<212> TYPE: PRT
<213> ORGANISM: Influenza A virus

<400> SEQUENCE: 111

Thr Ile Lys Arg Thr Tyr Asn Asn Thr Asn Gln Glu Asp Arg Pro Asn
1               5                   10                  15

Asp Ser Ile Asn Phe Glu Ser Asn
            20


<210> SEQ ID NO 112
<211> LENGTH: 24
<212> TYPE: PRT
<213> ORGANISM: Influenza A virus

<400> SEQUENCE: 112

Thr Ile Lys Arg Thr Tyr Asn Asn Thr Asn Gln Glu Asp Arg Pro Asn
1               5                   10                  15

Asp Ser Ile Asn Phe Glu Ser Thr
            20


<210> SEQ ID NO 113
```

-continued

<211> LENGTH: 24
<212> TYPE: PRT
<213> ORGANISM: Influenza A virus

<400> SEQUENCE: 113

Thr Ile Lys Arg Thr Tyr Asn Asn Thr Asn Val Glu Asp Lys Pro Asn
1               5                   10                  15

Asp Ala Ile Asn Phe Glu Ser Asn
            20

<210> SEQ ID NO 114
<211> LENGTH: 24
<212> TYPE: PRT
<213> ORGANISM: Influenza A virus

<400> SEQUENCE: 114

Thr Ile Lys Arg Thr Tyr Asn Asn Thr Asn Val Glu Asp Lys Pro Asn
1               5                   10                  15

Asp Ala Ile Asn Phe Glu Ser Thr
            20

<210> SEQ ID NO 115
<211> LENGTH: 24
<212> TYPE: PRT
<213> ORGANISM: Influenza A virus

<400> SEQUENCE: 115

Thr Ile Lys Arg Thr Tyr Asn Asn Thr Asn Val Glu Asp Lys Pro Asn
1               5                   10                  15

Asp Ser Ile Asn Phe Glu Ser Asn
            20

<210> SEQ ID NO 116
<211> LENGTH: 24
<212> TYPE: PRT
<213> ORGANISM: Influenza A virus

<400> SEQUENCE: 116

Thr Ile Lys Arg Thr Tyr Asn Asn Thr Asn Val Glu Asp Lys Pro Asn
1               5                   10                  15

Asp Ser Ile Asn Phe Glu Ser Thr
            20

<210> SEQ ID NO 117
<211> LENGTH: 24
<212> TYPE: PRT
<213> ORGANISM: Influenza A virus

<400> SEQUENCE: 117

Thr Ile Lys Arg Thr Tyr Asn Asn Thr Asn Val Glu Asp Arg Pro Asn
1               5                   10                  15

Asp Ala Ile Asn Phe Glu Ser Asn
            20

<210> SEQ ID NO 118
<211> LENGTH: 24
<212> TYPE: PRT
<213> ORGANISM: Influenza A virus

<400> SEQUENCE: 118

Thr Ile Lys Arg Thr Tyr Asn Asn Thr Asn Val Glu Asp Arg Pro Asn
1               5                   10                  15

-continued

```
Asp Ala Ile Asn Phe Glu Ser Thr
            20


<210> SEQ ID NO 119
<211> LENGTH: 24
<212> TYPE: PRT
<213> ORGANISM: Influenza A virus

<400> SEQUENCE: 119

Thr Ile Lys Arg Thr Tyr Asn Asn Thr Asn Val Glu Asp Arg Pro Asn
1               5                   10                  15

Asp Ser Ile Asn Phe Glu Ser Asn
            20


<210> SEQ ID NO 120
<211> LENGTH: 24
<212> TYPE: PRT
<213> ORGANISM: Influenza A virus

<400> SEQUENCE: 120

Thr Ile Lys Arg Thr Tyr Asn Asn Thr Asn Val Glu Asp Arg Pro Asn
1               5                   10                  15

Asp Ser Ile Asn Phe Glu Ser Thr
            20


<210> SEQ ID NO 121
<211> LENGTH: 16
<212> TYPE: PRT
<213> ORGANISM: Influenza A virus

<400> SEQUENCE: 121

Ile Ser Val Gly Thr Ser Thr Leu Asn Gln Arg Leu Val Pro Lys Ile
1               5                   10                  15


<210> SEQ ID NO 122
<211> LENGTH: 16
<212> TYPE: PRT
<213> ORGANISM: Influenza A virus

<400> SEQUENCE: 122

Ile Ser Val Gly Thr Ser Thr Leu Asn Gln Arg Leu Val Pro Glu Ile
1               5                   10                  15


<210> SEQ ID NO 123
<211> LENGTH: 16
<212> TYPE: PRT
<213> ORGANISM: Influenza A virus

<400> SEQUENCE: 123

Ile Ser Val Gly Thr Ser Thr Leu Asn Gln Arg Leu Val Pro Arg Ile
1               5                   10                  15


<210> SEQ ID NO 124
<211> LENGTH: 16
<212> TYPE: PRT
<213> ORGANISM: Influenza A virus

<400> SEQUENCE: 124

Ile Ser Val Gly Thr Ser Thr Leu Asn Gln Arg Leu Ile Pro Lys Ile
1               5                   10                  15


<210> SEQ ID NO 125
<211> LENGTH: 16
<212> TYPE: PRT
```

-continued

<213> ORGANISM: Influenza A virus

<400> SEQUENCE: 125

Ile Ser Val Gly Thr Ser Thr Leu Asn Gln Arg Leu Ile Pro Glu Ile
1 5 10 15

<210> SEQ ID NO 126
<211> LENGTH: 16
<212> TYPE: PRT
<213> ORGANISM: Influenza A virus

<400> SEQUENCE: 126

Ile Ser Val Gly Thr Ser Thr Leu Asn Gln Arg Leu Ile Pro Arg Ile
1 5 10 15

<210> SEQ ID NO 127
<211> LENGTH: 16
<212> TYPE: PRT
<213> ORGANISM: Influenza A virus

<400> SEQUENCE: 127

Ile Ser Val Gly Thr Ser Thr Leu Asn Gln Arg Ser Val Pro Lys Ile
1 5 10 15

<210> SEQ ID NO 128
<211> LENGTH: 16
<212> TYPE: PRT
<213> ORGANISM: Influenza A virus

<400> SEQUENCE: 128

Ile Ser Val Gly Thr Ser Thr Leu Asn Gln Arg Ser Val Pro Glu Ile
1 5 10 15

<210> SEQ ID NO 129
<211> LENGTH: 16
<212> TYPE: PRT
<213> ORGANISM: Influenza A virus

<400> SEQUENCE: 129

Ile Ser Val Gly Thr Ser Thr Leu Asn Gln Arg Ser Val Pro Arg Ile
1 5 10 15

<210> SEQ ID NO 130
<211> LENGTH: 16
<212> TYPE: PRT
<213> ORGANISM: Influenza A virus

<400> SEQUENCE: 130

Ile Ser Val Gly Thr Ser Thr Leu Asn Gln Arg Ser Ile Pro Lys Ile
1 5 10 15

<210> SEQ ID NO 131
<211> LENGTH: 16
<212> TYPE: PRT
<213> ORGANISM: Influenza A virus

<400> SEQUENCE: 131

Ile Ser Val Gly Thr Ser Thr Leu Asn Gln Arg Ser Ile Pro Glu Ile
1 5 10 15

<210> SEQ ID NO 132
<211> LENGTH: 16
<212> TYPE: PRT
<213> ORGANISM: Influenza A virus -continued

<400> SEQUENCE: 132

Ile Ser Val Gly Thr Ser Thr Leu Asn Gln Arg Ser Ile Pro Arg Ile
1 5 10 15

<210> SEQ ID NO 133
<211> LENGTH: 16
<212> TYPE: PRT
<213> ORGANISM: Influenza A virus

<400> SEQUENCE: 133

Val Ser Val Gly Thr Ser Thr Leu Asn Gln Arg Leu Val Pro Lys Ile
1 5 10 15

<210> SEQ ID NO 134
<211> LENGTH: 16
<212> TYPE: PRT
<213> ORGANISM: Influenza A virus

<400> SEQUENCE: 134

Val Ser Val Gly Thr Ser Thr Leu Asn Gln Arg Leu Val Pro Glu Ile
1 5 10 15

<210> SEQ ID NO 135
<211> LENGTH: 16
<212> TYPE: PRT
<213> ORGANISM: Influenza A virus

<400> SEQUENCE: 135

Val Ser Val Gly Thr Ser Thr Leu Asn Gln Arg Leu Val Pro Arg Ile
1 5 10 15

<210> SEQ ID NO 136
<211> LENGTH: 16
<212> TYPE: PRT
<213> ORGANISM: Influenza A virus

<400> SEQUENCE: 136

Val Ser Val Gly Thr Ser Thr Leu Asn Gln Arg Leu Ile Pro Lys Ile
1 5 10 15

<210> SEQ ID NO 137
<211> LENGTH: 16
<212> TYPE: PRT
<213> ORGANISM: Influenza A virus

<400> SEQUENCE: 137

Val Ser Val Gly Thr Ser Thr Leu Asn Gln Arg Leu Ile Pro Glu Ile
1 5 10 15

<210> SEQ ID NO 138
<211> LENGTH: 16
<212> TYPE: PRT
<213> ORGANISM: Influenza A virus

<400> SEQUENCE: 138

Val Ser Val Gly Thr Ser Thr Leu Asn Gln Arg Leu Ile Pro Arg Ile
1 5 10 15

<210> SEQ ID NO 139
<211> LENGTH: 16
<212> TYPE: PRT
<213> ORGANISM: Influenza A virus

<400> SEQUENCE: 139

-continued

Val Ser Val Gly Thr Ser Thr Leu Asn Gln Arg Ser Val Pro Lys Ile
1 5 10 15

<210> SEQ ID NO 140
<211> LENGTH: 16
<212> TYPE: PRT
<213> ORGANISM: Influenza A virus

<400> SEQUENCE: 140

Val Ser Val Gly Thr Ser Thr Leu Asn Gln Arg Ser Val Pro Glu Ile
1 5 10 15

<210> SEQ ID NO 141
<211> LENGTH: 16
<212> TYPE: PRT
<213> ORGANISM: Influenza A virus

<400> SEQUENCE: 141

Val Ser Val Gly Thr Ser Thr Leu Asn Gln Arg Ser Val Pro Arg Ile
1 5 10 15

<210> SEQ ID NO 142
<211> LENGTH: 16
<212> TYPE: PRT
<213> ORGANISM: Influenza A virus

<400> SEQUENCE: 142

Val Ser Val Gly Thr Ser Thr Leu Asn Gln Arg Ser Ile Pro Lys Ile
1 5 10 15

<210> SEQ ID NO 143
<211> LENGTH: 16
<212> TYPE: PRT
<213> ORGANISM: Influenza A virus

<400> SEQUENCE: 143

Val Ser Val Gly Thr Ser Thr Leu Asn Gln Arg Ser Ile Pro Glu Ile
1 5 10 15

<210> SEQ ID NO 144
<211> LENGTH: 16
<212> TYPE: PRT
<213> ORGANISM: Influenza A virus

<400> SEQUENCE: 144

Val Ser Val Gly Thr Ser Thr Leu Asn Gln Arg Ser Ile Pro Arg Ile
1 5 10 15

<210> SEQ ID NO 145
<211> LENGTH: 22
<212> TYPE: PRT
<213> ORGANISM: Influenza A virus

<400> SEQUENCE: 145

Lys Ala Asn Pro Ala Asn Asp Leu Gly Asn Pro Met Ser Asp Glu Phe
1 5 10 15

Ile Asn Val Pro Glu Trp
20

<210> SEQ ID NO 146
<211> LENGTH: 22
<212> TYPE: PRT
<213> ORGANISM: Influenza A virus

<400> SEQUENCE: 146

-continued

```
Lys Ala Asn Pro Ala Asn Asp Leu Gly Asn Pro Met Ser Asp Glu Phe
1               5                   10                  15

Leu Asn Val Pro Glu Trp
            20


<210> SEQ ID NO 147
<211> LENGTH: 22
<212> TYPE: PRT
<213> ORGANISM: Influenza A virus

<400> SEQUENCE: 147

Lys Ala Asn Pro Ala Asn Gly Leu Gly Asn Pro Met Ser Asp Glu Phe
1               5                   10                  15

Ile Asn Val Pro Glu Trp
            20


<210> SEQ ID NO 148
<211> LENGTH: 22
<212> TYPE: PRT
<213> ORGANISM: Influenza A virus

<400> SEQUENCE: 148

Lys Ala Asn Pro Ala Asn Gly Leu Gly Asn Pro Met Ser Asp Glu Phe
1               5                   10                  15

Leu Asn Val Pro Glu Trp
            20


<210> SEQ ID NO 149
<211> LENGTH: 22
<212> TYPE: PRT
<213> ORGANISM: Influenza A virus

<400> SEQUENCE: 149

Lys Ala Asn Pro Val Asn Asp Leu Gly Asn Pro Met Ser Asp Glu Phe
1               5                   10                  15

Ile Asn Val Pro Glu Trp
            20


<210> SEQ ID NO 150
<211> LENGTH: 22
<212> TYPE: PRT
<213> ORGANISM: Influenza A virus

<400> SEQUENCE: 150

Lys Ala Asn Pro Val Asn Asp Leu Gly Asn Pro Met Ser Asp Glu Phe
1               5                   10                  15

Leu Asn Val Pro Glu Trp
            20


<210> SEQ ID NO 151
<211> LENGTH: 22
<212> TYPE: PRT
<213> ORGANISM: Influenza A virus

<400> SEQUENCE: 151

Lys Ala Asn Pro Val Asn Gly Leu Gly Asn Pro Met Ser Asp Glu Phe
1               5                   10                  15

Ile Asn Val Pro Glu Trp
            20


<210> SEQ ID NO 152
```

-continued

<211> LENGTH: 22
<212> TYPE: PRT
<213> ORGANISM: Influenza A virus

<400> SEQUENCE: 152

Lys Ala Asn Pro Val Asn Gly Leu Gly Asn Pro Met Ser Asp Glu Phe
1 5 10 15

Leu Asn Val Pro Glu Trp
20

<210> SEQ ID NO 153
<211> LENGTH: 22
<212> TYPE: PRT
<213> ORGANISM: Influenza A virus

<400> SEQUENCE: 153

Lys Ala Ser Pro Ala Asn Asp Leu Gly Asn Pro Met Ser Asp Glu Phe
1 5 10 15

Ile Asn Val Pro Glu Trp
20

<210> SEQ ID NO 154
<211> LENGTH: 22
<212> TYPE: PRT
<213> ORGANISM: Influenza A virus

<400> SEQUENCE: 154

Lys Ala Ser Pro Ala Asn Asp Leu Gly Asn Pro Met Ser Asp Glu Phe
1 5 10 15

Leu Asn Val Pro Glu Trp
20

<210> SEQ ID NO 155
<211> LENGTH: 22
<212> TYPE: PRT
<213> ORGANISM: Influenza A virus

<400> SEQUENCE: 155

Lys Ala Ser Pro Ala Asn Gly Leu Gly Asn Pro Met Ser Asp Glu Phe
1 5 10 15

Ile Asn Val Pro Glu Trp
20

<210> SEQ ID NO 156
<211> LENGTH: 22
<212> TYPE: PRT
<213> ORGANISM: Influenza A virus

<400> SEQUENCE: 156

Lys Ala Ser Pro Ala Asn Gly Leu Gly Asn Pro Met Ser Asp Glu Phe
1 5 10 15

Leu Asn Val Pro Glu Trp
20

<210> SEQ ID NO 157
<211> LENGTH: 22
<212> TYPE: PRT
<213> ORGANISM: Influenza A virus

<400> SEQUENCE: 157

Lys Ala Ser Pro Val Asn Asp Leu Gly Asn Pro Met Ser Asp Glu Phe
1 5 10 15

-continued

```
Ile Asn Val Pro Glu Trp
            20


<210> SEQ ID NO 158
<211> LENGTH: 22
<212> TYPE: PRT
<213> ORGANISM: Influenza A virus

<400> SEQUENCE: 158

Lys Ala Ser Pro Val Asn Asp Leu Gly Asn Pro Met Ser Asp Glu Phe
1               5                   10                  15

Leu Asn Val Pro Glu Trp
            20


<210> SEQ ID NO 159
<211> LENGTH: 22
<212> TYPE: PRT
<213> ORGANISM: Influenza A virus

<400> SEQUENCE: 159

Lys Ala Ser Pro Val Asn Gly Leu Gly Asn Pro Met Ser Asp Glu Phe
1               5                   10                  15

Ile Asn Val Pro Glu Trp
            20


<210> SEQ ID NO 160
<211> LENGTH: 22
<212> TYPE: PRT
<213> ORGANISM: Influenza A virus

<400> SEQUENCE: 160

Lys Ala Ser Pro Val Asn Gly Leu Gly Asn Pro Met Ser Asp Glu Phe
1               5                   10                  15

Leu Asn Val Pro Glu Trp
            20


<210> SEQ ID NO 161
<211> LENGTH: 22
<212> TYPE: PRT
<213> ORGANISM: Influenza A virus

<400> SEQUENCE: 161

Lys Asp Asn Pro Ala Asn Asp Leu Gly Asn Pro Met Ser Asp Glu Phe
1               5                   10                  15

Ile Asn Val Pro Glu Trp
            20


<210> SEQ ID NO 162
<211> LENGTH: 22
<212> TYPE: PRT
<213> ORGANISM: Influenza A virus

<400> SEQUENCE: 162

Lys Asp Asn Pro Ala Asn Asp Leu Gly Asn Pro Met Ser Asp Glu Phe
1               5                   10                  15

Leu Asn Val Pro Glu Trp
            20


<210> SEQ ID NO 163
<211> LENGTH: 22
<212> TYPE: PRT
<213> ORGANISM: Influenza A virus
```

-continued

<400> SEQUENCE: 163

Lys Asp Asn Pro Ala Asn Gly Leu Gly Asn Pro Met Ser Asp Glu Phe
1 5 10 15

Ile Asn Val Pro Glu Trp
20

<210> SEQ ID NO 164
<211> LENGTH: 22
<212> TYPE: PRT
<213> ORGANISM: Influenza A virus

<400> SEQUENCE: 164

Lys Asp Asn Pro Ala Asn Gly Leu Gly Asn Pro Met Ser Asp Glu Phe
1 5 10 15

Leu Asn Val Pro Glu Trp
20

<210> SEQ ID NO 165
<211> LENGTH: 22
<212> TYPE: PRT
<213> ORGANISM: Influenza A virus

<400> SEQUENCE: 165

Lys Asp Asn Pro Val Asn Asp Leu Gly Asn Pro Met Ser Asp Glu Phe
1 5 10 15

Ile Asn Val Pro Glu Trp
20

<210> SEQ ID NO 166
<211> LENGTH: 22
<212> TYPE: PRT
<213> ORGANISM: Influenza A virus

<400> SEQUENCE: 166

Lys Asp Asn Pro Val Asn Asp Leu Gly Asn Pro Met Ser Asp Glu Phe
1 5 10 15

Leu Asn Val Pro Glu Trp
20

<210> SEQ ID NO 167
<211> LENGTH: 22
<212> TYPE: PRT
<213> ORGANISM: Influenza A virus

<400> SEQUENCE: 167

Lys Asp Asn Pro Val Asn Gly Leu Gly Asn Pro Met Ser Asp Glu Phe
1 5 10 15

Ile Asn Val Pro Glu Trp
20

<210> SEQ ID NO 168
<211> LENGTH: 22
<212> TYPE: PRT
<213> ORGANISM: Influenza A virus

<400> SEQUENCE: 168

Lys Asp Asn Pro Val Asn Gly Leu Gly Asn Pro Met Ser Asp Glu Phe
1 5 10 15

Leu Asn Val Pro Glu Trp
20

-continued

<210> SEQ ID NO 169
<211> LENGTH: 22
<212> TYPE: PRT
<213> ORGANISM: Influenza A virus

<400> SEQUENCE: 169

```
Lys Asp Ser Pro Ala Asn Asp Leu Gly Asn Pro Met Ser Asp Glu Phe
1               5                   10                  15

Ile Asn Val Pro Glu Trp
            20
```

<210> SEQ ID NO 170
<211> LENGTH: 22
<212> TYPE: PRT
<213> ORGANISM: Influenza A virus

<400> SEQUENCE: 170

```
Lys Asp Ser Pro Ala Asn Asp Leu Gly Asn Pro Met Ser Asp Glu Phe
1               5                   10                  15

Leu Asn Val Pro Glu Trp
            20
```

<210> SEQ ID NO 171
<211> LENGTH: 22
<212> TYPE: PRT
<213> ORGANISM: Influenza A virus

<400> SEQUENCE: 171

```
Lys Asp Ser Pro Ala Asn Gly Leu Gly Asn Pro Met Ser Asp Glu Phe
1               5                   10                  15

Ile Asn Val Pro Glu Trp
            20
```

<210> SEQ ID NO 172
<211> LENGTH: 22
<212> TYPE: PRT
<213> ORGANISM: Influenza A virus

<400> SEQUENCE: 172

```
Lys Asp Ser Pro Ala Asn Gly Leu Gly Asn Pro Met Ser Asp Glu Phe
1               5                   10                  15

Leu Asn Val Pro Glu Trp
            20
```

<210> SEQ ID NO 173
<211> LENGTH: 22
<212> TYPE: PRT
<213> ORGANISM: Influenza A virus

<400> SEQUENCE: 173

```
Lys Asp Ser Pro Val Asn Asp Leu Gly Asn Pro Met Ser Asp Glu Phe
1               5                   10                  15

Ile Asn Val Pro Glu Trp
            20
```

<210> SEQ ID NO 174
<211> LENGTH: 22
<212> TYPE: PRT
<213> ORGANISM: Influenza A virus

<400> SEQUENCE: 174

```
Lys Asp Ser Pro Val Asn Asp Leu Gly Asn Pro Met Ser Asp Glu Phe
1               5                   10                  15
```

-continued

Leu Asn Val Pro Glu Trp
20

<210> SEQ ID NO 175
<211> LENGTH: 22
<212> TYPE: PRT
<213> ORGANISM: Influenza A virus

<400> SEQUENCE: 175

Lys Asp Ser Pro Val Asn Gly Leu Gly Asn Pro Met Ser Asp Glu Phe
1 5 10 15

Ile Asn Val Pro Glu Trp
20

<210> SEQ ID NO 176
<211> LENGTH: 22
<212> TYPE: PRT
<213> ORGANISM: Influenza A virus

<400> SEQUENCE: 176

Lys Asp Ser Pro Val Asn Gly Leu Gly Asn Pro Met Ser Asp Glu Phe
1 5 10 15

Leu Asn Val Pro Glu Trp
20

<210> SEQ ID NO 177
<211> LENGTH: 22
<212> TYPE: PRT
<213> ORGANISM: Influenza A virus

<400> SEQUENCE: 177

Pro Tyr Gln Gly Lys Ser Ser Phe Phe Arg Asn Val Val Trp Leu Ile
1 5 10 15

Lys Lys Asn Ser Ala Tyr
20

<210> SEQ ID NO 178
<211> LENGTH: 22
<212> TYPE: PRT
<213> ORGANISM: Influenza A virus

<400> SEQUENCE: 178

Pro Tyr Gln Gly Lys Ser Ser Phe Phe Arg Asn Val Val Trp Leu Ile
1 5 10 15

Lys Lys Asn Ser Thr Tyr
20

<210> SEQ ID NO 179
<211> LENGTH: 22
<212> TYPE: PRT
<213> ORGANISM: Influenza A virus

<400> SEQUENCE: 179

Pro Tyr Gln Gly Lys Ser Ser Phe Phe Arg Asn Val Val Trp Leu Ile
1 5 10 15

Lys Lys Asn Ser Val Tyr
20

<210> SEQ ID NO 180
<211> LENGTH: 22
<212> TYPE: PRT
<213> ORGANISM: Influenza A virus -continued

<400> SEQUENCE: 180

Pro Tyr Asn Gly Lys Ser Ser Phe Phe Arg Asn Val Val Trp Leu Ile
1 5 10 15

Lys Lys Asn Ser Ala Tyr
20

<210> SEQ ID NO 181
<211> LENGTH: 22
<212> TYPE: PRT
<213> ORGANISM: Influenza A virus

<400> SEQUENCE: 181

Pro Tyr Asn Gly Lys Ser Ser Phe Phe Arg Asn Val Val Trp Leu Ile
1 5 10 15

Lys Lys Asn Ser Thr Tyr
20

<210> SEQ ID NO 182
<211> LENGTH: 22
<212> TYPE: PRT
<213> ORGANISM: Influenza A virus

<400> SEQUENCE: 182

Pro Tyr Asn Gly Lys Ser Ser Phe Phe Arg Asn Val Val Trp Leu Ile
1 5 10 15

Lys Lys Asn Ser Val Tyr
20

<210> SEQ ID NO 183
<211> LENGTH: 22
<212> TYPE: PRT
<213> ORGANISM: Influenza A virus

<400> SEQUENCE: 183

Pro Tyr Leu Gly Lys Ser Ser Phe Phe Arg Asn Val Val Trp Leu Ile
1 5 10 15

Lys Lys Asn Ser Ala Tyr
20

<210> SEQ ID NO 184
<211> LENGTH: 22
<212> TYPE: PRT
<213> ORGANISM: Influenza A virus

<400> SEQUENCE: 184

Pro Tyr Leu Gly Lys Ser Ser Phe Phe Arg Asn Val Val Trp Leu Ile
1 5 10 15

Lys Lys Asn Ser Thr Tyr
20

<210> SEQ ID NO 185
<211> LENGTH: 22
<212> TYPE: PRT
<213> ORGANISM: Influenza A virus

<400> SEQUENCE: 185

Pro Tyr Leu Gly Lys Ser Ser Phe Phe Arg Asn Val Val Trp Leu Ile
1 5 10 15

Lys Lys Asn Ser Val Tyr
20

<210> SEQ ID NO 186
<211> LENGTH: 22
<212> TYPE: PRT
<213> ORGANISM: Influenza A virus

<400> SEQUENCE: 186

Pro Tyr Gln Gly Lys Ser Ser Phe Phe Arg Asn Val Val Trp Leu Ile
1 5 10 15

Lys Lys Asn Asn Ala Tyr
20

<210> SEQ ID NO 187
<211> LENGTH: 22
<212> TYPE: PRT
<213> ORGANISM: Influenza A virus

<400> SEQUENCE: 187

Pro Tyr Gln Gly Lys Ser Ser Phe Phe Arg Asn Val Val Trp Leu Ile
1 5 10 15

Lys Lys Asn Asn Thr Tyr
20

<210> SEQ ID NO 188
<211> LENGTH: 22
<212> TYPE: PRT
<213> ORGANISM: Influenza A virus

<400> SEQUENCE: 188

Pro Tyr Gln Gly Lys Ser Ser Phe Phe Arg Asn Val Val Trp Leu Ile
1 5 10 15

Lys Lys Asn Asn Val Tyr
20

<210> SEQ ID NO 189
<211> LENGTH: 22
<212> TYPE: PRT
<213> ORGANISM: Influenza A virus

<400> SEQUENCE: 189

Pro Tyr Asn Gly Lys Ser Ser Phe Phe Arg Asn Val Val Trp Leu Ile
1 5 10 15

Lys Lys Asn Asn Ala Tyr
20

<210> SEQ ID NO 190
<211> LENGTH: 22
<212> TYPE: PRT
<213> ORGANISM: Influenza A virus

<400> SEQUENCE: 190

Pro Tyr Asn Gly Lys Ser Ser Phe Phe Arg Asn Val Val Trp Leu Ile
1 5 10 15

Lys Lys Asn Asn Thr Tyr
20

<210> SEQ ID NO 191
<211> LENGTH: 22
<212> TYPE: PRT
<213> ORGANISM: Influenza A virus

<400> SEQUENCE: 191

Pro Tyr Asn Gly Lys Ser Ser Phe Phe Arg Asn Val Val Trp Leu Ile

-continued

```
1               5                   10                  15

Lys Lys Asn Asn Val Tyr
            20


<210> SEQ ID NO 192
<211> LENGTH: 22
<212> TYPE: PRT
<213> ORGANISM: Influenza A virus

<400> SEQUENCE: 192

Pro Tyr Leu Gly Lys Ser Ser Phe Phe Arg Asn Val Val Trp Leu Ile
1               5                   10                  15

Lys Lys Asn Asn Ala Tyr
            20


<210> SEQ ID NO 193
<211> LENGTH: 22
<212> TYPE: PRT
<213> ORGANISM: Influenza A virus

<400> SEQUENCE: 193

Pro Tyr Leu Gly Lys Ser Ser Phe Phe Arg Asn Val Val Trp Leu Ile
1               5                   10                  15

Lys Lys Asn Asn Thr Tyr
            20


<210> SEQ ID NO 194
<211> LENGTH: 22
<212> TYPE: PRT
<213> ORGANISM: Influenza A virus

<400> SEQUENCE: 194

Pro Tyr Leu Gly Lys Ser Ser Phe Phe Arg Asn Val Val Trp Leu Ile
1               5                   10                  15

Lys Lys Asn Asn Val Tyr
            20


<210> SEQ ID NO 195
<211> LENGTH: 22
<212> TYPE: PRT
<213> ORGANISM: Influenza A virus

<400> SEQUENCE: 195

Pro Tyr Gln Gly Arg Ser Ser Phe Phe Arg Asn Val Val Trp Leu Ile
1               5                   10                  15

Lys Lys Asn Ser Ala Tyr
            20


<210> SEQ ID NO 196
<211> LENGTH: 22
<212> TYPE: PRT
<213> ORGANISM: Influenza A virus

<400> SEQUENCE: 196

Pro Tyr Gln Gly Arg Ser Ser Phe Phe Arg Asn Val Val Trp Leu Ile
1               5                   10                  15

Lys Lys Asn Ser Thr Tyr
            20


<210> SEQ ID NO 197
<211> LENGTH: 22
<212> TYPE: PRT
```

-continued

<213> ORGANISM: Influenza A virus

<400> SEQUENCE: 197

Pro Tyr Gln Gly Arg Ser Ser Phe Phe Arg Asn Val Val Trp Leu Ile
1 5 10 15

Lys Lys Asn Ser Val Tyr
20

<210> SEQ ID NO 198
<211> LENGTH: 22
<212> TYPE: PRT
<213> ORGANISM: Influenza A virus

<400> SEQUENCE: 198

Pro Tyr Asn Gly Arg Ser Ser Phe Phe Arg Asn Val Val Trp Leu Ile
1 5 10 15

Lys Lys Asn Ser Ala Tyr
20

<210> SEQ ID NO 199
<211> LENGTH: 22
<212> TYPE: PRT
<213> ORGANISM: Influenza A virus

<400> SEQUENCE: 199

Pro Tyr Asn Gly Arg Ser Ser Phe Phe Arg Asn Val Val Trp Leu Ile
1 5 10 15

Lys Lys Asn Ser Thr Tyr
20

<210> SEQ ID NO 200
<211> LENGTH: 22
<212> TYPE: PRT
<213> ORGANISM: Influenza A virus

<400> SEQUENCE: 200

Pro Tyr Asn Gly Arg Ser Ser Phe Phe Arg Asn Val Val Trp Leu Ile
1 5 10 15

Lys Lys Asn Ser Val Tyr
20

<210> SEQ ID NO 201
<211> LENGTH: 22
<212> TYPE: PRT
<213> ORGANISM: Influenza A virus

<400> SEQUENCE: 201

Pro Tyr Leu Gly Arg Ser Ser Phe Phe Arg Asn Val Val Trp Leu Ile
1 5 10 15

Lys Lys Asn Ser Ala Tyr
20

<210> SEQ ID NO 202
<211> LENGTH: 22
<212> TYPE: PRT
<213> ORGANISM: Influenza A virus

<400> SEQUENCE: 202

Pro Tyr Leu Gly Arg Ser Ser Phe Phe Arg Asn Val Val Trp Leu Ile
1 5 10 15

Lys Lys Asn Ser Thr Tyr
20

-continued

<210> SEQ ID NO 203
<211> LENGTH: 22
<212> TYPE: PRT
<213> ORGANISM: Influenza A virus

<400> SEQUENCE: 203

Pro Tyr Leu Gly Arg Ser Ser Phe Phe Arg Asn Val Val Trp Leu Ile
1 5 10 15

Lys Lys Asn Ser Val Tyr
20

<210> SEQ ID NO 204
<211> LENGTH: 22
<212> TYPE: PRT
<213> ORGANISM: Influenza A virus

<400> SEQUENCE: 204

Pro Tyr Gln Gly Arg Ser Ser Phe Phe Arg Asn Val Val Trp Leu Ile
1 5 10 15

Lys Lys Asn Asn Ala Tyr
20

<210> SEQ ID NO 205
<211> LENGTH: 22
<212> TYPE: PRT
<213> ORGANISM: Influenza A virus

<400> SEQUENCE: 205

Pro Tyr Gln Gly Arg Ser Ser Phe Phe Arg Asn Val Val Trp Leu Ile
1 5 10 15

Lys Lys Asn Asn Thr Tyr
20

<210> SEQ ID NO 206
<211> LENGTH: 22
<212> TYPE: PRT
<213> ORGANISM: Influenza A virus

<400> SEQUENCE: 206

Pro Tyr Gln Gly Arg Ser Ser Phe Phe Arg Asn Val Val Trp Leu Ile
1 5 10 15

Lys Lys Asn Asn Val Tyr
20

<210> SEQ ID NO 207
<211> LENGTH: 22
<212> TYPE: PRT
<213> ORGANISM: Influenza A virus

<400> SEQUENCE: 207

Pro Tyr Asn Gly Arg Ser Ser Phe Phe Arg Asn Val Val Trp Leu Ile
1 5 10 15

Lys Lys Asn Asn Ala Tyr
20

<210> SEQ ID NO 208
<211> LENGTH: 22
<212> TYPE: PRT
<213> ORGANISM: Influenza A virus

<400> SEQUENCE: 208

-continued

Pro Tyr Asn Gly Arg Ser Ser Phe Phe Arg Asn Val Val Trp Leu Ile
1 5 10 15

Lys Lys Asn Asn Thr Tyr
20

<210> SEQ ID NO 209
<211> LENGTH: 22
<212> TYPE: PRT
<213> ORGANISM: Influenza A virus

<400> SEQUENCE: 209

Pro Tyr Asn Gly Arg Ser Ser Phe Phe Arg Asn Val Val Trp Leu Ile
1 5 10 15

Lys Lys Asn Asn Val Tyr
20

<210> SEQ ID NO 210
<211> LENGTH: 22
<212> TYPE: PRT
<213> ORGANISM: Influenza A virus

<400> SEQUENCE: 210

Pro Tyr Leu Gly Arg Ser Ser Phe Phe Arg Asn Val Val Trp Leu Ile
1 5 10 15

Lys Lys Asn Asn Ala Tyr
20

<210> SEQ ID NO 211
<211> LENGTH: 22
<212> TYPE: PRT
<213> ORGANISM: Influenza A virus

<400> SEQUENCE: 211

Pro Tyr Leu Gly Arg Ser Ser Phe Phe Arg Asn Val Val Trp Leu Ile
1 5 10 15

Lys Lys Asn Asn Thr Tyr
20

<210> SEQ ID NO 212
<211> LENGTH: 22
<212> TYPE: PRT
<213> ORGANISM: Influenza A virus

<400> SEQUENCE: 212

Pro Tyr Leu Gly Arg Ser Ser Phe Phe Arg Asn Val Val Trp Leu Ile
1 5 10 15

Lys Lys Asn Asn Val Tyr
20

<210> SEQ ID NO 213
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
di-palmitoyl-Lys-Ser-Ser-

<400> SEQUENCE: 213

Pro Tyr Gln Gly Lys Ser Ser Phe Phe Arg Asn Val Val Trp Leu Ile
1 5 10 15

Lys Lys Asn Ser Ala Tyr

20

<210> SEQ ID NO 214
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 214

Pro Tyr Gln Gly Lys Ser Ser Phe Phe Arg Asn Val Val Trp Leu Ile
1 5 10 15

Lys Lys Asn Ser Thr Tyr
20

<210> SEQ ID NO 215
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 215

Pro Tyr Gln Gly Lys Ser Ser Phe Phe Arg Asn Val Val Trp Leu Ile
1 5 10 15

Lys Lys Asn Ser Val Tyr
20

<210> SEQ ID NO 216
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 216

Pro Tyr Asn Gly Lys Ser Ser Phe Phe Arg Asn Val Val Trp Leu Ile
1 5 10 15

Lys Lys Asn Ser Ala Tyr
20

<210> SEQ ID NO 217
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 217

Pro Tyr Asn Gly Lys Ser Ser Phe Phe Arg Asn Val Val Trp Leu Ile
1 5 10 15

Lys Lys Asn Ser Thr Tyr
20

-continued

<210> SEQ ID NO 218
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 218

```
Pro Tyr Asn Gly Lys Ser Ser Phe Phe Arg Asn Val Val Trp Leu Ile
1               5                   10                  15

Lys Lys Asn Ser Val Tyr
            20
```

<210> SEQ ID NO 219
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 219

```
Pro Tyr Leu Gly Lys Ser Ser Phe Phe Arg Asn Val Val Trp Leu Ile
1               5                   10                  15

Lys Lys Asn Ser Ala Tyr
            20
```

<210> SEQ ID NO 220
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 220

```
Pro Tyr Leu Gly Lys Ser Ser Phe Phe Arg Asn Val Val Trp Leu Ile
1               5                   10                  15

Lys Lys Asn Ser Thr Tyr
            20
```

<210> SEQ ID NO 221
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 221

```
Pro Tyr Leu Gly Lys Ser Ser Phe Phe Arg Asn Val Val Trp Leu Ile
1               5                   10                  15

Lys Lys Asn Ser Val Tyr
            20
```

<210> SEQ ID NO 222
<211> LENGTH: 22
<212> TYPE: PRT

<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 222

Pro Tyr Gln Gly Lys Ser Ser Phe Phe Arg Asn Val Val Trp Leu Ile
1 5 10 15

Lys Lys Asn Asn Ala Tyr
20

<210> SEQ ID NO 223
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 223

Pro Tyr Gln Gly Lys Ser Ser Phe Phe Arg Asn Val Val Trp Leu Ile
1 5 10 15

Lys Lys Asn Asn Thr Tyr
20

<210> SEQ ID NO 224
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 224

Pro Tyr Gln Gly Lys Ser Ser Phe Phe Arg Asn Val Val Trp Leu Ile
1 5 10 15

Lys Lys Asn Asn Val Tyr
20

<210> SEQ ID NO 225
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 225

Pro Tyr Asn Gly Lys Ser Ser Phe Phe Arg Asn Val Val Trp Leu Ile
1 5 10 15

Lys Lys Asn Asn Ala Tyr
20

<210> SEQ ID NO 226
<211> LENGTH: 22
<212> TYPE: PRT
<213> ORGANISM: Influenza A virus
<220> FEATURE:
<221> NAME/KEY: MISC_FEATURE -continued
<222> LOCATION: (1)..(1)
<223> OTHER INFORMATION: residue lipidated, for example with
      di-palmitoyl-Lys-Ser-Ser-

<400> SEQUENCE: 226

Pro Tyr Asn Gly Lys Ser Ser Phe Phe Arg Asn Val Val Trp Leu Ile
1               5                   10                  15

Lys Lys Asn Asn Thr Tyr
            20

<210> SEQ ID NO 227
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 227

Pro Tyr Asn Gly Lys Ser Ser Phe Phe Arg Asn Val Val Trp Leu Ile
1               5                   10                  15

Lys Lys Asn Asn Val Tyr
            20

<210> SEQ ID NO 228
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 228

Pro Tyr Leu Gly Lys Ser Ser Phe Phe Arg Asn Val Val Trp Leu Ile
1               5                   10                  15

Lys Lys Asn Asn Ala Tyr
            20

<210> SEQ ID NO 229
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 229

Pro Tyr Leu Gly Lys Ser Ser Phe Phe Arg Asn Val Val Trp Leu Ile
1               5                   10                  15

Lys Lys Asn Asn Thr Tyr
            20

<210> SEQ ID NO 230
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser- -continued

<400> SEQUENCE: 230

Pro Tyr Leu Gly Lys Ser Ser Phe Phe Arg Asn Val Val Trp Leu Ile
1               5                   10                  15

Lys Lys Asn Asn Val Tyr
            20

<210> SEQ ID NO 231
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 231

Pro Tyr Gln Gly Arg Ser Ser Phe Phe Arg Asn Val Val Trp Leu Ile
1               5                   10                  15

Lys Lys Asn Ser Ala Tyr
            20

<210> SEQ ID NO 232
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 232

Pro Tyr Gln Gly Arg Ser Ser Phe Phe Arg Asn Val Val Trp Leu Ile
1               5                   10                  15

Lys Lys Asn Ser Thr Tyr
            20

<210> SEQ ID NO 233
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 233

Pro Tyr Gln Gly Arg Ser Ser Phe Phe Arg Asn Val Val Trp Leu Ile
1               5                   10                  15

Lys Lys Asn Ser Val Tyr
            20

<210> SEQ ID NO 234
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 234

-continued

Pro Tyr Asn Gly Arg Ser Ser Phe Phe Arg Asn Val Val Trp Leu Ile
1 5 10 15

Lys Lys Asn Ser Ala Tyr
20

<210> SEQ ID NO 235
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 235

Pro Tyr Asn Gly Arg Ser Ser Phe Phe Arg Asn Val Val Trp Leu Ile
1 5 10 15

Lys Lys Asn Ser Thr Tyr
20

<210> SEQ ID NO 236
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 236

Pro Tyr Asn Gly Arg Ser Ser Phe Phe Arg Asn Val Val Trp Leu Ile
1 5 10 15

Lys Lys Asn Ser Val Tyr
20

<210> SEQ ID NO 237
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 237

Pro Tyr Leu Gly Arg Ser Ser Phe Phe Arg Asn Val Val Trp Leu Ile
1 5 10 15

Lys Lys Asn Ser Ala Tyr
20

<210> SEQ ID NO 238
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 238

Pro Tyr Leu Gly Arg Ser Ser Phe Phe Arg Asn Val Val Trp Leu Ile
1 5 10 15

-continued

```
Lys Lys Asn Ser Thr Tyr
            20


<210> SEQ ID NO 239
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 239

Pro Tyr Leu Gly Arg Ser Ser Phe Phe Arg Asn Val Val Trp Leu Ile
1               5                   10                  15

Lys Lys Asn Ser Val Tyr
            20


<210> SEQ ID NO 240
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 240

Pro Tyr Gln Gly Arg Ser Ser Phe Phe Arg Asn Val Val Trp Leu Ile
1               5                   10                  15

Lys Lys Asn Asn Ala Tyr
            20


<210> SEQ ID NO 241
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 241

Pro Tyr Gln Gly Arg Ser Ser Phe Phe Arg Asn Val Val Trp Leu Ile
1               5                   10                  15

Lys Lys Asn Asn Thr Tyr
            20


<210> SEQ ID NO 242
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 242

Pro Tyr Gln Gly Arg Ser Ser Phe Phe Arg Asn Val Val Trp Leu Ile
1               5                   10                  15

Lys Lys Asn Asn Val Tyr
            20
```

<210> SEQ ID NO 243
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 243

```
Pro Tyr Asn Gly Arg Ser Ser Phe Phe Arg Asn Val Val Trp Leu Ile
1               5                   10                  15

Lys Lys Asn Asn Ala Tyr
            20
```

<210> SEQ ID NO 244
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 244

```
Pro Tyr Asn Gly Arg Ser Ser Phe Phe Arg Asn Val Val Trp Leu Ile
1               5                   10                  15

Lys Lys Asn Asn Thr Tyr
            20
```

<210> SEQ ID NO 245
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 245

```
Pro Tyr Asn Gly Arg Ser Ser Phe Phe Arg Asn Val Val Trp Leu Ile
1               5                   10                  15

Lys Lys Asn Asn Val Tyr
            20
```

<210> SEQ ID NO 246
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 246

```
Pro Tyr Leu Gly Arg Ser Ser Phe Phe Arg Asn Val Val Trp Leu Ile
1               5                   10                  15

Lys Lys Asn Asn Ala Tyr
            20
```

<210> SEQ ID NO 247
<211> LENGTH: 22

-continued

```
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 247

Pro Tyr Leu Gly Arg Ser Ser Phe Phe Arg Asn Val Val Trp Leu Ile
1               5                   10                  15

Lys Lys Asn Asn Thr Tyr
            20


<210> SEQ ID NO 248
<211> LENGTH: 22
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 248

Pro Tyr Leu Gly Arg Ser Ser Phe Phe Arg Asn Val Val Trp Leu Ile
1               5                   10                  15

Lys Lys Asn Asn Val Tyr
            20


<210> SEQ ID NO 249
<211> LENGTH: 22
<212> TYPE: PRT
<213> ORGANISM: Influenza A virus

<400> SEQUENCE: 249

Asn His Glu Ala Ser Ser Gly Val Ser Ser Ala Ser Pro Tyr Gln Gly
1               5                   10                  15

Lys Ser Ser Phe Phe Gly
            20


<210> SEQ ID NO 250
<211> LENGTH: 22
<212> TYPE: PRT
<213> ORGANISM: Influenza A virus

<400> SEQUENCE: 250

Asn His Glu Ala Ser Ser Gly Val Ser Ser Ala Ser Pro Tyr Asn Gly
1               5                   10                  15

Lys Ser Ser Phe Phe Gly
            20


<210> SEQ ID NO 251
<211> LENGTH: 22
<212> TYPE: PRT
<213> ORGANISM: Influenza A virus

<400> SEQUENCE: 251

Asn His Glu Ala Ser Ser Gly Val Ser Ser Ala Ser Pro Tyr Leu Gly
1               5                   10                  15

Lys Ser Ser Phe Phe Gly
            20


<210> SEQ ID NO 252
```

<211> LENGTH: 22
<212> TYPE: PRT
<213> ORGANISM: Influenza A virus

<400> SEQUENCE: 252

Asn His Glu Ala Ser Ser Gly Val Ser Ser Ala Ser Pro Tyr Gln Gly
1 5 10 15

Arg Ser Ser Phe Phe Gly
20

<210> SEQ ID NO 253
<211> LENGTH: 22
<212> TYPE: PRT
<213> ORGANISM: Influenza A virus

<400> SEQUENCE: 253

Asn His Glu Ala Ser Ser Gly Val Ser Ser Ala Ser Pro Tyr Asn Gly
1 5 10 15

Arg Ser Ser Phe Phe Gly
20

<210> SEQ ID NO 254
<211> LENGTH: 22
<212> TYPE: PRT
<213> ORGANISM: Influenza A virus

<400> SEQUENCE: 254

Asn His Glu Ala Ser Ser Gly Val Ser Ser Ala Ser Pro Tyr Leu Gly
1 5 10 15

Arg Ser Ser Phe Phe Gly
20

<210> SEQ ID NO 255
<211> LENGTH: 22
<212> TYPE: PRT
<213> ORGANISM: Influenza A virus

<400> SEQUENCE: 255

Asn His Glu Ala Ser Leu Gly Val Ser Ser Ala Ser Pro Tyr Gln Gly
1 5 10 15

Lys Ser Ser Phe Phe Gly
20

<210> SEQ ID NO 256
<211> LENGTH: 22
<212> TYPE: PRT
<213> ORGANISM: Influenza A virus

<400> SEQUENCE: 256

Asn His Glu Ala Ser Leu Gly Val Ser Ser Ala Ser Pro Tyr Asn Gly
1 5 10 15

Lys Ser Ser Phe Phe Gly
20

<210> SEQ ID NO 257
<211> LENGTH: 22
<212> TYPE: PRT
<213> ORGANISM: Influenza A virus

<400> SEQUENCE: 257

Asn His Glu Ala Ser Leu Gly Val Ser Ser Ala Ser Pro Tyr Leu Gly
1 5 10 15

-continued

Lys Ser Ser Phe Phe Gly
20

<210> SEQ ID NO 258
<211> LENGTH: 22
<212> TYPE: PRT
<213> ORGANISM: Influenza A virus

<400> SEQUENCE: 258

Asn His Glu Ala Ser Leu Gly Val Ser Ser Ala Ser Pro Tyr Gln Gly
1 5 10 15

Arg Ser Ser Phe Phe Gly
20

<210> SEQ ID NO 259
<211> LENGTH: 22
<212> TYPE: PRT
<213> ORGANISM: Influenza A virus

<400> SEQUENCE: 259

Asn His Glu Ala Ser Leu Gly Val Ser Ser Ala Ser Pro Tyr Asn Gly
1 5 10 15

Arg Ser Ser Phe Phe Gly
20

<210> SEQ ID NO 260
<211> LENGTH: 22
<212> TYPE: PRT
<213> ORGANISM: Influenza A virus

<400> SEQUENCE: 260

Asn His Glu Ala Ser Leu Gly Val Ser Ser Ala Ser Pro Tyr Leu Gly
1 5 10 15

Arg Ser Ser Phe Phe Gly
20

<210> SEQ ID NO 261
<211> LENGTH: 22
<212> TYPE: PRT
<213> ORGANISM: Influenza A virus

<400> SEQUENCE: 261

Asn His Asp Ala Ser Ser Gly Val Ser Ser Ala Ser Pro Tyr Gln Gly
1 5 10 15

Lys Ser Ser Phe Phe Gly
20

<210> SEQ ID NO 262
<211> LENGTH: 22
<212> TYPE: PRT
<213> ORGANISM: Influenza A virus

<400> SEQUENCE: 262

Asn His Asp Ala Ser Ser Gly Val Ser Ser Ala Ser Pro Tyr Asn Gly
1 5 10 15

Lys Ser Ser Phe Phe Gly
20

<210> SEQ ID NO 263
<211> LENGTH: 22
<212> TYPE: PRT
<213> ORGANISM: Influenza A virus -continued

<400> SEQUENCE: 263

Asn His Asp Ala Ser Ser Gly Val Ser Ser Ala Ser Pro Tyr Leu Gly
1               5                   10                  15

Lys Ser Ser Phe Phe Gly
            20

<210> SEQ ID NO 264
<211> LENGTH: 22
<212> TYPE: PRT
<213> ORGANISM: Influenza A virus

<400> SEQUENCE: 264

Asn His Asp Ala Ser Ser Gly Val Ser Ser Ala Ser Pro Tyr Gln Gly
1               5                   10                  15

Arg Ser Ser Phe Phe Gly
            20

<210> SEQ ID NO 265
<211> LENGTH: 22
<212> TYPE: PRT
<213> ORGANISM: Influenza A virus

<400> SEQUENCE: 265

Asn His Asp Ala Ser Ser Gly Val Ser Ser Ala Ser Pro Tyr Asn Gly
1               5                   10                  15

Arg Ser Ser Phe Phe Gly
            20

<210> SEQ ID NO 266
<211> LENGTH: 22
<212> TYPE: PRT
<213> ORGANISM: Influenza A virus

<400> SEQUENCE: 266

Asn His Asp Ala Ser Ser Gly Val Ser Ser Ala Ser Pro Tyr Leu Gly
1               5                   10                  15

Arg Ser Ser Phe Phe Gly
            20

<210> SEQ ID NO 267
<211> LENGTH: 22
<212> TYPE: PRT
<213> ORGANISM: Influenza A virus

<400> SEQUENCE: 267

Asn His Asp Ala Ser Leu Gly Val Ser Ser Ala Ser Pro Tyr Gln Gly
1               5                   10                  15

Lys Ser Ser Phe Phe Gly
            20

<210> SEQ ID NO 268
<211> LENGTH: 22
<212> TYPE: PRT
<213> ORGANISM: Influenza A virus

<400> SEQUENCE: 268

Asn His Asp Ala Ser Leu Gly Val Ser Ser Ala Ser Pro Tyr Asn Gly
1               5                   10                  15

Lys Ser Ser Phe Phe Gly
            20

-continued

<210> SEQ ID NO 269
<211> LENGTH: 22
<212> TYPE: PRT
<213> ORGANISM: Influenza A virus

<400> SEQUENCE: 269

Asn His Asp Ala Ser Leu Gly Val Ser Ser Ala Ser Pro Tyr Leu Gly
1 5 10 15

Lys Ser Ser Phe Phe Gly
20

<210> SEQ ID NO 270
<211> LENGTH: 22
<212> TYPE: PRT
<213> ORGANISM: Influenza A virus

<400> SEQUENCE: 270

Asn His Asp Ala Ser Leu Gly Val Ser Ser Ala Ser Pro Tyr Gln Gly
1 5 10 15

Arg Ser Ser Phe Phe Gly
20

<210> SEQ ID NO 271
<211> LENGTH: 22
<212> TYPE: PRT
<213> ORGANISM: Influenza A virus

<400> SEQUENCE: 271

Asn His Asp Ala Ser Leu Gly Val Ser Ser Ala Ser Pro Tyr Asn Gly
1 5 10 15

Arg Ser Ser Phe Phe Gly
20

<210> SEQ ID NO 272
<211> LENGTH: 22
<212> TYPE: PRT
<213> ORGANISM: Influenza A virus

<400> SEQUENCE: 272

Asn His Asp Ala Ser Leu Gly Val Ser Ser Ala Ser Pro Tyr Leu Gly
1 5 10 15

Arg Ser Ser Phe Phe Gly
20

<210> SEQ ID NO 273
<211> LENGTH: 18
<212> TYPE: PRT
<213> ORGANISM: Influenza A virus

<400> SEQUENCE: 273

Pro Asn Asp Ala Ala Glu Gln Thr Lys Leu Tyr Gln Asn Pro Thr Thr
1 5 10 15

Tyr Gly

<210> SEQ ID NO 274
<211> LENGTH: 18
<212> TYPE: PRT
<213> ORGANISM: Influenza A virus

<400> SEQUENCE: 274

Pro Asn Asp Ala Ala Glu Gln Thr Lys Leu Tyr Gln Asn Pro Asn Thr
1 5 10 15

-continued

Tyr Gly

<210> SEQ ID NO 275
<211> LENGTH: 18
<212> TYPE: PRT
<213> ORGANISM: Influenza A virus

<400> SEQUENCE: 275

Pro Asn Asp Ala Ala Glu Gln Thr Lys Leu Tyr Gln Asn Ser Thr Thr
1 5 10 15

Tyr Gly

<210> SEQ ID NO 276
<211> LENGTH: 18
<212> TYPE: PRT
<213> ORGANISM: Influenza A virus

<400> SEQUENCE: 276

Pro Asn Asp Ala Ala Glu Gln Thr Lys Leu Tyr Gln Asn Ser Asn Thr
1 5 10 15

Tyr Gly

<210> SEQ ID NO 277
<211> LENGTH: 18
<212> TYPE: PRT
<213> ORGANISM: Influenza A virus

<400> SEQUENCE: 277

Pro Asn Asp Ala Ala Glu Gln Thr Arg Leu Tyr Gln Asn Pro Thr Thr
1 5 10 15

Tyr Gly

<210> SEQ ID NO 278
<211> LENGTH: 18
<212> TYPE: PRT
<213> ORGANISM: Influenza A virus

<400> SEQUENCE: 278

Pro Asn Asp Ala Ala Glu Gln Thr Arg Leu Tyr Gln Asn Pro Asn Thr
1 5 10 15

Tyr Gly

<210> SEQ ID NO 279
<211> LENGTH: 18
<212> TYPE: PRT
<213> ORGANISM: Influenza A virus

<400> SEQUENCE: 279

Pro Asn Asp Ala Ala Glu Gln Thr Arg Leu Tyr Gln Asn Ser Thr Thr
1 5 10 15

Tyr Gly

<210> SEQ ID NO 280
<211> LENGTH: 18
<212> TYPE: PRT
<213> ORGANISM: Influenza A virus

<400> SEQUENCE: 280

Pro Asn Asp Ala Ala Glu Gln Thr Arg Leu Tyr Gln Asn Ser Asn Thr
1 5 10 15

Tyr Gly

-continued

<210> SEQ ID NO 281
<211> LENGTH: 18
<212> TYPE: PRT
<213> ORGANISM: Influenza A virus

<400> SEQUENCE: 281

Pro Asn Asp Ala Ala Glu Gln Ile Lys Leu Tyr Gln Asn Pro Thr Thr
1               5                   10                  15

Tyr Gly

<210> SEQ ID NO 282
<211> LENGTH: 18
<212> TYPE: PRT
<213> ORGANISM: Influenza A virus

<400> SEQUENCE: 282

Pro Asn Asp Ala Ala Glu Gln Ile Lys Leu Tyr Gln Asn Pro Asn Thr
1               5                   10                  15

Tyr Gly

<210> SEQ ID NO 283
<211> LENGTH: 18
<212> TYPE: PRT
<213> ORGANISM: Influenza A virus

<400> SEQUENCE: 283

Pro Asn Asp Ala Ala Glu Gln Ile Lys Leu Tyr Gln Asn Ser Thr Thr
1               5                   10                  15

Tyr Gly

<210> SEQ ID NO 284
<211> LENGTH: 18
<212> TYPE: PRT
<213> ORGANISM: Influenza A virus

<400> SEQUENCE: 284

Pro Asn Asp Ala Ala Glu Gln Ile Lys Leu Tyr Gln Asn Ser Asn Thr
1               5                   10                  15

Tyr Gly

<210> SEQ ID NO 285
<211> LENGTH: 18
<212> TYPE: PRT
<213> ORGANISM: Influenza A virus

<400> SEQUENCE: 285

Pro Asn Asp Ala Ala Glu Gln Ile Arg Leu Tyr Gln Asn Pro Thr Thr
1               5                   10                  15

Tyr Gly

<210> SEQ ID NO 286
<211> LENGTH: 18
<212> TYPE: PRT
<213> ORGANISM: Influenza A virus

<400> SEQUENCE: 286

Pro Asn Asp Ala Ala Glu Gln Ile Arg Leu Tyr Gln Asn Pro Asn Thr
1               5                   10                  15

Tyr Gly

-continued

<210> SEQ ID NO 287
<211> LENGTH: 18
<212> TYPE: PRT
<213> ORGANISM: Influenza A virus

<400> SEQUENCE: 287

Pro Asn Asp Ala Ala Glu Gln Ile Arg Leu Tyr Gln Asn Ser Thr Thr
1 5 10 15

Tyr Gly

<210> SEQ ID NO 288
<211> LENGTH: 18
<212> TYPE: PRT
<213> ORGANISM: Influenza A virus

<400> SEQUENCE: 288

Pro Asn Asp Ala Ala Glu Gln Ile Arg Leu Tyr Gln Asn Ser Asn Thr
1 5 10 15

Tyr Gly

<210> SEQ ID NO 289
<211> LENGTH: 19
<212> TYPE: PRT
<213> ORGANISM: Influenza A virus

<400> SEQUENCE: 289

Ser Trp Ser Asn His Glu Ala Ser Leu Ile Lys Lys Asn Ser Ala Tyr
1 5 10 15

Pro Thr Gly

<210> SEQ ID NO 290
<211> LENGTH: 19
<212> TYPE: PRT
<213> ORGANISM: Influenza A virus

<400> SEQUENCE: 290

Ser Trp Ser Asn His Glu Ala Ser Leu Ile Lys Lys Asn Ser Thr Tyr
1 5 10 15

Pro Thr Gly

<210> SEQ ID NO 291
<211> LENGTH: 19
<212> TYPE: PRT
<213> ORGANISM: Influenza A virus

<400> SEQUENCE: 291

Ser Trp Ser Asn His Glu Ala Ser Leu Ile Lys Lys Asn Ser Val Tyr
1 5 10 15

Pro Thr Gly

<210> SEQ ID NO 292
<211> LENGTH: 19
<212> TYPE: PRT
<213> ORGANISM: Influenza A virus

<400> SEQUENCE: 292

Ser Trp Ser Asn His Glu Ala Ser Leu Ile Lys Lys Asn Asn Ala Tyr
1 5 10 15

Pro Thr Gly

-continued

<210> SEQ ID NO 293
<211> LENGTH: 19
<212> TYPE: PRT
<213> ORGANISM: Influenza A virus

<400> SEQUENCE: 293

Ser Trp Ser Asn His Glu Ala Ser Leu Ile Lys Lys Asn Asn Thr Tyr
1               5                   10                  15

Pro Thr Gly

<210> SEQ ID NO 294
<211> LENGTH: 19
<212> TYPE: PRT
<213> ORGANISM: Influenza A virus

<400> SEQUENCE: 294

Ser Trp Ser Asn His Glu Ala Ser Leu Ile Lys Lys Asn Asn Val Tyr
1               5                   10                  15

Pro Thr Gly

<210> SEQ ID NO 295
<211> LENGTH: 19
<212> TYPE: PRT
<213> ORGANISM: Influenza A virus

<400> SEQUENCE: 295

Ser Trp Ser Asn His Asp Ala Ser Leu Ile Lys Lys Asn Ser Ala Tyr
1               5                   10                  15

Pro Thr Gly

<210> SEQ ID NO 296
<211> LENGTH: 19
<212> TYPE: PRT
<213> ORGANISM: Influenza A virus

<400> SEQUENCE: 296

Ser Trp Ser Asn His Asp Ala Ser Leu Ile Lys Lys Asn Ser Thr Tyr
1               5                   10                  15

Pro Thr Gly

<210> SEQ ID NO 297
<211> LENGTH: 19
<212> TYPE: PRT
<213> ORGANISM: Influenza A virus

<400> SEQUENCE: 297

Ser Trp Ser Asn His Asp Ala Ser Leu Ile Lys Lys Asn Ser Val Tyr
1               5                   10                  15

Pro Thr Gly

<210> SEQ ID NO 298
<211> LENGTH: 19
<212> TYPE: PRT
<213> ORGANISM: Influenza A virus

<400> SEQUENCE: 298

Ser Trp Ser Asn His Asp Ala Ser Leu Ile Lys Lys Asn Asn Ala Tyr
1               5                   10                  15

Pro Thr Gly

<210> SEQ ID NO 299

-continued

<211> LENGTH: 19
<212> TYPE: PRT
<213> ORGANISM: Influenza A virus

<400> SEQUENCE: 299

Ser Trp Ser Asn His Asp Ala Ser Leu Ile Lys Lys Asn Asn Thr Tyr
1 5 10 15

Pro Thr Gly

<210> SEQ ID NO 300
<211> LENGTH: 19
<212> TYPE: PRT
<213> ORGANISM: Influenza A virus

<400> SEQUENCE: 300

Ser Trp Ser Asn His Asp Ala Ser Leu Ile Lys Lys Asn Asn Val Tyr
1 5 10 15

Pro Thr Gly

<210> SEQ ID NO 301
<211> LENGTH: 19
<212> TYPE: PRT
<213> ORGANISM: Influenza A virus

<400> SEQUENCE: 301

Ser Trp Ser Ser His Glu Ala Ser Leu Ile Lys Lys Asn Ser Ala Tyr
1 5 10 15

Pro Thr Gly

<210> SEQ ID NO 302
<211> LENGTH: 19
<212> TYPE: PRT
<213> ORGANISM: Influenza A virus

<400> SEQUENCE: 302

Ser Trp Ser Ser His Glu Ala Ser Leu Ile Lys Lys Asn Ser Thr Tyr
1 5 10 15

Pro Thr Gly

<210> SEQ ID NO 303
<211> LENGTH: 19
<212> TYPE: PRT
<213> ORGANISM: Influenza A virus

<400> SEQUENCE: 303

Ser Trp Ser Ser His Glu Ala Ser Leu Ile Lys Lys Asn Ser Val Tyr
1 5 10 15

Pro Thr Gly

<210> SEQ ID NO 304
<211> LENGTH: 19
<212> TYPE: PRT
<213> ORGANISM: Influenza A virus

<400> SEQUENCE: 304

Ser Trp Ser Ser His Glu Ala Ser Leu Ile Lys Lys Asn Asn Ala Tyr
1 5 10 15

Pro Thr Gly

<210> SEQ ID NO 305
<211> LENGTH: 19

-continued

<212> TYPE: PRT
<213> ORGANISM: Influenza A virus

<400> SEQUENCE: 305

Ser Trp Ser Ser His Glu Ala Ser Leu Ile Lys Lys Asn Asn Thr Tyr
1 5 10 15

Pro Thr Gly

<210> SEQ ID NO 306
<211> LENGTH: 19
<212> TYPE: PRT
<213> ORGANISM: Influenza A virus

<400> SEQUENCE: 306

Ser Trp Ser Ser His Glu Ala Ser Leu Ile Lys Lys Asn Asn Val Tyr
1 5 10 15

Pro Thr Gly

<210> SEQ ID NO 307
<211> LENGTH: 19
<212> TYPE: PRT
<213> ORGANISM: Influenza A virus

<400> SEQUENCE: 307

Ser Trp Ser Ser His Asp Ala Ser Leu Ile Lys Lys Asn Ser Ala Tyr
1 5 10 15

Pro Thr Gly

<210> SEQ ID NO 308
<211> LENGTH: 19
<212> TYPE: PRT
<213> ORGANISM: Influenza A virus

<400> SEQUENCE: 308

Ser Trp Ser Ser His Asp Ala Ser Leu Ile Lys Lys Asn Ser Thr Tyr
1 5 10 15

Pro Thr Gly

<210> SEQ ID NO 309
<211> LENGTH: 19
<212> TYPE: PRT
<213> ORGANISM: Influenza A virus

<400> SEQUENCE: 309

Ser Trp Ser Ser His Asp Ala Ser Leu Ile Lys Lys Asn Ser Val Tyr
1 5 10 15

Pro Thr Gly

<210> SEQ ID NO 310
<211> LENGTH: 19
<212> TYPE: PRT
<213> ORGANISM: Influenza A virus

<400> SEQUENCE: 310

Ser Trp Ser Ser His Asp Ala Ser Leu Ile Lys Lys Asn Asn Ala Tyr
1 5 10 15

Pro Thr Gly

<210> SEQ ID NO 311
<211> LENGTH: 19
<212> TYPE: PRT

-continued

<213> ORGANISM: Influenza A virus

<400> SEQUENCE: 311

Ser Trp Ser Ser His Asp Ala Ser Leu Ile Lys Lys Asn Asn Thr Tyr
1 5 10 15

Pro Thr Gly

<210> SEQ ID NO 312
<211> LENGTH: 19
<212> TYPE: PRT
<213> ORGANISM: Influenza A virus

<400> SEQUENCE: 312

Ser Trp Ser Ser His Asp Ala Ser Leu Ile Lys Lys Asn Asn Val Tyr
1 5 10 15

Pro Thr Gly

<210> SEQ ID NO 313
<211> LENGTH: 24
<212> TYPE: PRT
<213> ORGANISM: Influenza A virus

<400> SEQUENCE: 313

Gly Lys Leu Ser Asp Leu Asp Gly Val Lys Pro Leu Ile Leu Leu Glu
1 5 10 15

Tyr Gly Asn Ser Asn Thr Lys Gly
20

<210> SEQ ID NO 314
<211> LENGTH: 24
<212> TYPE: PRT
<213> ORGANISM: Influenza A virus

<400> SEQUENCE: 314

Gly Lys Leu Ser Asp Leu Lys Gly Val Lys Pro Leu Ile Leu Leu Glu
1 5 10 15

Tyr Gly Asn Ser Asn Thr Lys Gly
20

<210> SEQ ID NO 315
<211> LENGTH: 24
<212> TYPE: PRT
<213> ORGANISM: Influenza A virus

<400> SEQUENCE: 315

Gly Lys Leu Ser Asp Leu Asn Gly Val Lys Pro Leu Ile Leu Leu Glu
1 5 10 15

Tyr Gly Asn Ser Asn Thr Lys Gly
20

<210> SEQ ID NO 316
<211> LENGTH: 24
<212> TYPE: PRT
<213> ORGANISM: Influenza A virus

<400> SEQUENCE: 316

Gly Lys Leu Ser Asp Leu Asp Gly Val Lys Pro Leu Ile Leu Leu Glu
1 5 10 15

Tyr Gly Asn Ser Asn Ala Lys Gly
20

<210> SEQ ID NO 317
<211> LENGTH: 24
<212> TYPE: PRT
<213> ORGANISM: Influenza A virus

<400> SEQUENCE: 317

Gly Lys Leu Ser Asp Leu Lys Gly Val Lys Pro Leu Ile Leu Leu Glu
1 5 10 15

Tyr Gly Asn Ser Asn Ala Lys Gly
20

<210> SEQ ID NO 318
<211> LENGTH: 24
<212> TYPE: PRT
<213> ORGANISM: Influenza A virus

<400> SEQUENCE: 318

Gly Lys Leu Ser Asp Leu Asn Gly Val Lys Pro Leu Ile Leu Leu Glu
1 5 10 15

Tyr Gly Asn Ser Asn Ala Lys Gly
20

<210> SEQ ID NO 319
<211> LENGTH: 24
<212> TYPE: PRT
<213> ORGANISM: Influenza A virus

<400> SEQUENCE: 319

Gly Lys Leu Ser Asp Leu Asp Gly Val Lys Pro Leu Ile Leu Leu Glu
1 5 10 15

Tyr Gly Asn Ser Asp Thr Lys Gly
20

<210> SEQ ID NO 320
<211> LENGTH: 24
<212> TYPE: PRT
<213> ORGANISM: Influenza A virus

<400> SEQUENCE: 320

Gly Lys Leu Ser Asp Leu Lys Gly Val Lys Pro Leu Ile Leu Leu Glu
1 5 10 15

Tyr Gly Asn Ser Asp Thr Lys Gly
20

<210> SEQ ID NO 321
<211> LENGTH: 24
<212> TYPE: PRT
<213> ORGANISM: Influenza A virus

<400> SEQUENCE: 321

Gly Lys Leu Ser Asp Leu Asn Gly Val Lys Pro Leu Ile Leu Leu Glu
1 5 10 15

Tyr Gly Asn Ser Asp Thr Lys Gly
20

<210> SEQ ID NO 322
<211> LENGTH: 24
<212> TYPE: PRT
<213> ORGANISM: Influenza A virus

<400> SEQUENCE: 322

Gly Lys Leu Ser Asp Leu Asp Gly Val Lys Pro Leu Ile Leu Leu Glu
1 5 10 15

Tyr Gly Asn Ser Asp Ala Lys Gly
20

<210> SEQ ID NO 323
<211> LENGTH: 24
<212> TYPE: PRT
<213> ORGANISM: Influenza A virus

<400> SEQUENCE: 323

Gly Lys Leu Ser Asp Leu Lys Gly Val Lys Pro Leu Ile Leu Leu Glu
1 5 10 15

Tyr Gly Asn Ser Asp Ala Lys Gly
20

<210> SEQ ID NO 324
<211> LENGTH: 24
<212> TYPE: PRT
<213> ORGANISM: Influenza A virus

<400> SEQUENCE: 324

Gly Lys Leu Ser Asp Leu Asn Gly Val Lys Pro Leu Ile Leu Leu Glu
1 5 10 15

Tyr Gly Asn Ser Asp Ala Lys Gly
20

<210> SEQ ID NO 325
<211> LENGTH: 24
<212> TYPE: PRT
<213> ORGANISM: Influenza A virus

<400> SEQUENCE: 325

Gly Lys Leu Ser Ser Leu Asp Gly Val Lys Pro Leu Ile Leu Leu Glu
1 5 10 15

Tyr Gly Asn Ser Asn Thr Lys Gly
20

<210> SEQ ID NO 326
<211> LENGTH: 24
<212> TYPE: PRT
<213> ORGANISM: Influenza A virus

<400> SEQUENCE: 326

Gly Lys Leu Ser Ser Leu Lys Gly Val Lys Pro Leu Ile Leu Leu Glu
1 5 10 15

Tyr Gly Asn Ser Asn Thr Lys Gly
20

<210> SEQ ID NO 327
<211> LENGTH: 24
<212> TYPE: PRT
<213> ORGANISM: Influenza A virus

<400> SEQUENCE: 327

Gly Lys Leu Ser Ser Leu Asn Gly Val Lys Pro Leu Ile Leu Leu Glu
1 5 10 15

Tyr Gly Asn Ser Asn Thr Lys Gly
20

<210> SEQ ID NO 328
<211> LENGTH: 24
<212> TYPE: PRT
<213> ORGANISM: Influenza A virus

<400> SEQUENCE: 328

Gly Lys Leu Ser Ser Leu Asp Gly Val Lys Pro Leu Ile Leu Leu Glu
1 5 10 15

Tyr Gly Asn Ser Asn Ala Lys Gly
20

<210> SEQ ID NO 329
<211> LENGTH: 24
<212> TYPE: PRT
<213> ORGANISM: Influenza A virus

<400> SEQUENCE: 329

Gly Lys Leu Ser Ser Leu Lys Gly Val Lys Pro Leu Ile Leu Leu Glu
1 5 10 15

Tyr Gly Asn Ser Asn Ala Lys Gly
20

<210> SEQ ID NO 330
<211> LENGTH: 24
<212> TYPE: PRT
<213> ORGANISM: Influenza A virus

<400> SEQUENCE: 330

Gly Lys Leu Ser Ser Leu Asn Gly Val Lys Pro Leu Ile Leu Leu Glu
1 5 10 15

Tyr Gly Asn Ser Asn Ala Lys Gly
20

<210> SEQ ID NO 331
<211> LENGTH: 24
<212> TYPE: PRT
<213> ORGANISM: Influenza A virus

<400> SEQUENCE: 331

Gly Lys Leu Ser Ser Leu Asp Gly Val Lys Pro Leu Ile Leu Leu Glu
1 5 10 15

Tyr Gly Asn Ser Asp Thr Lys Gly
20

<210> SEQ ID NO 332
<211> LENGTH: 24
<212> TYPE: PRT
<213> ORGANISM: Influenza A virus

<400> SEQUENCE: 332

Gly Lys Leu Ser Ser Leu Lys Gly Val Lys Pro Leu Ile Leu Leu Glu
1 5 10 15

Tyr Gly Asn Ser Asp Thr Lys Gly
20

<210> SEQ ID NO 333
<211> LENGTH: 24
<212> TYPE: PRT
<213> ORGANISM: Influenza A virus

<400> SEQUENCE: 333

Gly Lys Leu Ser Ser Leu Asn Gly Val Lys Pro Leu Ile Leu Leu Glu
1 5 10 15

Tyr Gly Asn Ser Asp Thr Lys Gly
20

<210> SEQ ID NO 334
<211> LENGTH: 24
<212> TYPE: PRT
<213> ORGANISM: Influenza A virus

<400> SEQUENCE: 334

Gly Lys Leu Ser Ser Leu Asp Gly Val Lys Pro Leu Ile Leu Leu Glu
1 5 10 15

Tyr Gly Asn Ser Asp Ala Lys Gly
20

<210> SEQ ID NO 335
<211> LENGTH: 24
<212> TYPE: PRT
<213> ORGANISM: Influenza A virus

<400> SEQUENCE: 335

Gly Lys Leu Ser Ser Leu Lys Gly Val Lys Pro Leu Ile Leu Leu Glu
1 5 10 15

Tyr Gly Asn Ser Asp Ala Lys Gly
20

<210> SEQ ID NO 336
<211> LENGTH: 24
<212> TYPE: PRT
<213> ORGANISM: Influenza A virus

<400> SEQUENCE: 336

Gly Lys Leu Ser Ser Leu Asn Gly Val Lys Pro Leu Ile Leu Leu Glu
1 5 10 15

Tyr Gly Asn Ser Asp Ala Lys Gly
20

<210> SEQ ID NO 337
<211> LENGTH: 25
<212> TYPE: PRT
<213> ORGANISM: Influenza A virus

<400> SEQUENCE: 337

Thr Ile Lys Arg Ser Tyr Asn Asn Thr Asn Gln Glu Asp Lys Pro Asn
1 5 10 15

Asp Ala Ile Asn Phe Glu Ser Asn Gly
20 25

<210> SEQ ID NO 338
<211> LENGTH: 25
<212> TYPE: PRT
<213> ORGANISM: Influenza A virus

<400> SEQUENCE: 338

Thr Ile Lys Arg Ser Tyr Asn Asn Thr Asn Gln Glu Asp Lys Pro Asn
1 5 10 15

Asp Ala Ile Asn Phe Glu Ser Thr Gly
20 25

<210> SEQ ID NO 339
<211> LENGTH: 25
<212> TYPE: PRT
<213> ORGANISM: Influenza A virus

<400> SEQUENCE: 339

Thr Ile Lys Arg Ser Tyr Asn Asn Thr Asn Gln Glu Asp Lys Pro Asn

-continued

```
1               5                   10                  15

Asp Ser Ile Asn Phe Glu Ser Asn Gly
            20                  25


<210> SEQ ID NO 340
<211> LENGTH: 25
<212> TYPE: PRT
<213> ORGANISM: Influenza A virus

<400> SEQUENCE: 340

Thr Ile Lys Arg Ser Tyr Asn Asn Thr Asn Gln Glu Asp Lys Pro Asn
1               5                   10                  15

Asp Ser Ile Asn Phe Glu Ser Thr Gly
            20                  25


<210> SEQ ID NO 341
<211> LENGTH: 25
<212> TYPE: PRT
<213> ORGANISM: Influenza A virus

<400> SEQUENCE: 341

Thr Ile Lys Arg Ser Tyr Asn Asn Thr Asn Gln Glu Asp Arg Pro Asn
1               5                   10                  15

Asp Ala Ile Asn Phe Glu Ser Asn Gly
            20                  25


<210> SEQ ID NO 342
<211> LENGTH: 25
<212> TYPE: PRT
<213> ORGANISM: Influenza A virus

<400> SEQUENCE: 342

Thr Ile Lys Arg Ser Tyr Asn Asn Thr Asn Gln Glu Asp Arg Pro Asn
1               5                   10                  15

Asp Ala Ile Asn Phe Glu Ser Thr Gly
            20                  25


<210> SEQ ID NO 343
<211> LENGTH: 25
<212> TYPE: PRT
<213> ORGANISM: Influenza A virus

<400> SEQUENCE: 343

Thr Ile Lys Arg Ser Tyr Asn Asn Thr Asn Gln Glu Asp Arg Pro Asn
1               5                   10                  15

Asp Ser Ile Asn Phe Glu Ser Asn Gly
            20                  25


<210> SEQ ID NO 344
<211> LENGTH: 25
<212> TYPE: PRT
<213> ORGANISM: Influenza A virus

<400> SEQUENCE: 344

Thr Ile Lys Arg Ser Tyr Asn Asn Thr Asn Gln Glu Asp Arg Pro Asn
1               5                   10                  15

Asp Ser Ile Asn Phe Glu Ser Thr Gly
            20                  25


<210> SEQ ID NO 345
<211> LENGTH: 25
<212> TYPE: PRT
```

-continued

<213> ORGANISM: Influenza A virus

<400> SEQUENCE: 345

Thr Ile Lys Arg Ser Tyr Asn Asn Thr Asn Val Glu Asp Lys Pro Asn
1 5 10 15

Asp Ala Ile Asn Phe Glu Ser Asn Gly
20 25

<210> SEQ ID NO 346
<211> LENGTH: 25
<212> TYPE: PRT
<213> ORGANISM: Influenza A virus

<400> SEQUENCE: 346

Thr Ile Lys Arg Ser Tyr Asn Asn Thr Asn Val Glu Asp Lys Pro Asn
1 5 10 15

Asp Ala Ile Asn Phe Glu Ser Thr Gly
20 25

<210> SEQ ID NO 347
<211> LENGTH: 25
<212> TYPE: PRT
<213> ORGANISM: Influenza A virus

<400> SEQUENCE: 347

Thr Ile Lys Arg Ser Tyr Asn Asn Thr Asn Val Glu Asp Lys Pro Asn
1 5 10 15

Asp Ser Ile Asn Phe Glu Ser Asn Gly
20 25

<210> SEQ ID NO 348
<211> LENGTH: 25
<212> TYPE: PRT
<213> ORGANISM: Influenza A virus

<400> SEQUENCE: 348

Thr Ile Lys Arg Ser Tyr Asn Asn Thr Asn Val Glu Asp Lys Pro Asn
1 5 10 15

Asp Ser Ile Asn Phe Glu Ser Thr Gly
20 25

<210> SEQ ID NO 349
<211> LENGTH: 25
<212> TYPE: PRT
<213> ORGANISM: Influenza A virus

<400> SEQUENCE: 349

Thr Ile Lys Arg Ser Tyr Asn Asn Thr Asn Val Glu Asp Arg Pro Asn
1 5 10 15

Asp Ala Ile Asn Phe Glu Ser Asn Gly
20 25

<210> SEQ ID NO 350
<211> LENGTH: 25
<212> TYPE: PRT
<213> ORGANISM: Influenza A virus

<400> SEQUENCE: 350

Thr Ile Lys Arg Ser Tyr Asn Asn Thr Asn Val Glu Asp Arg Pro Asn
1 5 10 15

Asp Ala Ile Asn Phe Glu Ser Thr Gly
20 25

-continued

<210> SEQ ID NO 351
<211> LENGTH: 25
<212> TYPE: PRT
<213> ORGANISM: Influenza A virus

<400> SEQUENCE: 351

```
Thr Ile Lys Arg Ser Tyr Asn Asn Thr Asn Val Glu Asp Arg Pro Asn
1               5                   10                  15

Asp Ser Ile Asn Phe Glu Ser Asn Gly
            20                  25
```

<210> SEQ ID NO 352
<211> LENGTH: 25
<212> TYPE: PRT
<213> ORGANISM: Influenza A virus

<400> SEQUENCE: 352

```
Thr Ile Lys Arg Ser Tyr Asn Asn Thr Asn Val Glu Asp Arg Pro Asn
1               5                   10                  15

Asp Ser Ile Asn Phe Glu Ser Thr Gly
            20                  25
```

<210> SEQ ID NO 353
<211> LENGTH: 25
<212> TYPE: PRT
<213> ORGANISM: Influenza A virus

<400> SEQUENCE: 353

```
Thr Ile Lys Arg Thr Tyr Asn Asn Thr Asn Gln Glu Asp Lys Pro Asn
1               5                   10                  15

Asp Ala Ile Asn Phe Glu Ser Asn Gly
            20                  25
```

<210> SEQ ID NO 354
<211> LENGTH: 25
<212> TYPE: PRT
<213> ORGANISM: Influenza A virus

<400> SEQUENCE: 354

```
Thr Ile Lys Arg Thr Tyr Asn Asn Thr Asn Gln Glu Asp Lys Pro Asn
1               5                   10                  15

Asp Ala Ile Asn Phe Glu Ser Thr Gly
            20                  25
```

<210> SEQ ID NO 355
<211> LENGTH: 25
<212> TYPE: PRT
<213> ORGANISM: Influenza A virus

<400> SEQUENCE: 355

```
Thr Ile Lys Arg Thr Tyr Asn Asn Thr Asn Gln Glu Asp Lys Pro Asn
1               5                   10                  15

Asp Ser Ile Asn Phe Glu Ser Asn Gly
            20                  25
```

<210> SEQ ID NO 356
<211> LENGTH: 25
<212> TYPE: PRT
<213> ORGANISM: Influenza A virus

<400> SEQUENCE: 356

-continued

```
Thr Ile Lys Arg Thr Tyr Asn Asn Thr Asn Gln Glu Asp Lys Pro Asn
1               5                   10                  15

Asp Ser Ile Asn Phe Glu Ser Thr Gly
            20                  25


<210> SEQ ID NO 357
<211> LENGTH: 25
<212> TYPE: PRT
<213> ORGANISM: Influenza A virus

<400> SEQUENCE: 357

Thr Ile Lys Arg Thr Tyr Asn Asn Thr Asn Gln Glu Asp Arg Pro Asn
1               5                   10                  15

Asp Ala Ile Asn Phe Glu Ser Asn Gly
            20                  25


<210> SEQ ID NO 358
<211> LENGTH: 25
<212> TYPE: PRT
<213> ORGANISM: Influenza A virus

<400> SEQUENCE: 358

Thr Ile Lys Arg Thr Tyr Asn Asn Thr Asn Gln Glu Asp Arg Pro Asn
1               5                   10                  15

Asp Ala Ile Asn Phe Glu Ser Thr Gly
            20                  25


<210> SEQ ID NO 359
<211> LENGTH: 25
<212> TYPE: PRT
<213> ORGANISM: Influenza A virus

<400> SEQUENCE: 359

Thr Ile Lys Arg Thr Tyr Asn Asn Thr Asn Gln Glu Asp Arg Pro Asn
1               5                   10                  15

Asp Ser Ile Asn Phe Glu Ser Asn Gly
            20                  25


<210> SEQ ID NO 360
<211> LENGTH: 25
<212> TYPE: PRT
<213> ORGANISM: Influenza A virus

<400> SEQUENCE: 360

Thr Ile Lys Arg Thr Tyr Asn Asn Thr Asn Gln Glu Asp Arg Pro Asn
1               5                   10                  15

Asp Ser Ile Asn Phe Glu Ser Thr Gly
            20                  25


<210> SEQ ID NO 361
<211> LENGTH: 25
<212> TYPE: PRT
<213> ORGANISM: Influenza A virus

<400> SEQUENCE: 361

Thr Ile Lys Arg Thr Tyr Asn Asn Thr Asn Val Glu Asp Lys Pro Asn
1               5                   10                  15

Asp Ala Ile Asn Phe Glu Ser Asn Gly
            20                  25


<210> SEQ ID NO 362
<211> LENGTH: 25
```

-continued

<212> TYPE: PRT
<213> ORGANISM: Influenza A virus

<400> SEQUENCE: 362

Thr Ile Lys Arg Thr Tyr Asn Asn Thr Asn Val Glu Asp Lys Pro Asn
1 5 10 15

Asp Ala Ile Asn Phe Glu Ser Thr Gly
20 25

<210> SEQ ID NO 363
<211> LENGTH: 25
<212> TYPE: PRT
<213> ORGANISM: Influenza A virus

<400> SEQUENCE: 363

Thr Ile Lys Arg Thr Tyr Asn Asn Thr Asn Val Glu Asp Lys Pro Asn
1 5 10 15

Asp Ser Ile Asn Phe Glu Ser Asn Gly
20 25

<210> SEQ ID NO 364
<211> LENGTH: 25
<212> TYPE: PRT
<213> ORGANISM: Influenza A virus

<400> SEQUENCE: 364

Thr Ile Lys Arg Thr Tyr Asn Asn Thr Asn Val Glu Asp Lys Pro Asn
1 5 10 15

Asp Ser Ile Asn Phe Glu Ser Thr Gly
20 25

<210> SEQ ID NO 365
<211> LENGTH: 25
<212> TYPE: PRT
<213> ORGANISM: Influenza A virus

<400> SEQUENCE: 365

Thr Ile Lys Arg Thr Tyr Asn Asn Thr Asn Val Glu Asp Arg Pro Asn
1 5 10 15

Asp Ala Ile Asn Phe Glu Ser Asn Gly
20 25

<210> SEQ ID NO 366
<211> LENGTH: 25
<212> TYPE: PRT
<213> ORGANISM: Influenza A virus

<400> SEQUENCE: 366

Thr Ile Lys Arg Thr Tyr Asn Asn Thr Asn Val Glu Asp Arg Pro Asn
1 5 10 15

Asp Ala Ile Asn Phe Glu Ser Thr Gly
20 25

<210> SEQ ID NO 367
<211> LENGTH: 25
<212> TYPE: PRT
<213> ORGANISM: Influenza A virus

<400> SEQUENCE: 367

Thr Ile Lys Arg Thr Tyr Asn Asn Thr Asn Val Glu Asp Arg Pro Asn
1 5 10 15

Asp Ser Ile Asn Phe Glu Ser Asn Gly

-continued 20 25

<210> SEQ ID NO 368
<211> LENGTH: 25
<212> TYPE: PRT
<213> ORGANISM: Influenza A virus

<400> SEQUENCE: 368

Thr Ile Lys Arg Thr Tyr Asn Asn Thr Asn Val Glu Asp Arg Pro Asn
1 5 10 15

Asp Ser Ile Asn Phe Glu Ser Thr Gly
20 25

<210> SEQ ID NO 369
<211> LENGTH: 17
<212> TYPE: PRT
<213> ORGANISM: Influenza A virus

<400> SEQUENCE: 369

Ile Ser Val Gly Thr Ser Thr Leu Asn Gln Arg Leu Val Pro Lys Ile
1 5 10 15

Gly

<210> SEQ ID NO 370
<211> LENGTH: 17
<212> TYPE: PRT
<213> ORGANISM: Influenza A virus

<400> SEQUENCE: 370

Ile Ser Val Gly Thr Ser Thr Leu Asn Gln Arg Leu Val Pro Glu Ile
1 5 10 15

Gly

<210> SEQ ID NO 371
<211> LENGTH: 17
<212> TYPE: PRT
<213> ORGANISM: Influenza A virus

<400> SEQUENCE: 371

Ile Ser Val Gly Thr Ser Thr Leu Asn Gln Arg Leu Val Pro Arg Ile
1 5 10 15

Gly

<210> SEQ ID NO 372
<211> LENGTH: 17
<212> TYPE: PRT
<213> ORGANISM: Influenza A virus

<400> SEQUENCE: 372

Ile Ser Val Gly Thr Ser Thr Leu Asn Gln Arg Leu Ile Pro Lys Ile
1 5 10 15

Gly

<210> SEQ ID NO 373
<211> LENGTH: 17
<212> TYPE: PRT
<213> ORGANISM: Influenza A virus

<400> SEQUENCE: 373

Ile Ser Val Gly Thr Ser Thr Leu Asn Gln Arg Leu Ile Pro Glu Ile
1 5 10 15

-continued

Gly

<210> SEQ ID NO 374
<211> LENGTH: 17
<212> TYPE: PRT
<213> ORGANISM: Influenza A virus

<400> SEQUENCE: 374

Ile Ser Val Gly Thr Ser Thr Leu Asn Gln Arg Leu Ile Pro Arg Ile
1 5 10 15

Gly

<210> SEQ ID NO 375
<211> LENGTH: 17
<212> TYPE: PRT
<213> ORGANISM: Influenza A virus

<400> SEQUENCE: 375

Ile Ser Val Gly Thr Ser Thr Leu Asn Gln Arg Ser Val Pro Lys Ile
1 5 10 15

Gly

<210> SEQ ID NO 376
<211> LENGTH: 17
<212> TYPE: PRT
<213> ORGANISM: Influenza A virus

<400> SEQUENCE: 376

Ile Ser Val Gly Thr Ser Thr Leu Asn Gln Arg Ser Val Pro Glu Ile
1 5 10 15

Gly

<210> SEQ ID NO 377
<211> LENGTH: 17
<212> TYPE: PRT
<213> ORGANISM: Influenza A virus

<400> SEQUENCE: 377

Ile Ser Val Gly Thr Ser Thr Leu Asn Gln Arg Ser Val Pro Arg Ile
1 5 10 15

Gly

<210> SEQ ID NO 378
<211> LENGTH: 17
<212> TYPE: PRT
<213> ORGANISM: Influenza A virus

<400> SEQUENCE: 378

Ile Ser Val Gly Thr Ser Thr Leu Asn Gln Arg Ser Ile Pro Lys Ile
1 5 10 15

Gly

<210> SEQ ID NO 379
<211> LENGTH: 17
<212> TYPE: PRT
<213> ORGANISM: Influenza A virus

<400> SEQUENCE: 379

Ile Ser Val Gly Thr Ser Thr Leu Asn Gln Arg Ser Ile Pro Glu Ile
1 5 10 15

Gly

-continued

<210> SEQ ID NO 380
<211> LENGTH: 17
<212> TYPE: PRT
<213> ORGANISM: Influenza A virus

<400> SEQUENCE: 380

Ile Ser Val Gly Thr Ser Thr Leu Asn Gln Arg Ser Ile Pro Arg Ile
1 5 10 15

Gly

<210> SEQ ID NO 381
<211> LENGTH: 17
<212> TYPE: PRT
<213> ORGANISM: Influenza A virus

<400> SEQUENCE: 381

Val Ser Val Gly Thr Ser Thr Leu Asn Gln Arg Leu Val Pro Lys Ile
1 5 10 15

Gly

<210> SEQ ID NO 382
<211> LENGTH: 17
<212> TYPE: PRT
<213> ORGANISM: Influenza A virus

<400> SEQUENCE: 382

Val Ser Val Gly Thr Ser Thr Leu Asn Gln Arg Leu Val Pro Glu Ile
1 5 10 15

Gly

<210> SEQ ID NO 383
<211> LENGTH: 17
<212> TYPE: PRT
<213> ORGANISM: Influenza A virus

<400> SEQUENCE: 383

Val Ser Val Gly Thr Ser Thr Leu Asn Gln Arg Leu Val Pro Arg Ile
1 5 10 15

Gly

<210> SEQ ID NO 384
<211> LENGTH: 17
<212> TYPE: PRT
<213> ORGANISM: Influenza A virus

<400> SEQUENCE: 384

Val Ser Val Gly Thr Ser Thr Leu Asn Gln Arg Leu Ile Pro Lys Ile
1 5 10 15

Gly

<210> SEQ ID NO 385
<211> LENGTH: 17
<212> TYPE: PRT
<213> ORGANISM: Influenza A virus

<400> SEQUENCE: 385

Val Ser Val Gly Thr Ser Thr Leu Asn Gln Arg Leu Ile Pro Glu Ile
1 5 10 15

Gly

-continued

<210> SEQ ID NO 386
<211> LENGTH: 17
<212> TYPE: PRT
<213> ORGANISM: Influenza A virus

<400> SEQUENCE: 386

Val Ser Val Gly Thr Ser Thr Leu Asn Gln Arg Leu Ile Pro Arg Ile
1 5 10 15

Gly

<210> SEQ ID NO 387
<211> LENGTH: 17
<212> TYPE: PRT
<213> ORGANISM: Influenza A virus

<400> SEQUENCE: 387

Val Ser Val Gly Thr Ser Thr Leu Asn Gln Arg Ser Val Pro Lys Ile
1 5 10 15

Gly

<210> SEQ ID NO 388
<211> LENGTH: 17
<212> TYPE: PRT
<213> ORGANISM: Influenza A virus

<400> SEQUENCE: 388

Val Ser Val Gly Thr Ser Thr Leu Asn Gln Arg Ser Val Pro Glu Ile
1 5 10 15

Gly

<210> SEQ ID NO 389
<211> LENGTH: 17
<212> TYPE: PRT
<213> ORGANISM: Influenza A virus

<400> SEQUENCE: 389

Val Ser Val Gly Thr Ser Thr Leu Asn Gln Arg Ser Val Pro Arg Ile
1 5 10 15

Gly

<210> SEQ ID NO 390
<211> LENGTH: 17
<212> TYPE: PRT
<213> ORGANISM: Influenza A virus

<400> SEQUENCE: 390

Val Ser Val Gly Thr Ser Thr Leu Asn Gln Arg Ser Ile Pro Lys Ile
1 5 10 15

Gly

<210> SEQ ID NO 391
<211> LENGTH: 17
<212> TYPE: PRT
<213> ORGANISM: Influenza A virus

<400> SEQUENCE: 391

Val Ser Val Gly Thr Ser Thr Leu Asn Gln Arg Ser Ile Pro Glu Ile
1 5 10 15

Gly

-continued

<210> SEQ ID NO 392
<211> LENGTH: 17
<212> TYPE: PRT
<213> ORGANISM: Influenza A virus

<400> SEQUENCE: 392

Val Ser Val Gly Thr Ser Thr Leu Asn Gln Arg Ser Ile Pro Arg Ile
1 5 10 15

Gly

<210> SEQ ID NO 393
<211> LENGTH: 23
<212> TYPE: PRT
<213> ORGANISM: Influenza A virus

<400> SEQUENCE: 393

Lys Ala Asn Pro Ala Asn Asp Leu Gly Asn Pro Met Ser Asp Glu Phe
1 5 10 15

Ile Asn Val Pro Glu Trp Gly
20

<210> SEQ ID NO 394
<211> LENGTH: 23
<212> TYPE: PRT
<213> ORGANISM: Influenza A virus

<400> SEQUENCE: 394

Lys Ala Asn Pro Ala Asn Asp Leu Gly Asn Pro Met Ser Asp Glu Phe
1 5 10 15

Leu Asn Val Pro Glu Trp Gly
20

<210> SEQ ID NO 395
<211> LENGTH: 23
<212> TYPE: PRT
<213> ORGANISM: Influenza A virus

<400> SEQUENCE: 395

Lys Ala Asn Pro Ala Asn Gly Leu Gly Asn Pro Met Ser Asp Glu Phe
1 5 10 15

Ile Asn Val Pro Glu Trp Gly
20

<210> SEQ ID NO 396
<211> LENGTH: 23
<212> TYPE: PRT
<213> ORGANISM: Influenza A virus

<400> SEQUENCE: 396

Lys Ala Asn Pro Ala Asn Gly Leu Gly Asn Pro Met Ser Asp Glu Phe
1 5 10 15

Leu Asn Val Pro Glu Trp Gly
20

<210> SEQ ID NO 397
<211> LENGTH: 23
<212> TYPE: PRT
<213> ORGANISM: Influenza A virus

<400> SEQUENCE: 397

Lys Ala Asn Pro Val Asn Asp Leu Gly Asn Pro Met Ser Asp Glu Phe
1 5 10 15

-continued

Ile Asn Val Pro Glu Trp Gly
20

<210> SEQ ID NO 398
<211> LENGTH: 23
<212> TYPE: PRT
<213> ORGANISM: Influenza A virus

<400> SEQUENCE: 398

Lys Ala Asn Pro Val Asn Asp Leu Gly Asn Pro Met Ser Asp Glu Phe
1 5 10 15

Leu Asn Val Pro Glu Trp Gly
20

<210> SEQ ID NO 399
<211> LENGTH: 23
<212> TYPE: PRT
<213> ORGANISM: Influenza A virus

<400> SEQUENCE: 399

Lys Ala Asn Pro Val Asn Gly Leu Gly Asn Pro Met Ser Asp Glu Phe
1 5 10 15

Ile Asn Val Pro Glu Trp Gly
20

<210> SEQ ID NO 400
<211> LENGTH: 23
<212> TYPE: PRT
<213> ORGANISM: Influenza A virus

<400> SEQUENCE: 400

Lys Ala Asn Pro Val Asn Gly Leu Gly Asn Pro Met Ser Asp Glu Phe
1 5 10 15

Leu Asn Val Pro Glu Trp Gly
20

<210> SEQ ID NO 401
<211> LENGTH: 23
<212> TYPE: PRT
<213> ORGANISM: Influenza A virus

<400> SEQUENCE: 401

Lys Ala Ser Pro Ala Asn Asp Leu Gly Asn Pro Met Ser Asp Glu Phe
1 5 10 15

Ile Asn Val Pro Glu Trp Gly
20

<210> SEQ ID NO 402
<211> LENGTH: 23
<212> TYPE: PRT
<213> ORGANISM: Influenza A virus

<400> SEQUENCE: 402

Lys Ala Ser Pro Ala Asn Asp Leu Gly Asn Pro Met Ser Asp Glu Phe
1 5 10 15

Leu Asn Val Pro Glu Trp Gly
20

<210> SEQ ID NO 403
<211> LENGTH: 23
<212> TYPE: PRT
<213> ORGANISM: Influenza A virus -continued

<400> SEQUENCE: 403

Lys Ala Ser Pro Ala Asn Gly Leu Gly Asn Pro Met Ser Asp Glu Phe
1 5 10 15

Ile Asn Val Pro Glu Trp Gly
20

<210> SEQ ID NO 404
<211> LENGTH: 23
<212> TYPE: PRT
<213> ORGANISM: Influenza A virus

<400> SEQUENCE: 404

Lys Ala Ser Pro Ala Asn Gly Leu Gly Asn Pro Met Ser Asp Glu Phe
1 5 10 15

Leu Asn Val Pro Glu Trp Gly
20

<210> SEQ ID NO 405
<211> LENGTH: 23
<212> TYPE: PRT
<213> ORGANISM: Influenza A virus

<400> SEQUENCE: 405

Lys Ala Ser Pro Val Asn Asp Leu Gly Asn Pro Met Ser Asp Glu Phe
1 5 10 15

Ile Asn Val Pro Glu Trp Gly
20

<210> SEQ ID NO 406
<211> LENGTH: 23
<212> TYPE: PRT
<213> ORGANISM: Influenza A virus

<400> SEQUENCE: 406

Lys Ala Ser Pro Val Asn Asp Leu Gly Asn Pro Met Ser Asp Glu Phe
1 5 10 15

Leu Asn Val Pro Glu Trp Gly
20

<210> SEQ ID NO 407
<211> LENGTH: 23
<212> TYPE: PRT
<213> ORGANISM: Influenza A virus

<400> SEQUENCE: 407

Lys Ala Ser Pro Val Asn Gly Leu Gly Asn Pro Met Ser Asp Glu Phe
1 5 10 15

Ile Asn Val Pro Glu Trp Gly
20

<210> SEQ ID NO 408
<211> LENGTH: 23
<212> TYPE: PRT
<213> ORGANISM: Influenza A virus

<400> SEQUENCE: 408

Lys Ala Ser Pro Val Asn Gly Leu Gly Asn Pro Met Ser Asp Glu Phe
1 5 10 15

Leu Asn Val Pro Glu Trp Gly
20

-continued

<210> SEQ ID NO 409
<211> LENGTH: 23
<212> TYPE: PRT
<213> ORGANISM: Influenza A virus

<400> SEQUENCE: 409

```
Lys Asp Asn Pro Ala Asn Asp Leu Gly Asn Pro Met Ser Asp Glu Phe
1               5                   10                  15

Ile Asn Val Pro Glu Trp Gly
            20
```

<210> SEQ ID NO 410
<211> LENGTH: 23
<212> TYPE: PRT
<213> ORGANISM: Influenza A virus

<400> SEQUENCE: 410

```
Lys Asp Asn Pro Ala Asn Asp Leu Gly Asn Pro Met Ser Asp Glu Phe
1               5                   10                  15

Leu Asn Val Pro Glu Trp Gly
            20
```

<210> SEQ ID NO 411
<211> LENGTH: 23
<212> TYPE: PRT
<213> ORGANISM: Influenza A virus

<400> SEQUENCE: 411

```
Lys Asp Asn Pro Ala Asn Gly Leu Gly Asn Pro Met Ser Asp Glu Phe
1               5                   10                  15

Ile Asn Val Pro Glu Trp Gly
            20
```

<210> SEQ ID NO 412
<211> LENGTH: 23
<212> TYPE: PRT
<213> ORGANISM: Influenza A virus

<400> SEQUENCE: 412

```
Lys Asp Asn Pro Ala Asn Gly Leu Gly Asn Pro Met Ser Asp Glu Phe
1               5                   10                  15

Leu Asn Val Pro Glu Trp Gly
            20
```

<210> SEQ ID NO 413
<211> LENGTH: 23
<212> TYPE: PRT
<213> ORGANISM: Influenza A virus

<400> SEQUENCE: 413

```
Lys Asp Asn Pro Val Asn Asp Leu Gly Asn Pro Met Ser Asp Glu Phe
1               5                   10                  15

Ile Asn Val Pro Glu Trp Gly
            20
```

<210> SEQ ID NO 414
<211> LENGTH: 23
<212> TYPE: PRT
<213> ORGANISM: Influenza A virus

<400> SEQUENCE: 414

```
Lys Asp Asn Pro Val Asn Asp Leu Gly Asn Pro Met Ser Asp Glu Phe
1               5                   10                  15
```

```
Leu Asn Val Pro Glu Trp Gly
            20


<210> SEQ ID NO 415
<211> LENGTH: 23
<212> TYPE: PRT
<213> ORGANISM: Influenza A virus

<400> SEQUENCE: 415

Lys Asp Asn Pro Val Asn Gly Leu Gly Asn Pro Met Ser Asp Glu Phe
1               5                   10                  15

Ile Asn Val Pro Glu Trp Gly
            20


<210> SEQ ID NO 416
<211> LENGTH: 23
<212> TYPE: PRT
<213> ORGANISM: Influenza A virus

<400> SEQUENCE: 416

Lys Asp Asn Pro Val Asn Gly Leu Gly Asn Pro Met Ser Asp Glu Phe
1               5                   10                  15

Leu Asn Val Pro Glu Trp Gly
            20


<210> SEQ ID NO 417
<211> LENGTH: 23
<212> TYPE: PRT
<213> ORGANISM: Influenza A virus

<400> SEQUENCE: 417

Lys Asp Ser Pro Ala Asn Asp Leu Gly Asn Pro Met Ser Asp Glu Phe
1               5                   10                  15

Ile Asn Val Pro Glu Trp Gly
            20


<210> SEQ ID NO 418
<211> LENGTH: 23
<212> TYPE: PRT
<213> ORGANISM: Influenza A virus

<400> SEQUENCE: 418

Lys Asp Ser Pro Ala Asn Asp Leu Gly Asn Pro Met Ser Asp Glu Phe
1               5                   10                  15

Leu Asn Val Pro Glu Trp Gly
            20


<210> SEQ ID NO 419
<211> LENGTH: 23
<212> TYPE: PRT
<213> ORGANISM: Influenza A virus

<400> SEQUENCE: 419

Lys Asp Ser Pro Ala Asn Gly Leu Gly Asn Pro Met Ser Asp Glu Phe
1               5                   10                  15

Ile Asn Val Pro Glu Trp Gly
            20


<210> SEQ ID NO 420
<211> LENGTH: 23
<212> TYPE: PRT
<213> ORGANISM: Influenza A virus
```

-continued

<400> SEQUENCE: 420

Lys Asp Ser Pro Ala Asn Gly Leu Gly Asn Pro Met Ser Asp Glu Phe
1               5                   10                  15

Leu Asn Val Pro Glu Trp Gly
            20

<210> SEQ ID NO 421
<211> LENGTH: 23
<212> TYPE: PRT
<213> ORGANISM: Influenza A virus

<400> SEQUENCE: 421

Lys Asp Ser Pro Val Asn Asp Leu Gly Asn Pro Met Ser Asp Glu Phe
1               5                   10                  15

Ile Asn Val Pro Glu Trp Gly
            20

<210> SEQ ID NO 422
<211> LENGTH: 23
<212> TYPE: PRT
<213> ORGANISM: Influenza A virus

<400> SEQUENCE: 422

Lys Asp Ser Pro Val Asn Asp Leu Gly Asn Pro Met Ser Asp Glu Phe
1               5                   10                  15

Leu Asn Val Pro Glu Trp Gly
            20

<210> SEQ ID NO 423
<211> LENGTH: 23
<212> TYPE: PRT
<213> ORGANISM: Influenza A virus

<400> SEQUENCE: 423

Lys Asp Ser Pro Val Asn Gly Leu Gly Asn Pro Met Ser Asp Glu Phe
1               5                   10                  15

Ile Asn Val Pro Glu Trp Gly
            20

<210> SEQ ID NO 424
<211> LENGTH: 23
<212> TYPE: PRT
<213> ORGANISM: Influenza A virus

<400> SEQUENCE: 424

Lys Asp Ser Pro Val Asn Gly Leu Gly Asn Pro Met Ser Asp Glu Phe
1               5                   10                  15

Leu Asn Val Pro Glu Trp Gly
            20

<210> SEQ ID NO 425
<211> LENGTH: 23
<212> TYPE: PRT
<213> ORGANISM: Influenza A virus

<400> SEQUENCE: 425

Pro Tyr Gln Gly Lys Ser Ser Phe Phe Arg Asn Val Val Trp Leu Ile
1               5                   10                  15

Lys Lys Asn Ser Ala Tyr Gly
            20

-continued

<210> SEQ ID NO 426
<211> LENGTH: 23
<212> TYPE: PRT
<213> ORGANISM: Influenza A virus

<400> SEQUENCE: 426

Pro Tyr Gln Gly Lys Ser Ser Phe Phe Arg Asn Val Val Trp Leu Ile
1 5 10 15

Lys Lys Asn Ser Thr Tyr Gly
20

<210> SEQ ID NO 427
<211> LENGTH: 23
<212> TYPE: PRT
<213> ORGANISM: Influenza A virus

<400> SEQUENCE: 427

Pro Tyr Gln Gly Lys Ser Ser Phe Phe Arg Asn Val Val Trp Leu Ile
1 5 10 15

Lys Lys Asn Ser Val Tyr Gly
20

<210> SEQ ID NO 428
<211> LENGTH: 23
<212> TYPE: PRT
<213> ORGANISM: Influenza A virus

<400> SEQUENCE: 428

Pro Tyr Asn Gly Lys Ser Ser Phe Phe Arg Asn Val Val Trp Leu Ile
1 5 10 15

Lys Lys Asn Ser Ala Tyr Gly
20

<210> SEQ ID NO 429
<211> LENGTH: 23
<212> TYPE: PRT
<213> ORGANISM: Influenza A virus

<400> SEQUENCE: 429

Pro Tyr Asn Gly Lys Ser Ser Phe Phe Arg Asn Val Val Trp Leu Ile
1 5 10 15

Lys Lys Asn Ser Thr Tyr Gly
20

<210> SEQ ID NO 430
<211> LENGTH: 23
<212> TYPE: PRT
<213> ORGANISM: Influenza A virus

<400> SEQUENCE: 430

Pro Tyr Asn Gly Lys Ser Ser Phe Phe Arg Asn Val Val Trp Leu Ile
1 5 10 15

Lys Lys Asn Ser Val Tyr Gly
20

<210> SEQ ID NO 431
<211> LENGTH: 23
<212> TYPE: PRT
<213> ORGANISM: Influenza A virus

<400> SEQUENCE: 431

Pro Tyr Leu Gly Lys Ser Ser Phe Phe Arg Asn Val Val Trp Leu Ile

-continued

```
1               5                   10                  15

Lys Lys Asn Ser Ala Tyr Gly
            20


<210> SEQ ID NO 432
<211> LENGTH: 23
<212> TYPE: PRT
<213> ORGANISM: Influenza A virus

<400> SEQUENCE: 432

Pro Tyr Leu Gly Lys Ser Ser Phe Phe Arg Asn Val Val Trp Leu Ile
1               5                   10                  15

Lys Lys Asn Ser Thr Tyr Gly
            20


<210> SEQ ID NO 433
<211> LENGTH: 23
<212> TYPE: PRT
<213> ORGANISM: Influenza A virus

<400> SEQUENCE: 433

Pro Tyr Leu Gly Lys Ser Ser Phe Phe Arg Asn Val Val Trp Leu Ile
1               5                   10                  15

Lys Lys Asn Ser Val Tyr Gly
            20


<210> SEQ ID NO 434
<211> LENGTH: 23
<212> TYPE: PRT
<213> ORGANISM: Influenza A virus

<400> SEQUENCE: 434

Pro Tyr Gln Gly Lys Ser Ser Phe Phe Arg Asn Val Val Trp Leu Ile
1               5                   10                  15

Lys Lys Asn Asn Ala Tyr Gly
            20


<210> SEQ ID NO 435
<211> LENGTH: 23
<212> TYPE: PRT
<213> ORGANISM: Influenza A virus

<400> SEQUENCE: 435

Pro Tyr Gln Gly Lys Ser Ser Phe Phe Arg Asn Val Val Trp Leu Ile
1               5                   10                  15

Lys Lys Asn Asn Thr Tyr Gly
            20


<210> SEQ ID NO 436
<211> LENGTH: 23
<212> TYPE: PRT
<213> ORGANISM: Influenza A virus

<400> SEQUENCE: 436

Pro Tyr Gln Gly Lys Ser Ser Phe Phe Arg Asn Val Val Trp Leu Ile
1               5                   10                  15

Lys Lys Asn Asn Val Tyr Gly
            20


<210> SEQ ID NO 437
<211> LENGTH: 23
<212> TYPE: PRT
```

-continued

<213> ORGANISM: Influenza A virus

<400> SEQUENCE: 437

Pro Tyr Asn Gly Lys Ser Ser Phe Phe Arg Asn Val Val Trp Leu Ile
1 5 10 15

Lys Lys Asn Asn Ala Tyr Gly
20

<210> SEQ ID NO 438
<211> LENGTH: 23
<212> TYPE: PRT
<213> ORGANISM: Influenza A virus

<400> SEQUENCE: 438

Pro Tyr Asn Gly Lys Ser Ser Phe Phe Arg Asn Val Val Trp Leu Ile
1 5 10 15

Lys Lys Asn Asn Thr Tyr Gly
20

<210> SEQ ID NO 439
<211> LENGTH: 23
<212> TYPE: PRT
<213> ORGANISM: Influenza A virus

<400> SEQUENCE: 439

Pro Tyr Asn Gly Lys Ser Ser Phe Phe Arg Asn Val Val Trp Leu Ile
1 5 10 15

Lys Lys Asn Asn Val Tyr Gly
20

<210> SEQ ID NO 440
<211> LENGTH: 23
<212> TYPE: PRT
<213> ORGANISM: Influenza A virus

<400> SEQUENCE: 440

Pro Tyr Leu Gly Lys Ser Ser Phe Phe Arg Asn Val Val Trp Leu Ile
1 5 10 15

Lys Lys Asn Asn Ala Tyr Gly
20

<210> SEQ ID NO 441
<211> LENGTH: 23
<212> TYPE: PRT
<213> ORGANISM: Influenza A virus

<400> SEQUENCE: 441

Pro Tyr Leu Gly Lys Ser Ser Phe Phe Arg Asn Val Val Trp Leu Ile
1 5 10 15

Lys Lys Asn Asn Thr Tyr Gly
20

<210> SEQ ID NO 442
<211> LENGTH: 23
<212> TYPE: PRT
<213> ORGANISM: Influenza A virus

<400> SEQUENCE: 442

Pro Tyr Leu Gly Lys Ser Ser Phe Phe Arg Asn Val Val Trp Leu Ile
1 5 10 15

Lys Lys Asn Asn Val Tyr Gly
20

<210> SEQ ID NO 443
<211> LENGTH: 23
<212> TYPE: PRT
<213> ORGANISM: Influenza A virus

<400> SEQUENCE: 443

Pro Tyr Gln Gly Arg Ser Ser Phe Phe Arg Asn Val Val Trp Leu Ile
1 5 10 15

Lys Lys Asn Ser Ala Tyr Gly
20

<210> SEQ ID NO 444
<211> LENGTH: 23
<212> TYPE: PRT
<213> ORGANISM: Influenza A virus

<400> SEQUENCE: 444

Pro Tyr Gln Gly Arg Ser Ser Phe Phe Arg Asn Val Val Trp Leu Ile
1 5 10 15

Lys Lys Asn Ser Thr Tyr Gly
20

<210> SEQ ID NO 445
<211> LENGTH: 23
<212> TYPE: PRT
<213> ORGANISM: Influenza A virus

<400> SEQUENCE: 445

Pro Tyr Gln Gly Arg Ser Ser Phe Phe Arg Asn Val Val Trp Leu Ile
1 5 10 15

Lys Lys Asn Ser Val Tyr Gly
20

<210> SEQ ID NO 446
<211> LENGTH: 23
<212> TYPE: PRT
<213> ORGANISM: Influenza A virus

<400> SEQUENCE: 446

Pro Tyr Asn Gly Arg Ser Ser Phe Phe Arg Asn Val Val Trp Leu Ile
1 5 10 15

Lys Lys Asn Ser Ala Tyr Gly
20

<210> SEQ ID NO 447
<211> LENGTH: 23
<212> TYPE: PRT
<213> ORGANISM: Influenza A virus

<400> SEQUENCE: 447

Pro Tyr Asn Gly Arg Ser Ser Phe Phe Arg Asn Val Val Trp Leu Ile
1 5 10 15

Lys Lys Asn Ser Thr Tyr Gly
20

<210> SEQ ID NO 448
<211> LENGTH: 23
<212> TYPE: PRT
<213> ORGANISM: Influenza A virus

<400> SEQUENCE: 448

-continued

Pro Tyr Asn Gly Arg Ser Ser Phe Phe Arg Asn Val Val Trp Leu Ile
1 5 10 15

Lys Lys Asn Ser Val Tyr Gly
20

<210> SEQ ID NO 449
<211> LENGTH: 23
<212> TYPE: PRT
<213> ORGANISM: Influenza A virus

<400> SEQUENCE: 449

Pro Tyr Leu Gly Arg Ser Ser Phe Phe Arg Asn Val Val Trp Leu Ile
1 5 10 15

Lys Lys Asn Ser Ala Tyr Gly
20

<210> SEQ ID NO 450
<211> LENGTH: 23
<212> TYPE: PRT
<213> ORGANISM: Influenza A virus

<400> SEQUENCE: 450

Pro Tyr Leu Gly Arg Ser Ser Phe Phe Arg Asn Val Val Trp Leu Ile
1 5 10 15

Lys Lys Asn Ser Thr Tyr Gly
20

<210> SEQ ID NO 451
<211> LENGTH: 23
<212> TYPE: PRT
<213> ORGANISM: Influenza A virus

<400> SEQUENCE: 451

Pro Tyr Leu Gly Arg Ser Ser Phe Phe Arg Asn Val Val Trp Leu Ile
1 5 10 15

Lys Lys Asn Ser Val Tyr Gly
20

<210> SEQ ID NO 452
<211> LENGTH: 23
<212> TYPE: PRT
<213> ORGANISM: Influenza A virus

<400> SEQUENCE: 452

Pro Tyr Gln Gly Arg Ser Ser Phe Phe Arg Asn Val Val Trp Leu Ile
1 5 10 15

Lys Lys Asn Asn Ala Tyr Gly
20

<210> SEQ ID NO 453
<211> LENGTH: 23
<212> TYPE: PRT
<213> ORGANISM: Influenza A virus

<400> SEQUENCE: 453

Pro Tyr Gln Gly Arg Ser Ser Phe Phe Arg Asn Val Val Trp Leu Ile
1 5 10 15

Lys Lys Asn Asn Thr Tyr Gly
20

<210> SEQ ID NO 454
<211> LENGTH: 23

-continued

<212> TYPE: PRT
<213> ORGANISM: Influenza A virus

<400> SEQUENCE: 454

Pro Tyr Gln Gly Arg Ser Ser Phe Phe Arg Asn Val Val Trp Leu Ile
1 5 10 15

Lys Lys Asn Asn Val Tyr Gly
20

<210> SEQ ID NO 455
<211> LENGTH: 23
<212> TYPE: PRT
<213> ORGANISM: Influenza A virus

<400> SEQUENCE: 455

Pro Tyr Asn Gly Arg Ser Ser Phe Phe Arg Asn Val Val Trp Leu Ile
1 5 10 15

Lys Lys Asn Asn Ala Tyr Gly
20

<210> SEQ ID NO 456
<211> LENGTH: 23
<212> TYPE: PRT
<213> ORGANISM: Influenza A virus

<400> SEQUENCE: 456

Pro Tyr Asn Gly Arg Ser Ser Phe Phe Arg Asn Val Val Trp Leu Ile
1 5 10 15

Lys Lys Asn Asn Thr Tyr Gly
20

<210> SEQ ID NO 457
<211> LENGTH: 23
<212> TYPE: PRT
<213> ORGANISM: Influenza A virus

<400> SEQUENCE: 457

Pro Tyr Asn Gly Arg Ser Ser Phe Phe Arg Asn Val Val Trp Leu Ile
1 5 10 15

Lys Lys Asn Asn Val Tyr Gly
20

<210> SEQ ID NO 458
<211> LENGTH: 23
<212> TYPE: PRT
<213> ORGANISM: Influenza A virus

<400> SEQUENCE: 458

Pro Tyr Leu Gly Arg Ser Ser Phe Phe Arg Asn Val Val Trp Leu Ile
1 5 10 15

Lys Lys Asn Asn Ala Tyr Gly
20

<210> SEQ ID NO 459
<211> LENGTH: 23
<212> TYPE: PRT
<213> ORGANISM: Influenza A virus

<400> SEQUENCE: 459

Pro Tyr Leu Gly Arg Ser Ser Phe Phe Arg Asn Val Val Trp Leu Ile
1 5 10 15

Lys Lys Asn Asn Thr Tyr Gly

-continued

20

<210> SEQ ID NO 460
<211> LENGTH: 23
<212> TYPE: PRT
<213> ORGANISM: Influenza A virus

<400> SEQUENCE: 460

Pro Tyr Leu Gly Arg Ser Ser Phe Phe Arg Asn Val Val Trp Leu Ile
1 5 10 15

Lys Lys Asn Asn Val Tyr Gly
20

<210> SEQ ID NO 461
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 461

Pro Tyr Gln Gly Lys Ser Ser Phe Phe Arg Asn Val Val Trp Leu Ile
1 5 10 15

Lys Lys Asn Ser Ala Tyr Gly
20

<210> SEQ ID NO 462
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 462

Pro Tyr Gln Gly Lys Ser Ser Phe Phe Arg Asn Val Val Trp Leu Ile
1 5 10 15

Lys Lys Asn Ser Thr Tyr Gly
20

<210> SEQ ID NO 463
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 463

Pro Tyr Gln Gly Lys Ser Ser Phe Phe Arg Asn Val Val Trp Leu Ile
1 5 10 15

Lys Lys Asn Ser Val Tyr Gly
20

<210> SEQ ID NO 464
<211> LENGTH: 23
<212> TYPE: PRT
<213> ORGANISM: Influenza A virus
<220> FEATURE:

-continued

```
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 464

Pro Tyr Asn Gly Lys Ser Ser Phe Phe Arg Asn Val Val Trp Leu Ile
1               5                   10                  15

Lys Lys Asn Ser Ala Tyr Gly
            20


<210> SEQ ID NO 465
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 465

Pro Tyr Asn Gly Lys Ser Ser Phe Phe Arg Asn Val Val Trp Leu Ile
1               5                   10                  15

Lys Lys Asn Ser Thr Tyr Gly
            20


<210> SEQ ID NO 466
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 466

Pro Tyr Asn Gly Lys Ser Ser Phe Phe Arg Asn Val Val Trp Leu Ile
1               5                   10                  15

Lys Lys Asn Ser Val Tyr Gly
            20


<210> SEQ ID NO 467
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 467

Pro Tyr Leu Gly Lys Ser Ser Phe Phe Arg Asn Val Val Trp Leu Ile
1               5                   10                  15

Lys Lys Asn Ser Ala Tyr Gly
            20


<210> SEQ ID NO 468
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
```

di-palmitoyl-Lys-Ser-Ser-

<400> SEQUENCE: 468

Pro Tyr Leu Gly Lys Ser Ser Phe Phe Arg Asn Val Val Trp Leu Ile
1 5 10 15

Lys Lys Asn Ser Thr Tyr Gly
20

<210> SEQ ID NO 469
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 469

Pro Tyr Leu Gly Lys Ser Ser Phe Phe Arg Asn Val Val Trp Leu Ile
1 5 10 15

Lys Lys Asn Ser Val Tyr Gly
20

<210> SEQ ID NO 470
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 470

Pro Tyr Gln Gly Lys Ser Ser Phe Phe Arg Asn Val Val Trp Leu Ile
1 5 10 15

Lys Lys Asn Asn Ala Tyr Gly
20

<210> SEQ ID NO 471
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 471

Pro Tyr Gln Gly Lys Ser Ser Phe Phe Arg Asn Val Val Trp Leu Ile
1 5 10 15

Lys Lys Asn Asn Thr Tyr Gly
20

<210> SEQ ID NO 472
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 472

-continued

Pro Tyr Gln Gly Lys Ser Ser Phe Phe Arg Asn Val Val Trp Leu Ile
1 5 10 15

Lys Lys Asn Asn Val Tyr Gly
20

<210> SEQ ID NO 473
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 473

Pro Tyr Asn Gly Lys Ser Ser Phe Phe Arg Asn Val Val Trp Leu Ile
1 5 10 15

Lys Lys Asn Asn Ala Tyr Gly
20

<210> SEQ ID NO 474
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 474

Pro Tyr Asn Gly Lys Ser Ser Phe Phe Arg Asn Val Val Trp Leu Ile
1 5 10 15

Lys Lys Asn Asn Thr Tyr Gly
20

<210> SEQ ID NO 475
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 475

Pro Tyr Asn Gly Lys Ser Ser Phe Phe Arg Asn Val Val Trp Leu Ile
1 5 10 15

Lys Lys Asn Asn Val Tyr Gly
20

<210> SEQ ID NO 476
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 476

Pro Tyr Leu Gly Lys Ser Ser Phe Phe Arg Asn Val Val Trp Leu Ile
1 5 10 15

-continued

```
Lys Lys Asn Asn Ala Tyr Gly
            20


<210> SEQ ID NO 477
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 477

Pro Tyr Leu Gly Lys Ser Ser Phe Phe Arg Asn Val Val Trp Leu Ile
1               5                   10                  15

Lys Lys Asn Asn Thr Tyr Gly
            20


<210> SEQ ID NO 478
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 478

Pro Tyr Leu Gly Lys Ser Ser Phe Phe Arg Asn Val Val Trp Leu Ile
1               5                   10                  15

Lys Lys Asn Asn Val Tyr Gly
            20


<210> SEQ ID NO 479
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 479

Pro Tyr Gln Gly Arg Ser Ser Phe Phe Arg Asn Val Val Trp Leu Ile
1               5                   10                  15

Lys Lys Asn Ser Ala Tyr Gly
            20


<210> SEQ ID NO 480
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 480

Pro Tyr Gln Gly Arg Ser Ser Phe Phe Arg Asn Val Val Trp Leu Ile
1               5                   10                  15

Lys Lys Asn Ser Thr Tyr Gly
            20
```

<210> SEQ ID NO 481
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 481

Pro Tyr Gln Gly Arg Ser Ser Phe Phe Arg Asn Val Val Trp Leu Ile
1 5 10 15

Lys Lys Asn Ser Val Tyr Gly
20

<210> SEQ ID NO 482
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 482

Pro Tyr Asn Gly Arg Ser Ser Phe Phe Arg Asn Val Val Trp Leu Ile
1 5 10 15

Lys Lys Asn Ser Ala Tyr Gly
20

<210> SEQ ID NO 483
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 483

Pro Tyr Asn Gly Arg Ser Ser Phe Phe Arg Asn Val Val Trp Leu Ile
1 5 10 15

Lys Lys Asn Ser Thr Tyr Gly
20

<210> SEQ ID NO 484
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 484

Pro Tyr Asn Gly Arg Ser Ser Phe Phe Arg Asn Val Val Trp Leu Ile
1 5 10 15

Lys Lys Asn Ser Val Tyr Gly
20

<210> SEQ ID NO 485

-continued

<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 485

```
Pro Tyr Leu Gly Arg Ser Ser Phe Phe Arg Asn Val Val Trp Leu Ile
1               5                   10                  15

Lys Lys Asn Ser Ala Tyr Gly
            20
```

<210> SEQ ID NO 486
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 486

```
Pro Tyr Leu Gly Arg Ser Ser Phe Phe Arg Asn Val Val Trp Leu Ile
1               5                   10                  15

Lys Lys Asn Ser Thr Tyr Gly
            20
```

<210> SEQ ID NO 487
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 487

```
Pro Tyr Leu Gly Arg Ser Ser Phe Phe Arg Asn Val Val Trp Leu Ile
1               5                   10                  15

Lys Lys Asn Ser Val Tyr Gly
            20
```

<210> SEQ ID NO 488
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with di-palmitoyl-Lys-Ser-Ser-

<400> SEQUENCE: 488

```
Pro Tyr Gln Gly Arg Ser Ser Phe Phe Arg Asn Val Val Trp Leu Ile
1               5                   10                  15

Lys Lys Asn Asn Ala Tyr Gly
            20
```

<210> SEQ ID NO 489
<211> LENGTH: 23
<212> TYPE: PRT
<213> ORGANISM: Influenza A virus -continued

```
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 489

Pro Tyr Gln Gly Arg Ser Ser Phe Phe Arg Asn Val Val Trp Leu Ile
1               5                   10                  15

Lys Lys Asn Asn Thr Tyr Gly
            20


<210> SEQ ID NO 490
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 490

Pro Tyr Gln Gly Arg Ser Ser Phe Phe Arg Asn Val Val Trp Leu Ile
1               5                   10                  15

Lys Lys Asn Asn Val Tyr Gly
            20


<210> SEQ ID NO 491
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 491

Pro Tyr Asn Gly Arg Ser Ser Phe Phe Arg Asn Val Val Trp Leu Ile
1               5                   10                  15

Lys Lys Asn Asn Ala Tyr Gly
            20


<210> SEQ ID NO 492
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 492

Pro Tyr Asn Gly Arg Ser Ser Phe Phe Arg Asn Val Val Trp Leu Ile
1               5                   10                  15

Lys Lys Asn Asn Thr Tyr Gly
            20


<210> SEQ ID NO 493
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
```

-continued

```
<223> OTHER INFORMATION: residue lipidated, for example with
      di-palmitoyl-Lys-Ser-Ser-

<400> SEQUENCE: 493

Pro Tyr Asn Gly Arg Ser Ser Phe Phe Arg Asn Val Val Trp Leu Ile
1               5                   10                  15

Lys Lys Asn Asn Val Tyr Gly
            20


<210> SEQ ID NO 494
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 494

Pro Tyr Leu Gly Arg Ser Ser Phe Phe Arg Asn Val Val Trp Leu Ile
1               5                   10                  15

Lys Lys Asn Asn Ala Tyr Gly
            20


<210> SEQ ID NO 495
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 495

Pro Tyr Leu Gly Arg Ser Ser Phe Phe Arg Asn Val Val Trp Leu Ile
1               5                   10                  15

Lys Lys Asn Asn Thr Tyr Gly
            20


<210> SEQ ID NO 496
<211> LENGTH: 23
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: residue lipidated, for example with
      di-palmitoyl-Lys-Ser-Ser-

<400> SEQUENCE: 496

Pro Tyr Leu Gly Arg Ser Ser Phe Phe Arg Asn Val Val Trp Leu Ile
1               5                   10                  15

Lys Lys Asn Asn Val Tyr Gly
            20
```